US008815852B2

(12) United States Patent
Lee et al.

(10) Patent No.: US 8,815,852 B2
(45) Date of Patent: *Aug. 26, 2014

(54) CARBAMOYLOXY ARYLALKAN ARYLPIPERAZINE ANALGESICS

(75) Inventors: Ki Ho Lee, Daejeon (KR); Han Ju Yi, Daejeon (KR); Hyeon Cho, Daejeon (KR); Dae Joong Im, Daejeon (KR); Eun Hee Chae, Daejeon (KR); Yeon Jung Choi, Daejeon (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 1303 days.

This patent is subject to a terminal disclaimer.

(21) Appl. No.: 12/600,283

(22) PCT Filed: Apr. 30, 2008

(86) PCT No.: PCT/KR2008/002466
§ 371 (c)(1),
(2), (4) Date: Feb. 23, 2011

(87) PCT Pub. No.: WO2008/140197
PCT Pub. Date: Nov. 20, 2008

(65) Prior Publication Data
US 2010/0160331 A1 Jun. 24, 2010
US 2012/0095007 A2 Apr. 19, 2012

(30) Foreign Application Priority Data

May 14, 2007 (KR) ........................ 10-2007-0046708

(51) Int. Cl.
C07D 307/54 (2006.01)
C07D 239/42 (2006.01)
C07D 213/74 (2006.01)
C07D 241/04 (2006.01)
C07D 265/36 (2006.01)
C07D 241/44 (2006.01)
C07D 265/18 (2006.01)
C07D 295/033 (2006.01)
C07D 317/66 (2006.01)
C07D 317/58 (2006.01)
C07D 319/18 (2006.01)

(52) U.S. Cl.
CPC ............ *C07D 239/42* (2013.01); *C07D 241/04* (2013.01); *C07D 265/36* (2013.01); *C07D 241/44* (2013.01); *C07D 265/18* (2013.01); *C07D 295/033* (2013.01); *C07D 317/66* (2013.01); *C07D 317/58* (2013.01); *C07D 319/18* (2013.01); *C07D 307/54* (2013.01); *C07D 213/74* (2013.01)
USPC .............. 514/230.5; 514/252.11; 514/253.13; 514/254.11; 514/255.03; 544/92; 544/357; 544/360; 544/377; 544/379; 544/391

(58) Field of Classification Search
USPC ............... 514/230.5, 252.11, 253.13, 254.11, 514/255.03; 544/92, 357, 360, 377, 391, 544/379
See application file for complete search history.

(56) References Cited

U.S. PATENT DOCUMENTS

| 3,002,976 | A | 10/1961 | Janssen |
| 3,135,756 | A | 6/1964 | Shapiro et al. ................. 260/268 |
| 4,476,129 | A | 10/1984 | Gootjes et al. |
| 4,605,655 | A | 8/1986 | Yevich et al. |
| 4,988,814 | A | 1/1991 | Abou-Gharbia et al. |
| 6,838,461 | B1 | 1/2005 | Boettcher et al. |
| 2004/0072839 | A1 | 4/2004 | Leonardi et al. ......... 514/252.12 |
| 2006/0252778 | A1 | 11/2006 | Guo et al. |
| 2010/0145048 | A1 | 6/2010 | Guo et al. |
| 2013/0131081 | A1* | 5/2013 | Moon et al. ............... 514/254.11 |

FOREIGN PATENT DOCUMENTS

| EP | 0 395 313 | * 4/1990 | ........... C07D 295/08 |
| EP | 0395313 | 12/1999 | ........... C07D 295/08 |
| EP | 1008594 | 6/2000 | |
| JP | 50-040583 | 5/1974 | ........... C07D 295/08 |
| JP | 61-000075 | 1/1986 | ........... C07D 239/42 |
| JP | 03-011059 | 1/1991 | ........... C07D 205/04 |
| JP | 2002511883 | 4/2002 | ........... C07D 333/56 |
| JP | 2006-502102 | 1/2006 | ........... C07D 209/40 |
| WO | 9839324 | 9/1998 | |
| WO | 0248124 | 6/2002 | |
| WO | 03068236 | 8/2003 | |
| WO | 2004018423 | 3/2004 | |
| WO | 2005058823 | 6/2005 | |
| WO | 0240466 | 5/2006 | |
| WO | 2006112685 | 10/2006 | |
| WO | 2008019971 | 2/2008 | |

OTHER PUBLICATIONS

West, Anthony R., Solid State Chemistry and Its Applications, Wiley, New York, 1988, 358.*

(Continued)

Primary Examiner — Erich A Leeser
(74) Attorney, Agent, or Firm — Harness, Dickey & Pierce, P.L.C.

(57) ABSTRACT

There is provided a novel carbamoyloxy arylalkanoyl arylpiperazine derivative compound having abundant racemic or enantiomeric characteristics, represented by the Formula 1, and pharmaceutically available salts or hydrates thereof. Also, there are provided a pharmaceutical composition for treating pain, anxiety or depression including an effective amount of the compound, and a method for treating pain, anxiety or depression in mammals by administering an effective amount of the compound to the mammals in need of treatment thereof.

20 Claims, No Drawings

(56) References Cited

OTHER PUBLICATIONS

The Chilean Office Action mailed Jun. 14, 2012 from the Chilean Patent Office in the related Chilean Patent application No. 2009-2112.

The Office Action mailed on Nov. 26, 2012 in related U.S. Appl. No. 12/600,291.

Joseph P. Yevich et al. "Synthesis and biological characterization of alpha-(4-fluorophenyl)-4-(5-fluoro-2-pyrimidinyl)-1-piperazinebutanol and analogues as potential atypical antipsychotic agents." J. Med. Chem vol. 35(24), pp. 4516-4525, 1992.

Pharmaceutical Salts, J. Pharm. Sci., 1977;66(1):1-19.

Middlemiss et al. (1984, Eur. J. Pharmacol).

Leysen et al. (1982, Eur. J. Pharmacol).

The extended European Search Report by the European Patent Office, issued on Oct. 11, 2010, in the European patent application No. 08753266.9.

The extended European Search Report by the European Patent Office, issued on Oct. 11, 2010, in the European patent application No. 08753270.1.

The International Search Report and Written Opinion by the International Searching Authority, issued on Sep. 26, 2008, in the PCT application No. PCT/KR2008/002466.

The International Search Report and Written Opinion by the International Searching Authority, issued on Oct. 23, 2008, in the PCT application No. PCT/KR2008/002470.

Darmani, "The silent and selective 5-HT1A antagonist, WAY 100635, produces via an indirect mechanism, a 5-HT2A receptor-mediated behaviour in mice during the day but not at night," J. Neural Transm. 1998;105(6-7):635-43.

Office Action, dated Apr. 10, 2013, issued in Japanese Application No. 2010508290.

\* cited by examiner

CARBAMOYLOXY ARYLALKAN ARYLPIPERAZINE ANALGESICS

TECHNICAL FIELD

The present invention relates to novel carbamoyloxy arylalkan arylpiperazine compound, a pharmaceutical compositions comprising the compound and a method for treating pains including acute pain, chronic pain, neuropathic pain, post-surgery neuropathic pain, diabetic neuropathic pain, postherpetic neuralgia, inflammatory pain, joint pain, migraine headache and the like, anxiety and depression in mammals by administering the compound to the mammals in need of treatment thereof.

BACKGROUND ART

Up to now, arylpiperazine compounds were proven to be effective to a variety of indications in the field of central nervous system. In particular, U.S. Pat. No. 3,002,976 reported that the following thiophene-engrafted arylpiperazine compound has a pharmacological effect to treat depression. In this formula, R represents hydrogen, methyl group or halogen.

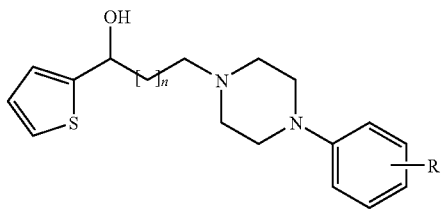

Also, it has been known that effects of buspirone and its structurally related compounds on the treatment of anxiety is due to their selective activities in serotonin (5-hydroxytryptamine: 5HT) sub-type receptor represented by a receptor 5-HT1A. In particular, U.S. Pat. No. 4,988,814 discloses piperazine derivatives showing affinity to the 5-HT1A receptor characterized as therapeutic agents to treat depression and anxiety.

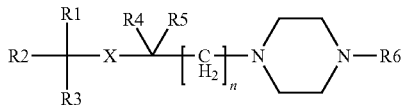

wherein, R' is alkyl having carbon atoms of 1 to 6; $R^2$ and $R^3$ are each independently alkyl having carbon atoms of 1 to 6, or $R^2$ and $R^3$ are taken together to form polymethylene having carbon atoms of 2 to 12 or to form a 5-norbornen-2-yl residue with carbon atoms bount to the radicals $R^2$ and $R^3$; X is selected from the group consisting of —$CO_2$—, —OCO—, —$OCO_2$—$N(R^7)CO$—, —NHNHCO—, —$ON(R^7)CO$—, —$CON(R^7)$—, —$N(R^7)CO_2$—, —$OCON(R^7)$— and —$N(R^7)CON(R^8)$ (wherein, $R^7$ and $R^8$ are each independently is selected from the group consisting of hydrogen; alkyl having carbon atoms of 1 to 6; phenyl; benzyl; and phenyl or benzyl substituted by halo, alkyl having carbon atoms of 1 to 6, alkoxy having carbon atoms of 1 to 6, cyano, nitro or perhalomethyl); $R^4$ is hydrogen or alkyl having carbon atoms of 1 to 6; $R^5$ is selected from the group consisting of hydrogen; alkyl having carbon atoms of 1 to 8; hydroxyalkyl having carbon atoms of 1 to 3; phenyl; benzyl; and phenyl or benzyl substituted by hydroxy, halo, alkyl having carbon atoms of 1 to 6, alkoxy having carbon atoms of 1 to 6, trifluoromethyl, nitro, cyano, carbalkoxy having carbon atoms of 2 to 7, carboxamido, amino, alkylamino having carbon atoms of 1 to 6 or dialkylamino having carbon atoms of 2 to 12; $R^6$ is phenyl, benzyl, 2-, 3- or 4-pyridinyl, 2-pyrimidinyl or 2-pyrazinyl that may be substituted by at least one substituents selected from the group consisting of hydroxy, halo, alkyl having carbon atoms of 1 to 6, alkoxy having carbon atoms of 1 to 6, trifluoromethyl, nitro, cyano, carbalkoxy having carbon atoms of 2 to 7, carboxamido, amino, alkylamino having carbon atoms of 1 to 6, and dialkylamino having carbon atoms of 2 to 12; n is one integer selected from the group consisting of 0, 1, 2, 3, 4 and 5, provided that $R^6$ is not 2-pyrimidinyl when X is —$CON(R^7)$— (wherein, $R^7$ is alkyl), and $R^6$ is not 3,5-di(trifluoromethyl)phenyl when X is $CO_2$, $R^1$, $R^2$ and $R^3$ are methyl and n is 1.

The present inventors have confirmed that an arylpiperazine structure is correlated with an effect to treat pains as well as anxiety and depression, conducted comprehensive researches on the arylpiperazine structure, and found that novel carbamoyloxy arylalkan arylpiperazine compounds have a medical effect in various pain-induced animal models. In particular, the present inventors have found that the novel carbamoyloxy arylalkan arylpiperazine compounds show their therapeutic effects to treat a wide scope of pains including acute pain, chronic pain, neuropathic pain, post-surgery neuropathic pain, diabetic neuropathic pain, postherpetic neuralgia, inflammatory pain, joint pain, migraine headache and the like, anxiety and depression. Therefore, the present invention was completed on the basis of the above-mentioned facts.

DISCLOSURE OF INVENTION

Technical Problem

An aspect of the present invention provides a novel carbamoyloxy arylalkan arylpiperazine derivative compound and pharmaceutically available salts or hydrates thereof.

Another aspect of the present invention provides a pharmaceutical composition for treating pain, anxiety or depression including an effective amount of the compound.

Still another aspect of the present invention provides a method for treating pain, anxiety or depression in mammals by administering an effective amount of the compound to the mammals in need of treatment thereof.

Technical Solution

According to an aspect of the present invention, there is provided a carbamoyloxy arylalkan arylpiperazine derivative compound having abundant racemic or enantiomeric characteristics, represented by the following Formula 1, and pharmaceutically available salts or hydrates thereof:

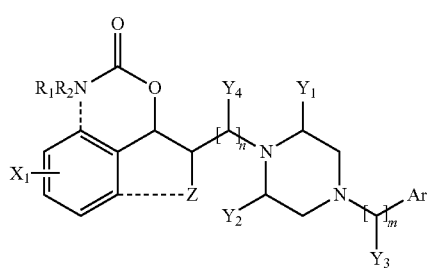

Formula 1 wherein, - - - may selectively form a cyclic ring;
$R_1$ and $R_2$ are hydrogen, or $R_1$ or $R_2$ may be taken together with $X_1$ to form a bicyclic ring;

$X_1$ represents the phenyl ring being substituted by at least one identical or different substituent selected from the group consisting of hydrogen, straight or branched alkyl having 1 to 6 carbon atoms, halogen such as F, Cl and Br, straight or branched alkoxy having 1 to 6 carbon atoms, nitro, dimethylamino, and trifluoromethyl; or $X_1$ taken together with the phenyl ring is a bicyclic ring including naphthyl and methylenedioxyphenyl;

Z is hydrogen or fluorine, or may be taken together with $X_1$ to form a bicyclic ring;

Ar is selected from the group consisting of phenyl, pyridine, pyrimidine which may be substituted by at least one identical or different substituent selected from the group consisting of hydrogen, straight or branched alkyl having carbon atoms of 1 to 6, hydroxy, halogen, straight or branched alkoxy having carbon atoms of 1 to 6, nitro, acetyl, t-butylacetyl, trifluoromethyl, trifluoromethoxy, amino, benzyloxy, 3,4-methylenedioxy, 3,4-ethylenedioxy, pivaloyloxy, ethylcarbonate, phenylcarbonate, carbonic acid benzyl ester, acetate, and cyclopentyloxy; and naphthyl, dihydrobenzodioxinyl, methylenedioxyphenyl, bis(fluorophenyl)methyl and quinoxaline;

$Y_1$ and $Y_2$ are each independently hydrogen or methyl ($CH_3$);

$Y_3$ is hydrogen, phenyl, or carbonyl (=O);

$Y_4$ is hydrogen, or methyl ($CH_3$);

n is integer of 1 or 2;

m is integer of 0 or 1.

According to another aspect of the present invention, there is provided a pharmaceutical composition for treating pain, anxiety or depression including an effective amount of the compound having abundant racemic or enantiomeric characteristics.

According to still another aspect of the present invention, there is provided a method for treating pain, anxiety or depression in mammals by administering to the mammals in need of treatment thereof an effective amount of the compound having abundant racemic or enantiomeric characteristics.

Advantageous Effects

As described above, the novel carbamoyloxy arylalkan arylpiperazine derivative compound, and salts and hydrates thereof according to the present invention may be effectively used as a therapeutic agent for treating pains including acute pain, chronic pain, neuropathic pain, post-surgery neuropathic pain, diabetic pain, postherpetic neuralgia, inflammatory pain, joint pain and migraine headache, anxiety and depression.

BEST MODE FOR CARRYING OUT THE INVENTION

Hereinafter, the present invention will be described in more detail.

The present invention is related to a carbamoyloxy arylalkan arylpiperazine derivative compound having abundant racemic or enantiomeric characteristics, represented by the following Formula 1, and pharmaceutically available salts or hydrates thereof:

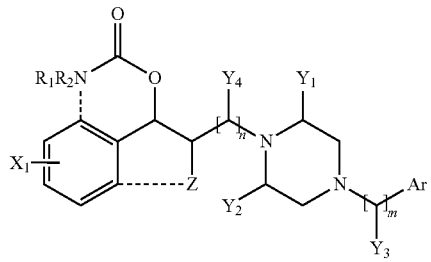

Formula 1 wherein, - - - may selectively form a cyclic ring;

$R_1$ and $R_2$ are hydrogen, or $R_1$ or $R_2$ may be taken together with $X_1$ to form a bicyclic ring;

$X_1$ represents the phenyl being substituted by at least one identical or different substituent selected from the group consisting of hydrogen, straight or branched alkyl having 1 to 6 carbon atoms, halogen such as F, Cl and Br, straight or branched alkoxy having 1 to 6 carbon atoms, nitro, dimethylamino, and trifluoromethyl; or $X_1$ taken together with the phenyl ring is a bicyclic ring including naphthyl and methylenedioxyphenyl;

Z is hydrogen or fluorine, or may be taken together with $X_1$ to form a bicyclic ring;

Ar is selected from the group consisting of phenyl, pyridine, pyrimidine which may be substituted by at least one identical or different substituent selected from the group consisting of hydrogen, straight or branched alkyl having carbon atoms of 1 to 6, hydroxy, halogen, straight or branched alkoxy having carbon atoms of 1 to 6, nitro, acetyl, t-butylacetyl, trifluoromethyl, trifluoromethoxy, amino, benzyloxy, 3,4-methylenedioxy, 3,4-ethylenedioxy, pivaloyloxy, ethylcarbonate, phenylcarbonate, carbonic acid benzyl ester, acetate, and cyclopentyloxy; and naphthyl, dihydrobenzodioxinyl, methylenedioxyphenyl, bis(fluorophenyl)methyl and quinoxaline, $Y_1$ and $Y_2$ are each independently hydrogen or methyl ($CH_3$);

$Y_3$ is hydrogen, phenyl, or carbonyl (=O);

$Y_4$ is hydrogen, or methyl ($CH_3$);

n is integer of 1 or 2;

m is integer of 0 or 1.

The compounds according to one exemplary embodiment of the present invention may be chemically synthesized as in the following Schemes 1 to 3. However, they are described for the purpose of illustrations only, and the present invention is not particularly limited thereto.

In the following Schemes, HX represents acid that may form pharmaceutically available salts with a compound having basic nitrogen. The acid includes, but is not particularly limited to, for example, hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzenesulfonic acid, methanesulfonic acid, ethanesulfonic acid, hydroxymethanesulfonic acid, hydroxyethanesulfonic acid, etc. Additional acids may refer to a literature ["Pharmaceutical Salts," *J. Pharm. Sci.*, 1977; 66(1): 1-19]. The preparation of the compound of the present invention is carried out in a reaction medium that may be illustrated as an ether solvent (tetrahydrofuran, ethylether, propylether, isopropylether, and butylether), an alcohol solvent (methanol, ethanol, and isopropyl alcohol), an ester solvent (ethyl acetate), a halogenated hydrocarbon solvent (dichloromethane, chloroform) and mixtures thereof.

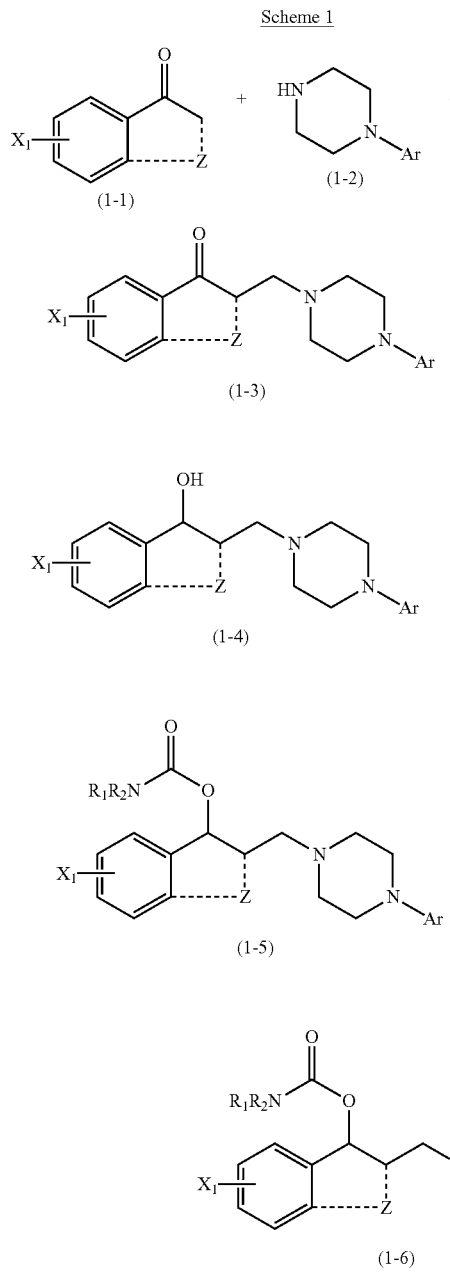

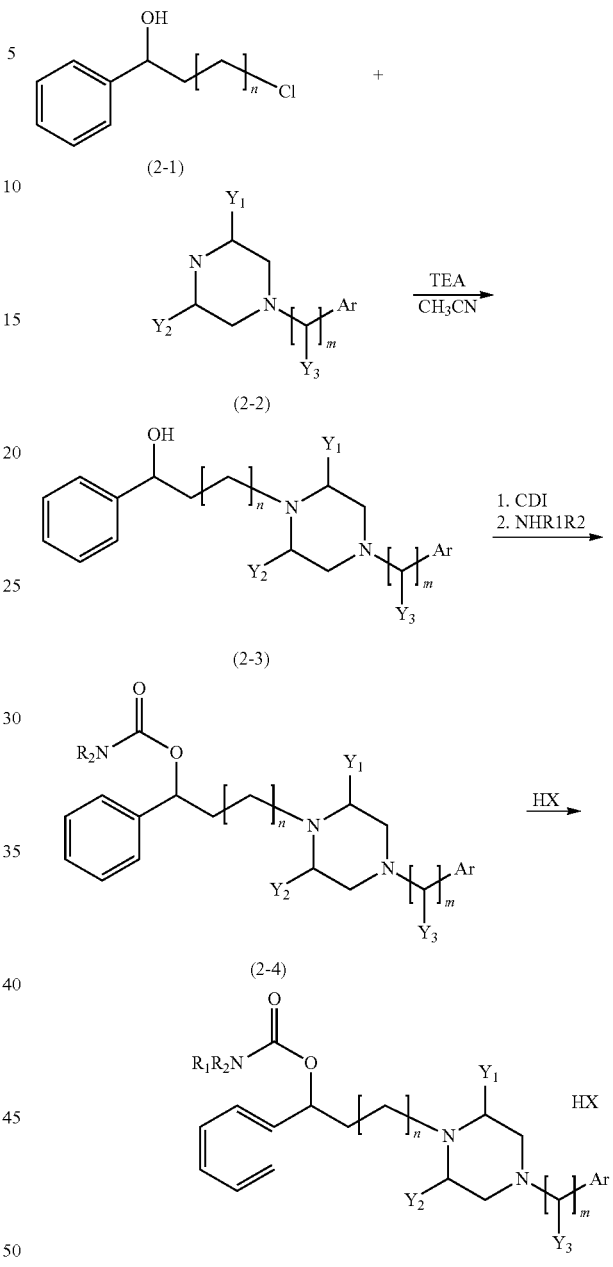

As shown in the Scheme 1, a compound (1-3) was synthesized at the presence of a starting material (1-1) substituted by $X_1$ and phenylpiperazine (1-2) substituted by $X_2$ through a Mannich reaction. A compound (1-4) was prepared by reducing the compound (1-3) with sodium borohydride ($NaBH_4$), reacted with 1,1-carbonyl dimidazole (CDI), and then reacted with various amines ($NHR_1R_2$) to obtain a compound (1-5) and its salt (1-6).

The reaction product (1-5) or its salt (1-6) prepared through the Scheme 1 was obtained in the form of a racemic compound.

As shown in the Scheme 2, a compound (2-3) engrafted by various kinds of piperazine derivatives (2-2) was prepared from a starting material '3-chloro-1-phenyl-propan-1-ol (compound (2-1) if n=1) or '4-chloro-1-phenyl-butan-1-ol (compound (2-1) if n=2), reacted with 1,1-carbonyl dimidazole (CDI), and then reacted with amines ($NHR_1R_2$) to obtain a compound (2-4) and its salt (2-5).

Stereochemistries of the reaction product (2-4) and its salt (2-5) depend only on the starting material (2-1); that is, the reaction product having an (S)-enantiomer only is obtained from the starting material (2-1) having an (S)-enantiomer, and the reaction product having a (R)-enantiomer only is obtained from the starting material (2-1) having a (R)-enantiomer.

Scheme 3

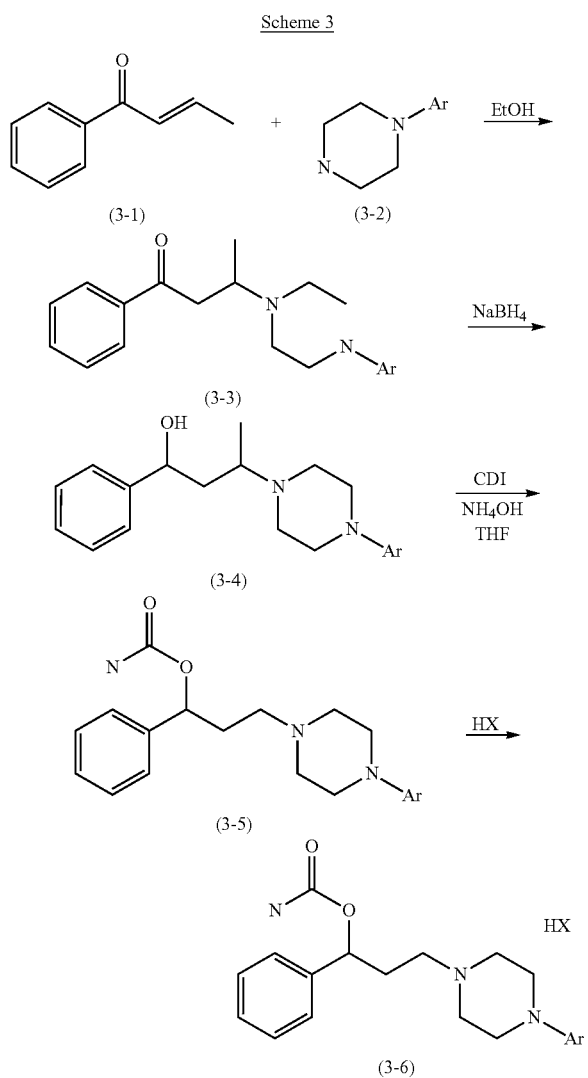

As shown in the Scheme 3, a compound (3-3) was synthesized from phenyl-1-propenylketone (3-1) and substituents-engrafted phenylpiperazine (3-2) through 1,4-Michael addition. The compound (3-3) was subject to the reduction reaction at the presence of sodium borohydride (NaBH$_4$) to obtain a compound (3-4) as an alcohol intermediate, and the compound (3-4) was reacted with 1,1-carbonyl dimidazole (CDI), as described previously above, to obtain a carbamate-engrafted compound (3-5) and its salt (3-6).

The reaction products obtained in the Scheme 3 were all obtained in the form of a racemic compound.

According to the present invention, there is provided a pharmaceutical composition including an effective amount of the compound to treat pain, anxiety or depression. Here, the pharmaceutical composition includes, as an active component, at least one compound among the compounds as listed in this application, and the composition according to the present invention may include any combination of the compounds according to the present invention.

The pharmaceutical composition of present invention may be specifically formulated so that it can be administered via any form, such as suitable routes of administration. Here, the suitable routes of administration may, for example, include oral, rectal, nasal, pulmonary, local, percutaneous, intracisternal, intraperitoneal, vaginal, and parenteral including subcutaneous, intramuscular, intrathecal, intravenous and transdermal routes) routes. The pharmaceutical composition of present invention is preferably administered via the oral route. The preferred routes of administration will, of course, be varied depending on a variety of factors, including the general conditions and age of the subject being treated, the severity of the conditions being treated, and the selected active components, etc.

Pharmaceutical preparations formulated according to the present invention may be administered orally in any form of administration, such as suitable forms of a tablet, a capsule, a powder, a granule, a pellet, a troche, a dragee, a pill or lozenge, a solution or suspension in an aqueous or non-aqueous liquid, or an oil-in-water or water-in-oil liquid emulsion, an elixir, a syrup, etc., or be administered parenterally in the form of injections. Other pharmaceutical compositions that may be administered parenterally include a dispersion, a suspension and an emulsion, as well as sterile powders included in a sterile injection solution or dispersion before their use. It is considered that a depot injection formulation is also included within the scope of the present invention. Other suitable forms of administration include a suppository, a spray, an ointment, a cream, a gelatin, an inhalant, a skin patch, etc. The composition according to the present invention may be formulated according to various methods known in the art. Also, pharmaceutically available carrier, diluent, excipient or other additives, which are used in general in the art, may be used herein.

The carrier is that which generally used in formulations, and includes, but is not particularly limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxy benzoate, talc, magnesium stearate, mineral oil, etc. The composition of the present invention may further includes a preservative, a stability-improving compound, a viscosity-improving/regulating compound, a solubility-improving compound, a sweetener, a dye, a taste-enhancing compound, an osmosis-inducing salt, a buffer, an antioxidant, etc.

Where the above-mentioned compounds show a desired effect to treat pain, anxiety or depression, the compounds may be used in the form of solvates, esters, stereoisomers, etc. including free compounds, pharmaceutically available salts and hydrates. Also, the above-mentioned compounds are all included in the scope of the present invention.

According to the present invention, the pharmaceutically available salts may include pharmaceutically available acid addition salts. The pharmaceutically available acid addition salts may be obtained from inorganic rids such as hydrochloric acid, nitric acid, phosphoric acid, sulfuric acid, hydrobromic acid, hydriodic acid, nitrous acid and phosphorous acid; and non-toxic organic acids such as aliphatic mono and di-carboxylate, phenyl-substituted alkanoate, hydroxy alkanoate and alkandioate, aromatic acids, aliphatic and aromatic sulfonic acids; and the like. Specific examples of the pharmaceutically available salts includes, but is not particularly limited to, sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propionate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, maleate, tartrate, methane sulfonate, propanesulfonate, naphthalene-1-sulfonate, naphthalene-2-sulfonate and mandelate. Particularly, hydrochloric acid and methane sulfonate are preferred.

The present invention provides a method for treating pain, anxiety or depression in mammals, characterized in that an effective amount of the compound is administered to the mammals in need of treatment thereof.

The pain, which may be treated by the compound of the present invention, includes a wide range of pains such as acute pain, chronic pain, neuropathic pain, post-surgery neuropathic pain, diabetic pain, postherpetic neuralgia, inflammatory pain, joint pain, migraine headache, etc.

In general, the pharmaceutical composition of the present invention is administered as with active component at a unit dose ranging from approximately 20 to 500 mg. The total daily dose may be generally administered at the amount ranging from approximately 10 to 7000 mg, and preferably from 20 to 3500 mg of the active compound of the present invention. However, the active compound may also be administered at a certain amount out of the dose range under general investigation of the conditions of patients, and also in consideration of the activity of agents to be administered. In this case, the optimum dose amount of such agents in the particular conditions should be determined by routine experimentations.

The compound of the present invention may be administered in single or multiple daily doses, and the dose of the compound may be preferably divided into one, two and three times per day. The compound of the present invention may be administered alone or in combination of a pharmaceutically available carrier or an excipient. The pharmaceutical composition according to the present invention may be formulated in a pharmaceutically available carrier or a diluent, as well as in a supplement and an excipient that are widely known in the art. For convenience' sake, the formulations may be present in dosages suitable for such administration by using the methods known in the field of pharmacology.

Mode for the Invention

Hereinafter, exemplary embodiments of the present invention will be described in detail. However, it should be understood that the description proposed herein is just a preferable example for the purpose of illustrations only, not intended to limit the scope of the invention.

1. Synthesis of Carbamoyloxy Arylalkan Arylpiperazine Compound

Example 1

Carbamic acid 1-phenyl-3-(4-phenyl-piperazin-1-yl)-propyl ester

Acetophenone (4.67 mmol) and phenylpiperazine (5.61 mmol) were dissolved in ethanol (30 mL), and the resulting mixture was adjusted to pH 2 to 3 by adding concentrated hydrochloric acid dropwise. Paraformaldehyde (46.7 mmol) was added to the mixture, and the resulting mixture was refluxed for 24 hours. The resulting reaction mixture were distilled under a reduced pressure, neutralized with 1 normal sodium chloride aqueous solution, diluted with water, and then extracted several times with ethylacetate. The resulting organic phase was dried over magnesium sulfate, and filtered, and the resulting filtrate was concentrated under a reduced pressure, and separated and purified with column chromatography (hexane:ethyl acetate=1:1 to 1:10). The separated compound (3.5 mmol) was dissolved in methanol (20 mL), and cooled to 0° C., and sodium borohydride (5 mmol) was added slowly to the mixture. The resulting mixture was stirred at a room temperature for 2 hours, and concentrated under a reduced pressure. Then, the resulting yellow pellet was purified with column chromatography (hexane:ethylacetate=1:1) to obtain an alcohol intermediate. The prepared intermediate (10 mmol) was dissolved in tetrahydrofuran (15 mL), and 1,1'-carbonyldiimidazole (20 mmol) was added to the intermediate mixture. The resulting intermediate mixture was stirred at a room temperature for 1 hour, and excessive ammonium hydroxide was added to the intermediate mixture, and the resulting mixture was stirred at a room temperature for additional 2 hours. The resulting reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1 to hexane:ethylacetate=0:1) to obtain a title compound.

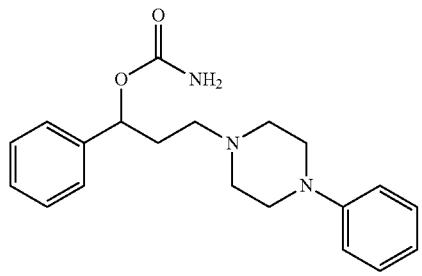 [SMILES: NC(=O)OC(CCN1CCN(c2ccccc2)CC1)c1ccccc1]

$^1$H NMR (200 MHz, CDCl$_3$) d: 1.98 (m, 1H), 2.21 (m, 1H), 2.41 (m, 2H), 2.60 (m, 4H), 3.10 (m, 4H), 4.92 (br, 2H), 5.75 (t, 1H), 6.89 (m, 4H), 7.11 (m, 5H)

Compounds of Examples 2 to 84 were prepared in the same manner as in the Example 1, except that the different starting materials were used in the Examples 2 to 84.

Example 2

Carbamic acid 1-(4-chloro-phenyl)-3-(4-phenyl-piperazin-1-yl)-propyl ester

A title compound was prepared in the same manner as in Example 1 except for the use of 4'-chloroacetophenone and phenylpiperazine as starting materials.

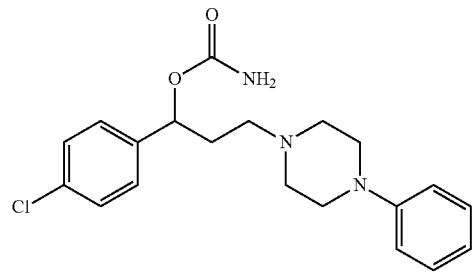 [SMILES: NC(=O)OC(CCN1CCN(c2ccccc2)CC1)c1ccc(Cl)cc1]

¹H NMR (200 MHz, CDCl₃) d: 1.99 (m, 1H), 2.16 (m, 1H), 2.33 (m, 2H), 2.45 (m, 4H), 3.01 (m, 4H), 4.57 (br, 2H), 5.51 (t, 1H), 6.80 (m, 2H), 7.19 (m, 2H), 7.28 (m, 5H)

Example 3

Carbamic acid 1-(4-dimethylamino-phenyl)-3-(4-phenyl-piperazin-1-yl)-propyl ester A title compound was prepared in the same manner as in Example 1 except for the use of 4'-dimethylaminoacetophenone and phenylpiperazine as starting materials.

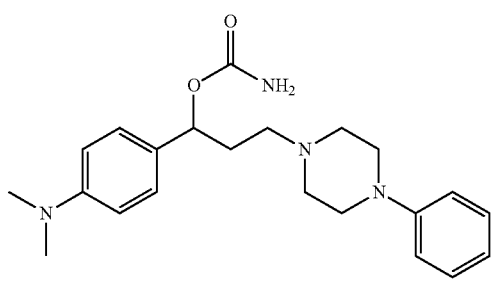 [SMILES: CN(C)c1ccc(C(CCN2CCN(c3ccccc3)CC2)OC(N)=O)cc1]

¹H NMR (200 MHz, CDCl₃) d: 2.62 (m, 3H), 2.71 (m, 1H), 2.82 (m, 2H), 2.94 (dd, 6H), 3.25 (m, 4H), 4.87 (dd, 1H), 5.8 (br, 2H), 6.71 (d, 2H), 6.9 (m, 3H), 7.26 (m, 5H)

Example 4

Carbamic acid 1-(3-nitro-phenyl)-3-(4-phenyl-piperazin-1-yl)-propyl ester

A title compound was prepared in the same manner as in Example 1 except for the use of 3'-nitroaminoacetophenone and phenylpiperazine as starting materials.

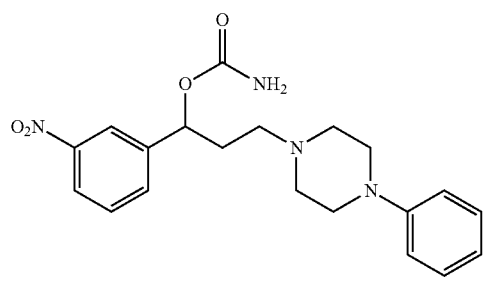 [SMILES: NC(=O)OC(CCN1CCN(c2ccccc2)CC1)c1cccc([N+](=O)[O-])c1]

¹H NMR (200 MHz, CDCl3) d: 2.58 (m, 2H), 2.66 (m, 2H), 2.95 (m, 4H), 3.36 (m, 4H), 4.86 (br, 2H), 5.80 (t, 1H), 6.89-6.97 (m, 3H), 7.29 (m, 2H), 7.54 (t, 1H), 7.75 (d, 1H), 8.15 (q, 1H), 8.29 (d, 1H)

Example 5

Carbamic acid 1-(4-tert-butyl-phenyl)-3-(4-phenyl-piperazin-1-yl)-propyl ester

A title compound was prepared in the same manner as in Example 1 except for the use of 4'-tert-butylacetophenone and phenylpiperazine as starting materials.

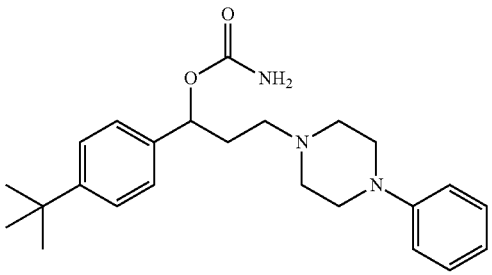 [SMILES: CC(C)(C)c1ccc(C(CCN2CCN(c3ccccc3)CC2)OC(N)=O)cc1]

¹H NMR (200 MHz, CDCl₃) d: 1.32 (s, 9H), 3.27 (m, 6H), 3.41 (m, 4H), 3.88 (m, 4H), 4.90 (br, 2H), 5.66 (t, 1H), 6.81 (m, 1H), 7.01 (m, 3H), 7.42 (m, 5H)

Example 6

Carbamic acid 1-(4-fluoro-phenyl)-3-(4-phenyl-piperazin-1-yl)-propyl ester

A title compound was prepared in the same manner as in Example 1 except for the use of 4'-fluoroacetophenone and phenylpiperazine as starting materials.

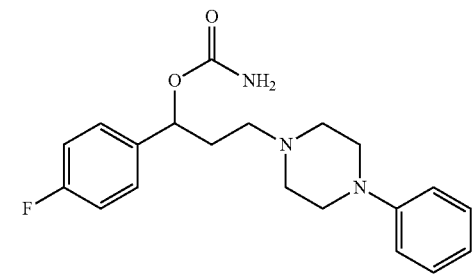 [SMILES: NC(=O)OC(CCN1CCN(c2ccccc2)CC1)c1ccc(F)cc1]

¹H NMR (200 MHz, CDCl₃) d: 1.88 (m, 2H), 2.76 (m, 6H), 3.27 (m, 2H), 4.57 (br, 2H), 5.51 (t, 1H), 6.89 (m, 4H), 7.32 (m, 5H)

Example 7

Carbamic acid 1-(3-chloro-phenyl)-3-(4-phenyl-piperazin-1-yl)-propyl ester

A title compound was prepared in the same manner as in Example 1 except for the use of 3'-chloroacetophenone and phenylpiperazine as starting materials.

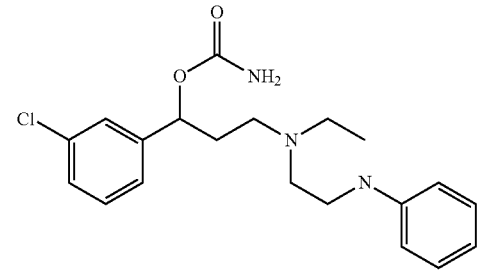 [SMILES: CCN(CCNc1ccccc1)CCC(OC(N)=O)c1cccc(Cl)c1]

¹H NMR (200 MHz, CDCl₃) d: 1.85 (m, 2H), 2.61-2.84 (m, 6H), 3.27 (m, 4H), 4.83 (br, 2H), 5.79 (t, 1H), 6.89 (m, 3H), 7.21-7.40 (m, 6H)

Example 8

Carbamic acid 1-(4-methoxy-phenyl)-3-(4-phenyl-piperazin-1-yl)-propyl ester

A title compound was prepared in the same manner as in Example 1 except for the use of 4'-methoxyacetophenone and phenylpiperazine as starting materials.

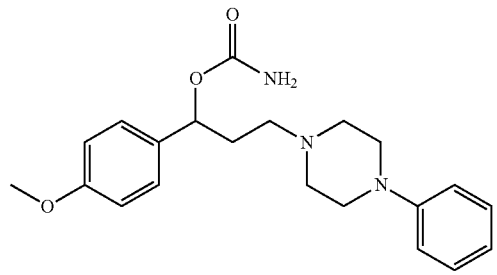 [SMILES: COc1ccc(C(CCN2CCN(c3ccccc3)CC2)OC(N)=O)cc1]

$^1$H NMR (200 MHz, CDCl$_3$) d: 2.56 (m, 2H), 2.65 (m, 4H), 2.93 (m, 2H), 3.25 (m, 4H), 3.81 (s, 3H), 4.77 (t, 1H), 5.02 (br, 2H), 6.91 (m, 5H), 7.29 (m, 4H)

Example 9

Carbamic acid 1-(4-nitro-phenyl)-3-(4-phenyl-piperazin-1-yl)-propyl ester

A title compound was prepared in the same manner as in Example 1 except for the use of 4'-nitroacetophenone and phenylpiperazine as starting materials.

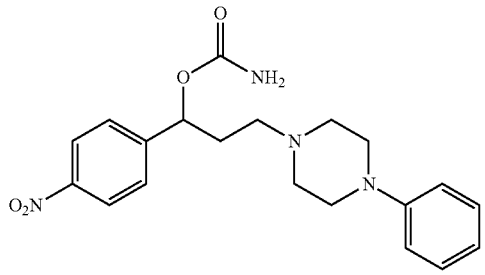 [SMILES: NC(=O)OC(CCN1CCN(c2ccccc2)CC1)c1ccc([N+](=O)[O-])cc1]

$^1$H NMR (200 MHz, CDCl$_3$) d: 2.22 (m, 2H), 3.23 (m, 6H), 3.68 (m, 2H), 3.91 (m, 2H), 5.10 (br, 2H), 5.81 (t, 1H), 6.91 (m, 2H), 7.02 (m, 2H), 7.40 (m, 2H), 7.62 (m, 2H), 8.23 (m, 2H)

Example 10

Carbamic acid 3-(4-phenyl-piperazin-1-yl)-1-p-tolyl-propyl ester

A title compound was prepared in the same manner as in Example 1 except for the use of 4'-methylacetophenone and phenylpiperazine as starting materials.

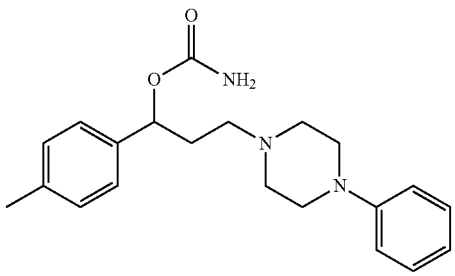 [SMILES: Cc1ccc(C(CCN2CCN(c3ccccc3)CC2)OC(N)=O)cc1]

$^1$H NMR (500 MHz, DMSO) d: 2.11 (s, 1H), 2.31 (s, 3H), 2.50 (s, 1H), 3.20 (m, 6H), 3.51 (m, 2H), 5.55 (t, 1H), 6.80 (br, 2H), 6.89 (m, 1H), 7.01 (m, 2H), 7.24 (m, 4H), 7.29 (m, 4H)

Example 11

Carbamic acid 3-[4-(2,3-dihydro-benzo[1,4]dioxin-6-yl)-piperazin-1-yl]-1-phenyl-propyl ester A title compound was prepared in the same manner as in Example 1 except for the use of acetophenone and 1-(2,3-dihydro-benzo[1,4]dioxin-6-yl-1)-piperazine as starting materials.

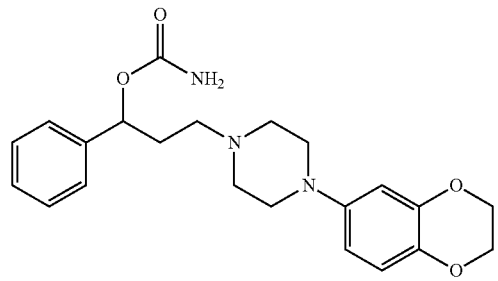 [SMILES: NC(=O)OC(CCN1CCN(c2ccc3c(c2)OCCO3)CC1)c1ccccc1]

$^1$H NMR (200 MHz, CDCl3) d: 2.03 (m, 1H), 2.21 (m, 1H), 2.42 (m, 2H), 2.55 (m, 4H), 3.05 (m, 4H), 4.20 (m, 4H), 4.80 (br, 2H), 5.82 (t, 1H), 6.45 (m, 2H), 6.84 (m, 1H), 7.32 (m, 5H)

Example 12

Carbamic acid 1-phenyl-3-[4-(4-trifluoromethoxy-phenyl)-piperazin-1-yl]-propyl ester A title compound was prepared in the same manner as in Example 1 except for the use of acetophenone and 4-trifluoromethoxy-phenylpiperazine as starting materials.

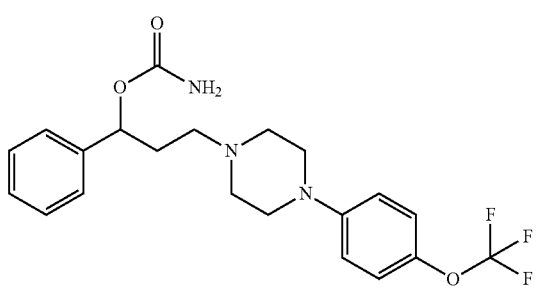 [SMILES: NC(=O)OC(CCN1CCN(c2ccc(OC(F)(F)F)cc2)CC1)c1ccccc1]

$^1$H NMR (200 MHz, CDCl$_3$) d: 2.12 (m, 2H), 2.41 (m, 2H), 2.56 (m, 4H), 3.17 (m, 4H), 4.65 (br, 2H), 5.90 (t, 1H), 6.86 (m, 2H), 7.11 (m, 2H), 7.31 (m, 5H)

Example 13

Carbamic acid 3-[4-(2,4-dimethyl-phenyl)-piperazin-1-yl]-1-phenyl-propyl ester

A title compound was prepared in the same manner as in Example 1 except for the use of acetophenone and 2,4-dimethyl-phenyl piperazine as starting materials.

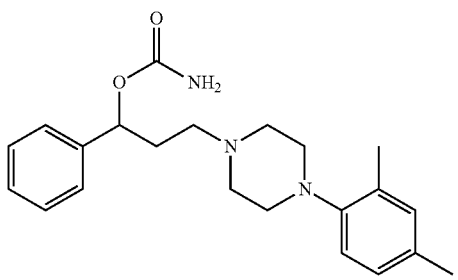

$^1$H NMR (200 MHz, CDCl$_3$) d: 1.97-2.10 (m, 1H), 2.13-2.24 (m, 1H), 2.29 (s, 3H), 2.30 (s, 3H), 2.43-2.51 (m, 2H), 2.61-2.82 (m, 4H), 2.91-2.95 (m, 4H), 4.84 (br, 2H), 5.76 (t, 1H), 6.94-7.03 (m, 3H), 7.28-7.38 (m, 5H)

Example 14

Carbamic acid 1-phenyl-3-[4-(2-trifluoromethyl-phenyl)-piperazin-1-yl]-propyl ester A title compound was prepared in the same manner as in Example 1 except for the use of acetophenone and 2-trifluoromethyl-phenyl piperazine as starting materials.

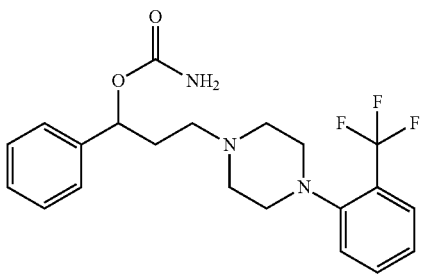 [SMILES: NC(=O)OC(CCN1CCN(c2ccccc2C(F)(F)F)CC1)c1ccccc1]

$^1$H NMR (200 MHz, Acetone) d: 2.07 (m, 2H), 2.35 (m, 2H), 2.45 (m, 4H), 2.76 (m, 4H), 5.78 (t, 1H), 6.01 (br, 2H), 7.34 (m, 5H), 7.57 (m, 4H)

Example 15

Carbamic acid 1-phenyl-3-[4-(2-chloro-phenyl)-piperazin-1-yl]-propyl ester

A title compound was prepared in the same manner as in Example 1 except for the use of acetophenone and 2-chlorophenyl piperazine as starting materials.

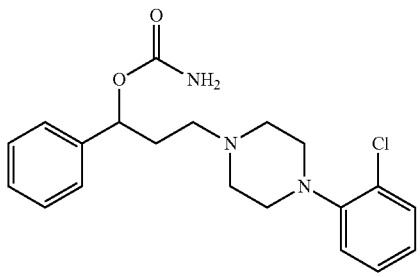 [SMILES: NC(=O)OC(CCN1CCN(c2ccccc2Cl)CC1)c1ccccc1]

$^1$H NMR (200 MHz, Acetone) d: 1.99 (m, 2H), 2.21 (m, 2H), 2.36 (m, 4H), 2.77 (m, 4H), 5.89 (t, 1H), 6.10 (br, 2H), 7.30 (m, 5H), 7.48 (m, 4H)

Example 16

Carbamic acid 1-phenyl-3-[4-(4-nitro-phenyl)-piperazin-1-yl]-propyl ester

A title compound was prepared in the same manner as in Example 1 except for the use of acetophenone and 4-nitrophenyl-piperazine as starting materials.

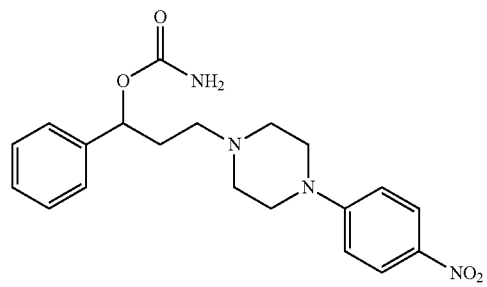 [SMILES: NC(=O)OC(CCN1CCN(c2ccc([N+](=O)[O-])cc2)CC1)c1ccccc1]

$^1$H NMR (200 MHz, CDCl3) d: 2.11 (m, 2H), 2.26 (m, 2H), 2.51 (m, 4H), 2.59 (m, 4H), 4.81 (br, 2H), 5.81 (t, 1H), 6.48 (m, 4H), 7.28 (2H), 7.42 (m, 2H)

Example 17

Carbamic acid 3-[4-(2,4-dimethoxy-phenyl)-piperazin-1-yl]-1-phenyl-propyl ester

A title compound was prepared in the same manner as in Example 1 except for the use of acetophenone and 2,4-dimethoxy-phenyl piperazine as starting materials.

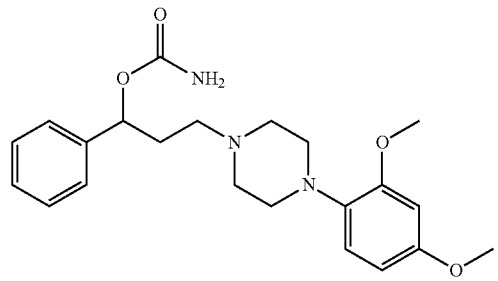 [SMILES: COc1ccc(N2CCN(CCC(OC(N)=O)c3ccccc3)CC2)c(OC)c1]

$^1$H NMR (200 MHz, CDCl$_3$) d: 2.06 (m, 1H), 2.18 (m, 1H), 2.45 (m, 3H), 2.64 (m, 4H), 3.03 (m, 4H), 3.79 (s, 3H), 3.84

(s, 3H), 3.84 (s, 3H), 4.73 (br, 2H), 5.87 (t, 1H), 6.48 (m, 2H), 6.86 (d, 1H), 7.28-7.37 (m, 5H)

Example 18

Carbamic acid 3-[4-(4-chloro-3-trifluoromethyl-phenyl)-piperazin-1-yl]-1-phenyl-propyl ester A title compound was prepared in the same manner as in Example 1 except for the use of acetophenone and 3-trifluoromethyl-4-chlorophenyl piperazine as starting materials.

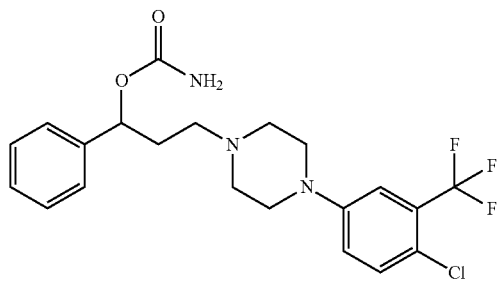 [SMILES: NC(=O)OC(CCN1CCN(c2ccc(Cl)c(C(F)(F)F)c2)CC1)c1ccccc1]

$^1$H NMR (200 MHz, CDCl3) d: 2.03 (m, 1H), 2.18 (m, 1H), 2.44 (m, 2H), 2.60 (m, 4H), 3.23 (m, 4H), 4.71 (br, 2H), 5.78 (t, 1H), 6.96 (m, 1H), 7.28-7.32 (m, 7H)

Example 19

Carbamic acid 3-[4-(2,6-dimethyl-phenyl)-piperazin-1-yl]-1-phenyl-propyl ester

A title compound was prepared in the same manner as in Example 1 except for the use of acetophenone and 2,6-dimethyl-phenyl piperazine as starting materials.

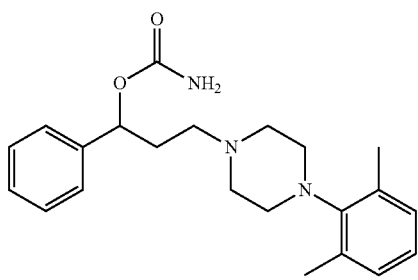 [SMILES: Cc1cccc(C)c1N1CCN(CCC(OC(N)=O)c2ccccc2)CC1]

$^1$H NMR (200 MHz, CDCl3) d: 2.05 (m, 1H), 2.18 (m, 1H), 2.27 (s, 6H), 2.41 (m, 2H), 2.55 (m, 4H), 3.13 (m, 4H), 4.70 (br, 2H), 5.77 (t, 1H), 6.97-6.99 (m, 3H), 7.28-7.39 (m, 5H)

Example 20

Carbamic acid 3-[4-(4-methoxy-phenyl)-piperazin-1-yl]-1-phenyl-propyl ester

A title compound was prepared in the same manner as in Example 1 except for the use of acetophenone and 4-methoxy-phenyl piperazine as starting materials.

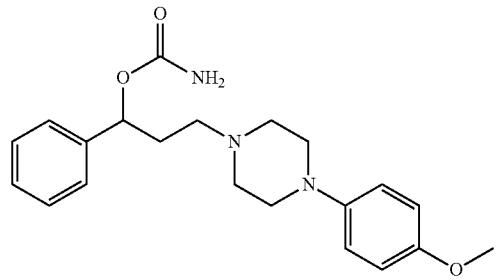 [SMILES: COc1ccc(N2CCN(CCC(OC(N)=O)c3ccccc3)CC2)cc1]

$^1$H NMR (200 MHz, CDCl$_3$) d: 2.12 (m, 1H), 2.27 (m, 1H), 2.42 (m, 2H), 2.65 (m, 4H), 3.13 (m, 4H), 3.79 (s, 3H), 4.87 (br, 2H), 5.79 (t, 1H), 6.89 (m, 4H), 7.33 (m, 5H)

Example 21

Carbamic acid 3-[4-(4-fluoro-phenyl)-piperazin-1-yl]-1-phenyl-propyl ester

A title compound was prepared in the same manner as in Example 1 except for the use of acetophenone and 4-fluorophenyl piperazine as starting materials.

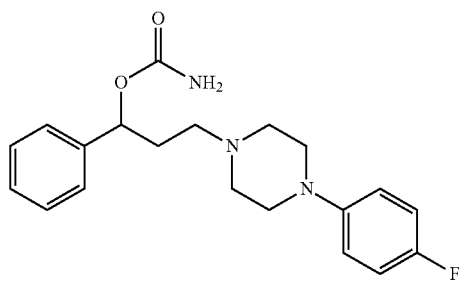 [SMILES: NC(=O)OC(CCN1CCN(c2ccc(F)cc2)CC1)c1ccccc1]

$^1$H NMR (200 MHz, CDCl$_3$) d: 2.11 (m, 1H), 2.21 (m, 1H), 2.29 (m, 2H), 2.61 (m, 4H), 3.14 (m, 4H), 4.83 (br, 2H), 5.75 (t, 1H), 6.93 (m, 4H), 7.33 (m, 5H)

Example 22

Carbamic acid 3-[4-(4-chloro-phenyl)-piperazin-1-yl]-1-phenyl-propyl ester

A title compound was prepared in the same manner as in Example 1 except for the use of acetophenone and 4-chlorophenyl piperazine as starting materials.

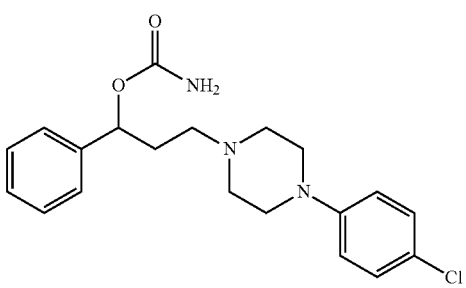 [SMILES: NC(=O)OC(CCN1CCN(c2ccc(Cl)cc2)CC1)c1ccccc1]

¹H NMR (200 MHz, CDCl3) d: 1.98 (m, 1H), 2.21 (m, 1H), 2.43 (m, 2H), 2.60 (m, 4H), 3.18 (m, 4H), 4.67 (br, 2H), 5.76 (t, 1H), 6.85 (m, 2H), 7.24 (m, 2H), 7.37 (m, 5H)

Example 23

Carbamic acid 3-[4-(2-hydroxy-phenyl)-piperazin-1-yl]-1-phenyl-propyl ester

A title compound was prepared in the same manner as in Example 1 except for the use of acetophenone and 2-hydroxy-phenyl piperazine as starting materials.

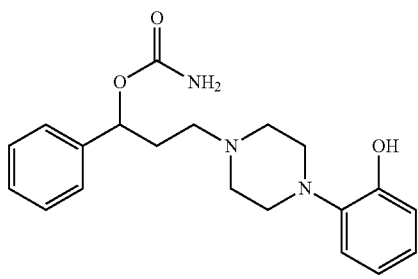 [SMILES: NC(=O)OC(CCN1CCN(c2ccccc2O)CC1)c1ccccc1]

¹H NMR (200 MHz, CDCl₃) d: 2.05 (m, 2H), 2.40 (m, 2H), 2.62 (m, 4H), 2.90 (m, 4H), 4.63 (br, 2H), 5.71 (t, 1H), 6.96 (m, 3H), 7.14 (m, 2H), 7.35 (m, 3H)

Example 24

Carbamic acid 1-phenyl-3-(4-m-tolyl piperazin-1-yl)-propyl ester

A title compound was prepared in the same manner as in Example 1 except for the use of acetophenone and 3-methyl-phenyl piperazine as starting materials.

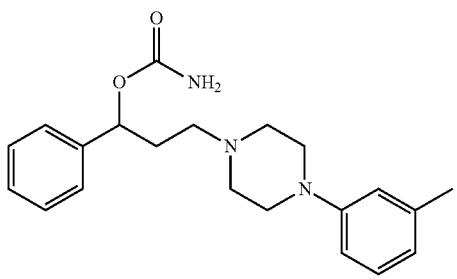 [SMILES: Cc1cccc(N2CCN(CCC(OC(N)=O)c3ccccc3)CC2)c1]

¹H NMR (200 MHz, Acetone) d: 2.07 (m, 2H), 2.28 (s, 3H), 2.39 (m, 2H), 2.55 (m, 4H), 3.17 (m, 4H), 5.81 (t, 1H), 6.61 (br, 2H), 6.78 (m, 2H), 7.10 (t, 1H), 7.31-7.40 (m, 5H)

Example 25

Carbamic acid 1-phenyl-3-(4-pyridin-2-yl-piperazin-1-yl)-propyl ester

A title compound was prepared in the same manner as in Example 1 except for the use of acetophenone and 2-pyridylpiperazine as starting materials.

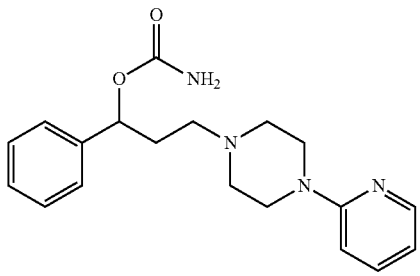 [SMILES: NC(=O)OC(CCN1CCN(c2ccccn2)CC1)c1ccccc1]

¹H NMR (200 MHz, CDCl3) d: 2.19 (m, 2H), 2.32 (m, 2H), 2.48 (m, 4H), 2.67 (m, 4H), 4.84 (br, 2H), 5.79 (t, 1H), 6.89 (m, 1H), 7.19 (m, 1H), 7.34 (m, 3H), 7.56 (m, 3H), 8.11 (m, 1H)

Example 26

Carbamic acid 3-[4-(3-methoxy-phenyl)-piperazin-1-yl]-1-phenyl-propyl ester

A title compound was prepared in the same manner as in Example 1 except for the use of acetophenone and 3-methoxy-phenyl piperazine as starting materials.

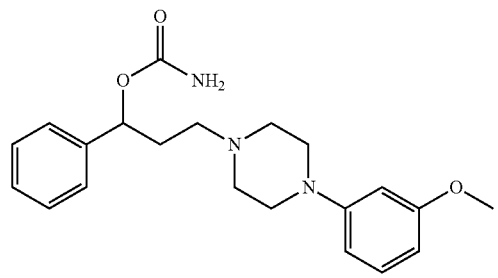 [SMILES: COc1cccc(N2CCN(CCC(OC(N)=O)c3ccccc3)CC2)c1]

¹H NMR (200 MHz, CDCl₃) d 1.97 (m, 2H), 2.39 (m, 2H), 2.55 (m, 4H), 3.18 (m, 4H), 3.77 (s, 3H), 5.76 (t, 1H), 6.1 (br, 2H), 6.43 (m, 1H), 6.53 (m, 1H), 7.12 (t, 1H), 7.30-7.43 (m, 5H)

Example 27

Carbamic acid 3-[4-(2-methoxy-phenyl)-piperazin-1-yl]-1-phenyl-propyl ester

A title compound was prepared in the same manner as in Example 1 except for the use of acetophenone and 2-methoxy-phenyl piperazine as starting materials.

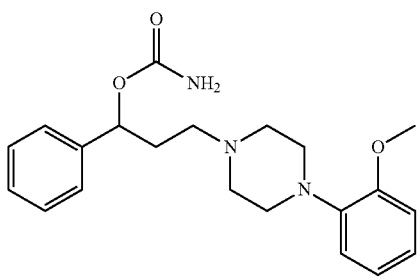 [SMILES: COc1ccccc1N1CCN(CCC(OC(N)=O)c2ccccc2)CC1]

¹H NMR (200 MHz, CDCl₃) d: 1.88 (m, 2H), 2.29 (m, 2H), 2.46 (m, 4H), 3.09 (m, 4H), 3.82 (s, 3H), 5.66 (t, 1H), 5.90 (br, 2H), 6.82 (m, 4H), 7.29 (m, 5H)

Example 28

Carbamic acid 3-[4-(3-chloro-pyridin-2-yl)-piperazin-1-yl]-1-phenyl-propyl ester A title compound was prepared in the same manner as in Example 1 except for the use of acetophenone and 1-(3-chloro-pyridin-2-yl)-piperazine as starting materials.

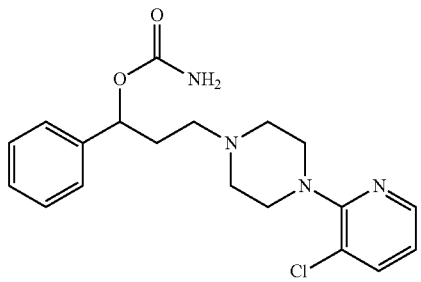 [SMILES: NC(=O)OC(CCN1CCN(c2ncccc2Cl)CC1)c1ccccc1]

¹H NMR (200 MHz, Acetone) d: 1.58 (m, 2H), 1.89 (m, 2H), 2.42 (m, 2H), 2.54 (m, 4H), 3.32 (m, 4H), 5.69 (t, 1H), 6.07 (br, 2H), 6.95 (m, 1H), 7.27-7.39 (m, 5H), 7.71 (m, 1H), 8.21 (m, 1H)

Example 29

Carbamic acid 3-[4-(3,4-dimethyl-phenyl)-piperazin-1-yl]-1-phenyl-propyl ester

A title compound was prepared in the same manner as in Example 1 except for the use of acetophenone and 3,4-dimethyl-phenyl piperazine as starting materials.

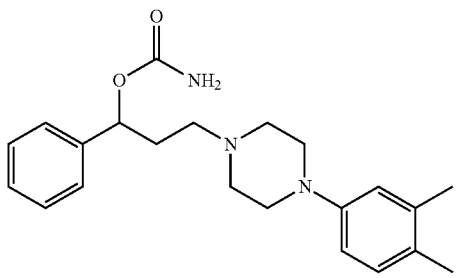 [SMILES: Cc1ccc(N2CCN(CCC(OC(N)=O)c3ccccc3)CC2)cc1C]

¹H NMR (200 MHz, CDCl3) d: 2.01 (m, 2H), 2.17 (s, 3H), 2.21 (s, 3H), 2.40 (m, 2H), 2.57 (m, 4H), 3.13 (m, 4H), 4.78 (br, 2H), 5.82 (t, 1H), 6.82 (m, 2H), 7.01 (m, 1H), 7.33 (m, 5H)

Example 30

Carbamic acid 3-(4-benzo[1,3]dioxol-5-yl-piperazin-1-yl)-1-phenyl-propyl ester

A title compound was prepared in the same manner as in Example 1 except for the use of acetophenone and 3,4-methylene dioxy-phenyl piperazine as starting materials.

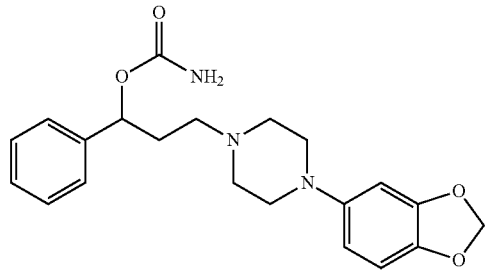 [SMILES: NC(=O)OC(CCN1CCN(c2ccc3c(c2)OCO3)CC1)c1ccccc1]

¹H NMR (200 MHz, CDCl3) d: 1.99 (m, 1H), 2.12 (m, 1H), 2.36 (m, 2H), 2.54 (m, 4H), 3.05 (m, 4H), 4.77 (br, 2H), 5.72 (t, 1H), 5.90 (s, 2H), 6.32 (dd, 1H), 6.55 (m, 1H), 6.72 (d, 1H), 7.33 (m, 5H)

Example 31

Carbamic acid 3-[4-(3,4-dichloro-phenyl)-piperazin-1-yl]-1-phenyl-propyl ester

A title compound was prepared in the same manner as in Example 1 except for the use of acetophenone and 3,4-dichloro-phenyl piperazine as starting materials.

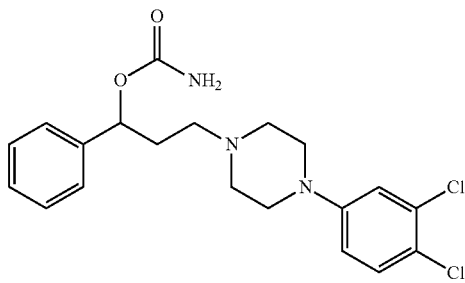 [SMILES: NC(=O)OC(CCN1CCN(c2ccc(Cl)c(Cl)c2)CC1)c1ccccc1]

¹H NMR (200 MHz, CDCl3) d: 2.10 (m, 2H), 2.39 (m, 2H), 2.54 (m, 4H), 3.15 (m, 4H), 4.62 (br, 2H), 5.85 (t, 1H), 6.81 (dd, 1H), 6.99 (m, 1H), 7.34 (m, 6H)

Example 32

Carbamic acid 3-[4-(5-chloro-2-methoxy-phenyl)-piperazin-1-yl]-1-phenyl-propyl ester A title compound was prepared in the same manner as in Example 1 except for the use of acetophenone and 5-chloro-2-methoxy-phenyl piperazine as starting materials.

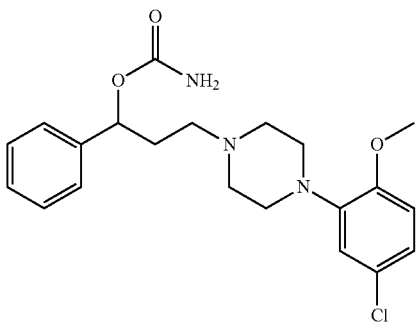 [SMILES: COc1ccc(Cl)cc1N1CCN(CCC(OC(N)=O)c2ccccc2)CC1]

¹H NMR (200 MHz, CDCl3) d: 2.04 (m, 2H), 2.41 (m, 2H), 2.61 (m, 4H), 3.06 (m, 4H), 3.82 (s, 3H), 4.62 (br, 2H), 5.82 (t, 1H), 6.71 (d, 1H), 6.99 (m, 2H), 7.34 (m, 5H)

Example 33

Carbamic acid 3-[4-(3,5-dimethoxy-phenyl)-piperazin-1-yl]-1-phenyl-propyl ester

A title compound was prepared in the same manner as in Example 1 except for the use of acetophenone and 3,5-dimethoxy-phenyl piperazine as starting materials.

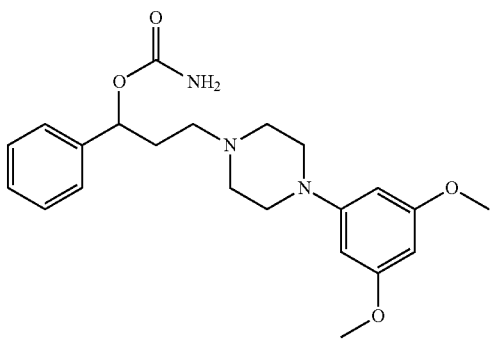 [SMILES: COc1cc(OC)cc(N2CCN(CCC(OC(N)=O)c3ccccc3)CC2)c1]

¹H NMR (200 MHz, CDCl₃) d: 1.99 (m, 2H), 2.21 (m, 1H), 2.49 (m, 2H), 2.58 (m, 4H), 3.20 (m, 4H), 3.80 (s, 3H), 4.89 (br, 2H), 5.89 (t, 1H), 6.11 (m, 1H), 6.12 (m, 2H), 7.37 (m, 5H)

Example 34

Carbamic acid 1-phenyl-3-(4-pyrimidin-2-yl-piperazin-1-yl)-propyl ester

A title compound was prepared in the same manner as in Example 1 except for the use of acetophenone and 2-piperazin-1-yl-pyrimidine as starting materials.

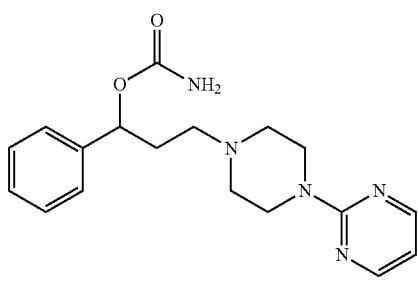 [SMILES: NC(=O)OC(CCN1CCN(c2ncccn2)CC1)c1ccccc1]

¹H NMR (200 MHz, CDCl₃) d: 2.00 (m, 2H), 2.44 (m, 6H), 3.83 (m, 4H), 4.79 (br, 2H), 5.45 (t, 1H), 6.49 (t, 1H), 7.31 (m, 5H), 8.31 (m, 2H)

Example 35

Carbamic acid 3-[4-(2-nitro-4-trifluoromethyl-phenyl)-piperazin-1-yl]-1-phenyl-propyl ester A title compound was prepared in the same manner as in Example 1 except for the use of acetophenone and 2-nitro-4-trifluoromethyl-phenyl piperazine as starting materials.

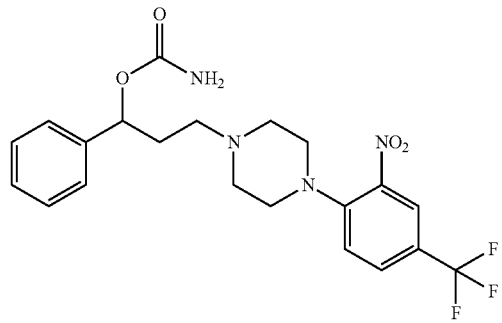 [SMILES: NC(=O)OC(CCN1CCN(c2ccc(C(F)(F)F)cc2[N+](=O)[O-])CC1)c1ccccc1]

¹H NMR (200 MHz, CDCl3) d: 2.10 (m, 2H), 2.21 (m, 2H), 2.59 (m, 4H), 3.19 (m, 4H), 4.62 (br, 2H), 5.81 (t, 1H), 7.36 (m, 5H), 7.41 (m, 1H), 7.62 (m, 1H), 8.09 (s, 1H)

Example 36

Carbamic acid 3-[4-(3-chloro-phenyl)-piperazin-1-yl]-1-phenyl-propyl ester

A title compound was prepared in the same manner as in Example 1 except for the use of acetophenone and 3-chloro-phenyl piperazine as starting materials.

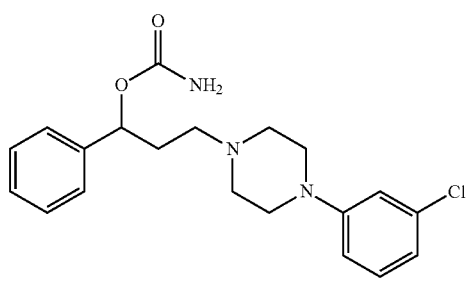 [SMILES: NC(=O)OC(CCN1CCN(c2cccc(Cl)c2)CC1)c1ccccc1]

¹H NMR (200 MHz, CDCl₃) d: 2.11 (m, 1H), 2.21 (m, 1H), 2.29 (m, 2H), 2.61 (m, 4H), 3.14 (m, 4H), 4.83 (br, 2H), 5.75 (t, 1H), 6.93 (m, 4H), 7.33 (m, 5H)

Example 37

Carbamic acid 1-phenyl-3-(4-o-tolyl piperazin-1-yl)-propyl ester

A title compound was prepared in the same manner as in Example 1 except for the use of acetophenone and 2-methyl-phenyl piperazine as starting materials.

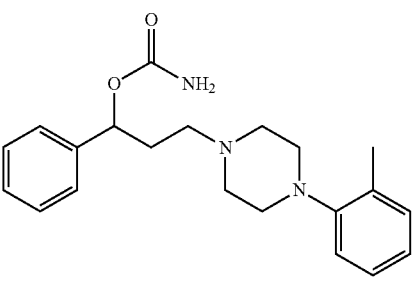 [SMILES: Cc1ccccc1N1CCN(CCC(OC(N)=O)c2ccccc2)CC1]

¹H NMR (200 MHz, Acetone) d: 2.05 (m, 2H), 2.19 (s, 3H), 2.37 (m, 2H), 2.58 (m, 4H), 2.89 (m, 4H), 5.78 (t, 1H), 6.2 (br, 2H), 6.92 (t, 1H), 7.19 (m, 3H), 7.31-7.40 (m, 5H)

Example 38

Carbamic acid 1-phenyl-3-(4-p-tolyl-piperazin-1-yl)-propyl ester

A title compound was prepared in the same manner as in Example 1 except for the use of acetophenone and 4-methyl-phenyl piperazine as starting materials.

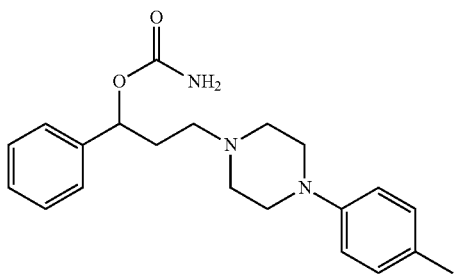 [SMILES: Cc1ccc(N2CCN(CCC(OC(N)=O)c3ccccc3)CC2)cc1]

¹H NMR (200 MHz, Acetone) d: 2.08 (m, 2H), 2.10 (s, 3H), 2.29 (m, 2H), 2.55 (m, 4H), 3.13 (m, 4H), 5.76 (t, 1H), 6.01 (br, 2H), 6.85 (m, 2H), 7.03 (m, 5H), 7.31-7.40 (m, 5H)

Example 39

Carbamic acid 1-phenyl-3-[4-(3-trifluoromethyl-phenyl)-piperazin-1-yl]-propyl ester A title compound was prepared in the same manner as in Example 1 except for the use of acetophenone and 3-trifluoromethyl-phenyl piperazine as starting materials.

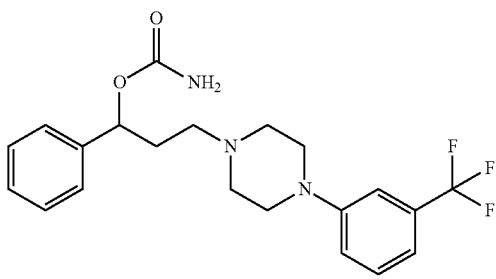 [SMILES: NC(=O)OC(CCN1CCN(c2cccc(C(F)(F)F)c2)CC1)c1ccccc1]

¹H NMR (200 MHz, Acetone) d: 2.03 (m, 2H), 2.42 (m, 2H), 2.58 (m, 4H), 3.29 (m, 4H), 5.78 (t, 1H), 6.01 (br, 2H), 7.09 (m, 1H), 7.23 (m, 2H), 7.30-7.43 (m, 6H)

Example 40

Carbamic acid 1-phenyl-3-[4-(4-trifluoromethyl-phenyl)-piperazin-1-yl]-propyl ester A title compound was prepared in the same manner as in Example 1 except for the use of acetophenone and 4-trifluoromethyl-phenyl piperazine as starting materials.

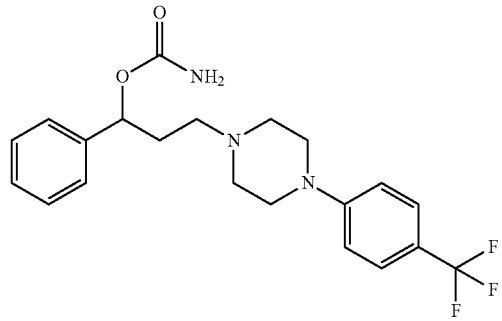 [SMILES: NC(=O)OC(CCN1CCN(c2ccc(C(F)(F)F)cc2)CC1)c1ccccc1]

¹H NMR (200 MHz, Acetone) d: 2.41 (m, 2H), 2.57 (m, 4H), 2.83 (m, 2H), 3.34 (m, 4H), 5.77 (t, 1H), 5.97 (br, 2H), 7.09 (m, 2H), 7.36 (m, 5H), 7.52 (m, 2H)

Example 41

Carbamic acid 3-[4-(2-fluoro-phenyl)-piperazin-1-yl]-1-phenyl-propyl ester

A title compound was prepared in the same manner as in Example 1 except for the use of acetophenone and 2-fluoro-phenyl piperazine as starting materials.

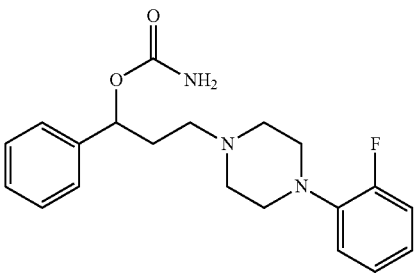 [SMILES: NC(=O)OC(CCN1CCN(c2ccccc2F)CC1)c1ccccc1]

¹H NMR (200 MHz, Acetone) d: 2.05 (m, 2H), 2.38 (m, 2H), 2.58 (m, 4H), 3.09 (m, 4H), 5.77 (t, 1H), 5.89 (br, 2H), 7.06 (m, 4H), 7.30-7.40 (m, 5H)

Example 42

Carbamic acid 3-[4-(3-fluoro-phenyl)-piperazin-1-yl]-1-phenyl-propyl ester

A title compound was prepared in the same manner as in Example 1 except for the use of acetophenone and 3-fluoro-phenyl piperazine as starting materials.

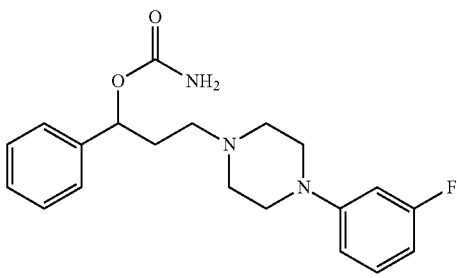 [SMILES: NC(=O)OC(CCN1CCN(c2cccc(F)c2)CC1)c1ccccc1]

¹H NMR (200 MHz, Acetone) d: 2.08 (m, 2H), 2.39 (m, 2H), 2.56 (m, 4H), 3.22 (m, 4H), 5.80 (t, 1H), 6.17 (br, 2H), 6.62 (m, 1H), 6.78 (m, 2H), 7.20-7.45 (m, 6H)

Example 43

Carbamic acid 3-[4-(2-nitro-phenyl)-piperazin-1-yl]-1-phenyl-propyl ester

A title compound was prepared in the same manner as in Example 1 except for the use of acetophenone and 2-nitro-phenyl piperazine as starting materials.

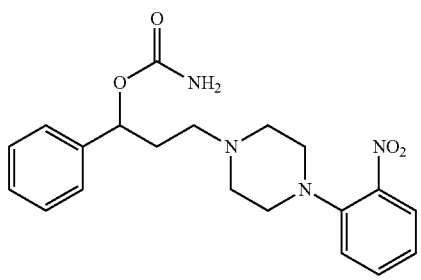

¹H NMR (200 MHz, Acetone) d: 2.05 (m, 2H), 2.40 (m, 2H), 2.44-2.62 (m, 4H), 3.07 (m, 4H), 5.77 (t, 1H), 5.98 (br, 2H), 7.32 (m, 1H), 7.57-7.76 (m, 2H)

Example 44

Carbamic acid 3-[4-(4-methoxy-phenyl)-piperazin-1-yl]-1-(4-nitro-phenyl)-propyl ester A title compound was prepared in the same manner as in Example 1 except for the use of 4'-nitro acetophenone and 4-methoxy-phenyl piperazine as starting materials.

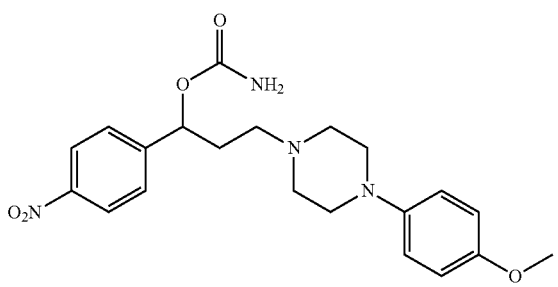 [SMILES: COc1ccc(N2CCN(CCC(OC(N)=O)c3ccc([N+](=O)[O-])cc3)CC2)cc1]

¹H NMR (200 MHz, CDCl₃) d: 1.95 (m, 1H), 2.17 (m, 1H), 2.43 (m, 2H), 2.60 (m, 4H), 3.10 (m, 4H), 3.78 (s, 3H), 4.91 (br, 2H), 5.83 (t, 1H), 6.88 (m, 4H), 7.53 (d, 2H), 8.23 (d, 2H)

Example 45

Carbamic acid 1-(3-chloro-phenyl)-3-[4-(4-methoxy-phenyl)-piperazin-1-yl]-propyl ester A title compound was prepared in the same manner as in Example 1 except for the use of 3'-chloro acetophenone and 4-methoxy-phenyl piperazine as starting materials.

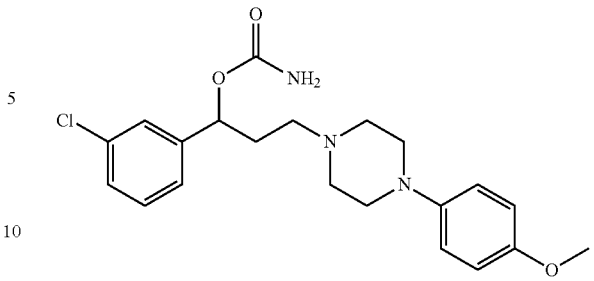

¹H NMR (200 MHz, CDCl3) d: 1.98 (m, 1H), 2.20 (m, 1H), 2.43 (m, 2H), 2.61 (m, 4H), 3.11 (m, 4H), 3.79 (s, 3H), 4.75 (br, 2H), 5.73 (t, 1H), 6.89 (m, 4H), 7.32 (m, 4H)

Example 46

Carbamic acid 1-(2-fluoro-phenyl)-3-[4-(4-methoxy-phenyl)-piperazin-1-yl]-propyl ester A title compound was prepared in the same manner as in Example 1 except for the use of 2'-fluoro acetophenone and 4-methoxy-phenyl piperazine as starting materials.

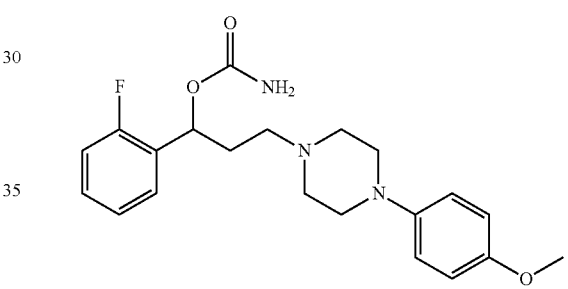

¹H NMR (200 MHz, CDCl₃) d: 1.88-2.00 (m, 2H), 2.32 (m, 2H), 2.58 (m, 4H), 3.09 (m, 4H), 3.81 (s, 3H), 4.89 (br, 2H), 5.81 (t, 1H), 6.92 (m, 4H), 7.28 (m, 5H)

Example 47

Carbamic acid 1-(4-methoxy-phenyl)-3-[4-(4-methoxy-phenyl)-piperazin-1-yl]-propyl ester A title compound was prepared in the same manner as in Example 1 except for the use of 4'-methoxy acetophenone and 4-methoxy-phenyl piperazine as starting materials.

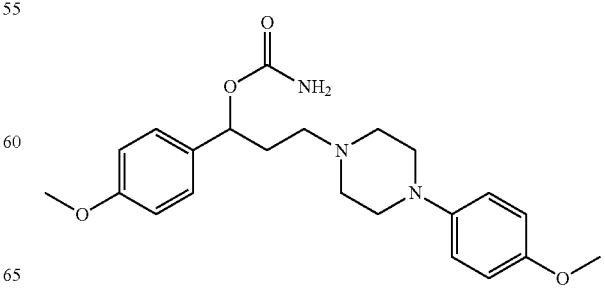

¹H NMR (200 MHz, CDCl3) d: 1.97 (m, 1H), 2.17 (m, 1H), 2.41 (m, 2H), 2.60 (m, 4H), 3.10 (m, 4H), 3.78 (s, 3H), 3.81 (s, 3H), 4.87 (br, 2H), 5.69 (t, 1H), 6.88 (m, 6H), 7.30 (m, 2H)

Example 48

Carbamic acid 1-(4-tert-butyl-phenyl-3-[4-(4-methoxy-phenyl)-piperazin-1-yl]-propyl ester A title compound was prepared in the same manner as in Example 1 except for the use of 4'-tert-butyl acetophenone and 4-methoxy-phenyl piperazine as starting materials.

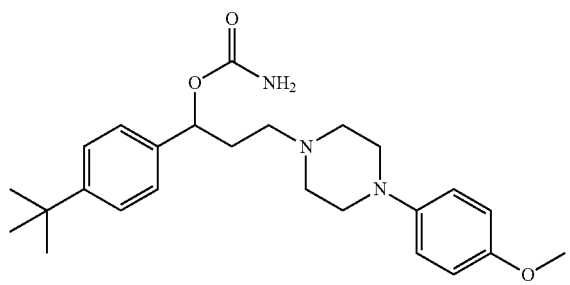 [SMILES: COc1ccc(N2CCN(CCC(OC(N)=O)c3ccc(C(C)(C)C)cc3)CC2)cc1]

¹H NMR (200 MHz, CDCl3) d: 1.32 (s, 9H), 1.94 (m, 2H), 2.68 (m, 3H), 2.80 (m, 3H), 3.27 (m, 4H), 3.78 (s, 3H), 4.95 (t, 1H), 5.82 (br, 2H), 6.90 (m, 3H), 7.24-7.38 (m, 6H)

Example 49

Carbamic acid 3-[4-(4-methoxy-phenyl)-piperazin-1-yl]-1-naphthalen-2-yl-propyl ester A title compound was prepared in the same manner as in Example 1 except for the use of 2'-acetonaphthone and 4-methoxy-phenyl piperazine as starting materials.

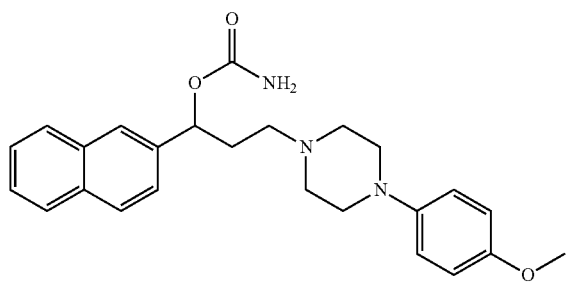 [SMILES: COc1ccc(N2CCN(CCC(OC(N)=O)c3ccc4ccccc4c3)CC2)cc1]

¹H NMR (200 MHz, CDCl₃) d: 2.08 (m, 1H), 2.43 (m, 1H), 2.47 (m, 2H), 2.55 (m, 4H), 3.12 (m, 4H), 3.79 (s, 3H), 4.7 (br, 2H), 5.93 (t, 1H), 6.89 (m, 4H), 7.51 (m, 3H), 7.86 (m, 4H)

Example 50

Carbamic acid 1-(2-chloro-phenyl)-3-[4-(4-methoxy-phenyl)-piperazin-1-yl]-propyl ester A title compound was prepared in the same manner as in Example 1 except for the use of 2'-chloroacetophenone and 4-methoxy-phenyl piperazine as starting materials.

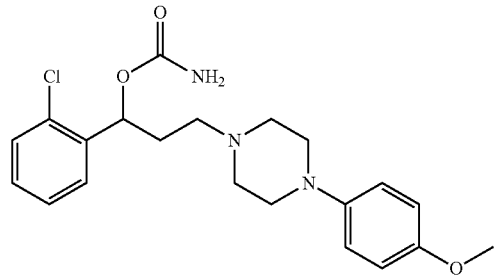

¹H NMR (200 MHz, CDCl3) d: 2.08 (m, 2H), 2.58 (m, 6H), 3.10 (m, 4H), 3.78 (s, 3H), 4.85 (br, 2H), 6.12 (t, 1H), 6.82-6.94 (m, 4H), 7.21-7.45 (m, 4H)

Example 51

Carbamic acid 3-[4-(4-methoxy-phenyl)-piperazin-1-yl]-1-(2-trifluoromethyl-phenyl)-propyl ester A title compound was prepared in the same manner as in Example 1 except for the use of 2'-trifluoromethyl acetophenone and 4-methoxy-phenyl piperazine as starting materials.

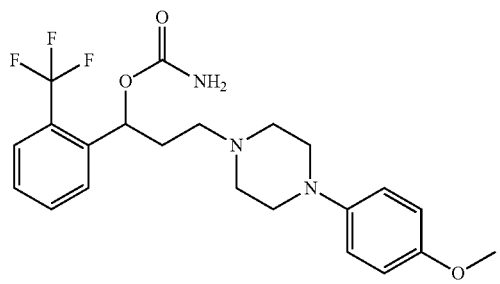 [SMILES: COc1ccc(N2CCN(CCC(OC(N)=O)c3ccccc3C(F)(F)F)CC2)cc1]

¹H NMR (200 MHz, CDCl₃) d: 2.04 (m, 2H), 2.63 (m, 6H), 3.11 (m, 4H), 3.79 (s, 3H), 4.78 (br, 2H), 6.12 (t, 1H), 6.83-6.95 (m, 4H), 7.37-7.69 (m, 4H)

Example 52

Carbamic acid 1-(3,4-difluoro-phenyl)-3-[4-(4-methoxy-phenyl)-piperazin-1-yl]-propyl ester A title compound was prepared in the same manner as in Example 1 except for the use of 3',4'-difluoromethyl acetophenone and 4-methoxy-phenyl piperazine as starting materials.

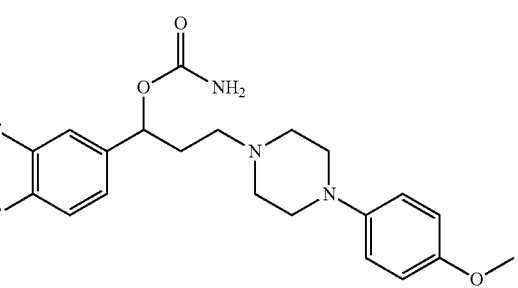

¹H NMR (200 MHz, CDCl₃) d: 1.98 (m, 1H), 2.21 (m, 1H), 2.41 (m, 2H), 2.60 (m, 4H), 3.10 (m, 4H), 3.80 (s, 3H), 4.92 (br, 2H), 5.75 (t, 1H), 6.89 (m, 4H), 7.11 (m, 3H)

Example 53

Carbamic acid 1-(3-fluoro-phenyl)-3-[4-(4-methoxy-phenyl)-piperazin-1-yl]-propyl ester A title compound was prepared in the same manner as in Example 1 except for the use of 3'-fluoro acetophenone and 4-methoxy-phenyl piperazine as starting materials.

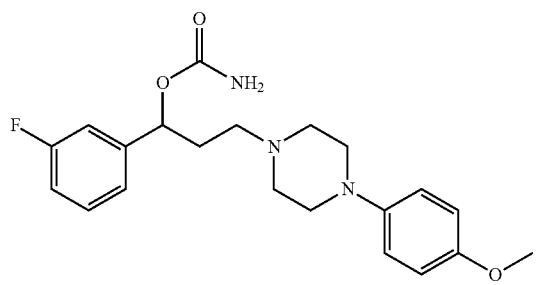 [SMILES: COc1ccc(N2CCN(CCC(OC(N)=O)c3cccc(F)c3)CC2)cc1]

¹H NMR (200 MHz, CDCl3) d: 1.99 (m, 1H), 2.19 (m, 1H), 2.43 (m, 2H), 2.60 (m, 4H), 3.11 (m, 4H), 3.78 (s, 3H), 4.88 (br, 2H), 5.74 (t, 1H), 6.91 (m, 4H), 7.10 (m, 3H), 7.33 (m, 1H)

Example 54

Carbamic acid 1-(3-methoxy-phenyl)-3-[4-(4-methoxy-phenyl)-piperazin-1-yl]-propyl ester A title compound was prepared in the same manner as in Example 1 except for the use of 3'-methoxy acetophenone and 4-methoxy-phenyl piperazine as starting materials.

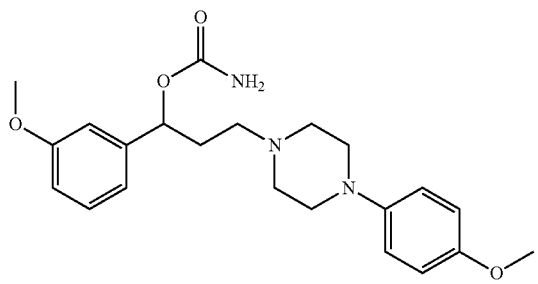 [SMILES: COc1ccc(N2CCN(CCC(OC(N)=O)c3cccc(OC)c3)CC2)cc1]

¹H NMR (200 MHz, CDCl₃) d: 1.98 (m, 1H), 2.14 (m, 1H), 2.44 (m, 2H), 2.61 (m, 4H), 3.11 (m, 4H), 3.78 (s, 3H), 3.82 (s, 3H), 4.86 (br, 2H), 5.72 (t, 1H), 6.83 (m, 7H), 7.28 (m, 1H)

Example 55

Carbamic acid 3-[4-(4-methoxy-phenyl)-piperazin-1-yl]-1-naphthalen-1-yl-propyl ester A title compound was prepared in the same manner as in Example 1 except for the use of 1'-acetonaphthone and 4-methoxy-phenyl piperazine as starting materials.

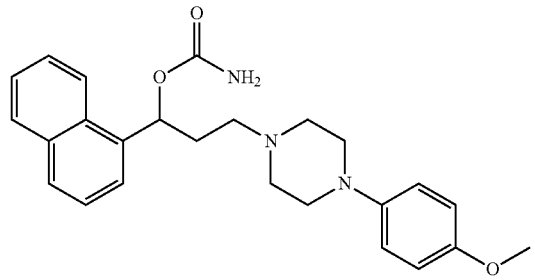 [SMILES: COc1ccc(N2CCN(CCC(OC(N)=O)c3cccc4ccccc34)CC2)cc1]

¹H NMR (200 MHz, CDCl3) d: 2.26 (m, 2H), 2.55 (m, 2H), 2.63 (m, 4H), 3.12 (m, 4H), 3.80 (s, 3H), 4.71 (br, 2H), 6.59 (t, 1H), 6.92 (m, 4H), 7.45-7.58 (m, 4H), 7.62-7.92 (m, 2H), 8.25 (d, 1H)

Example 56

Carbamic acid 3-[4-(4-methoxy-phenyl)-piperazin-1-yl]-1-p-tolyl-propyl ester

A title compound was prepared in the same manner as in Example 1 except for the use of 4'-methyl acetophenone and 4-methoxy-phenyl piperazine as starting materials.

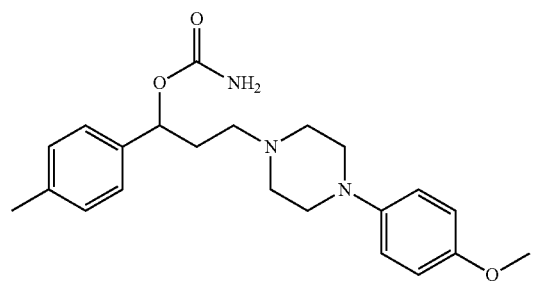

¹H NMR (200 MHz, CDCl3) d: 2.17 (m, 2H), 2.36 (s, 3H), 2.42 (m, 2H), 2.64 (m, 4H), 3.12 (m, 4H), 3.78 (s, 3H), 4.78 (br, 2H), 5.87 (t, 1H), 6.88 (m, 4H), 7.23 (m, 4H)

Example 57

Carbamic acid 3-[4-(4-methoxy-phenyl)-piperazin-1-yl]-1-m-tolyl-propyl ester

A title compound was prepared in the same manner as in Example 1 except for the use of 3'-methyl acetophenone and 4-methoxy-phenyl piperazine as starting materials.

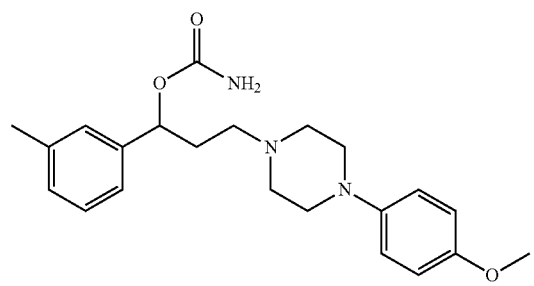

¹H NMR (200 MHz, CDCl3) d: 2.01 (m, 1H), 2.178 (m, 1H), 2.37 (s, 3H), 2.42 (m, 2H), 2.61 (m, 4H), 3.11 (m, 4H), 3.79 (s, 3H), 4.86 (br, 2H), 5.72 (t, 1), 6.89 (m, 4H), 7.18 (m, 4H)

Example 58

Carbamic acid 1-(2,4-dichloro-phenyl)-3-[4-(4-methoxy-phenyl)-piperazin-1-yl]-propyl ester A title compound was prepared in the same manner as in Example 1 except for the use of 2',4'-dichloroacetophenone and 4-methoxy-phenyl piperazine as starting materials.

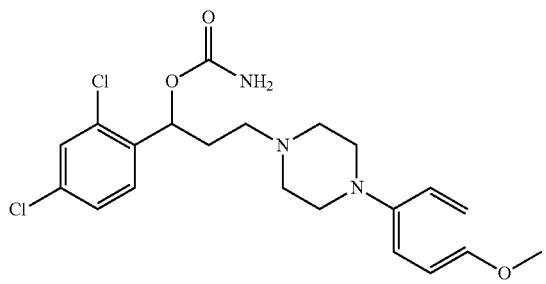 [SMILES: C=C/C(=C\C=C\OC)N1CCN(CCC(OC(N)=O)c2ccc(Cl)cc2Cl)CC1]

¹H NMR (200 MHz, CDCl3) d: 2.06 (m, 2H), 2.50 (m, 2H), 2.6 (m, 2H), 3.1 (m, 4H), 3.78 (s, 3H), 4.76 (br, 2H), 6.07 (t, 1H), 6.88 (m, 4H), 7.32 (m, 3H)

Example 59

Carbamic acid 3-[4-(4-methoxy-phenyl)-piperazin-1-yl]-1-o-tolyl-propyl ester

A title compound was prepared in the same manner as in Example 1 except for the use of 2'-methyl acetophenone and 4-methoxy-phenyl piperazine as starting materials.

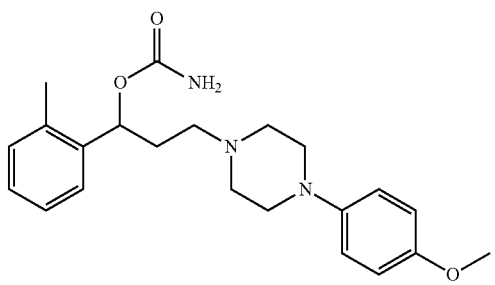 [SMILES: COc1ccc(N2CCN(CCC(OC(N)=O)c3ccccc3C)CC2)cc1]

¹H NMR (200 MHz, CDCl₃) d: 1.95-2.03 (m, 1H), 2.06-2.13 (m, 1H), 2.45 (s, 3H), 2.5-2.63 (m, 4H), 3.08-3.13 (m, 4H), 3.79 (s, 3H), 4.66 (br, 2H), 6.00 (t, 1H), 6.83-6.95 (m, 4H), 7.18-7.40 (m, 4H)

Example 60

Carbamic acid 1-(2,4-dimethyl-phenyl)-3-[4-(4-methoxy-phenyl)-piperazin-1-yl]-propyl ester A title compound was prepared in the same manner as in Example 1 except for the use of 2',4'-dimethyl acetophenone and 4-methoxy-phenyl piperazine as starting materials.

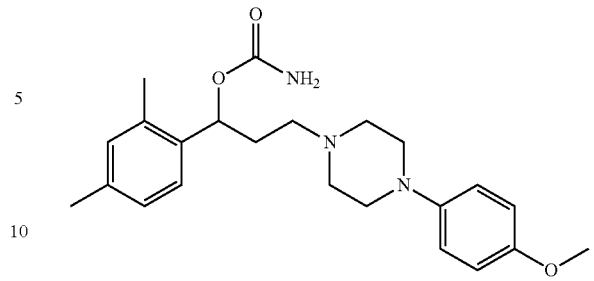

¹H NMR (200 MHz, CDCl3) d: 1.94-2.04 (m, 2H), 2.10-2.21 (m, 2H), 2.32 (s, 3H), 2.41 (s, 3H), 2.60-2.63 (m, 4H), 3.08-3.13 (m, 4H), 3.79 (s, 3H), 4.65 (br, 2H), 5.96 (t, 1H), 6.87-7.06 (m, 6H), 7.27 (d, 1H)

Example 61

Carbamic acid 1-(3,4-dimethyl-phenyl)-3-[4-(4-methoxy-phenyl)-piperazin-1-yl]-propyl ester A title compound was prepared in the same manner as in Example 1 except for the use of 3',4'-dimethyl acetophenone and 4-methoxy-phenyl piperazine as starting materials.

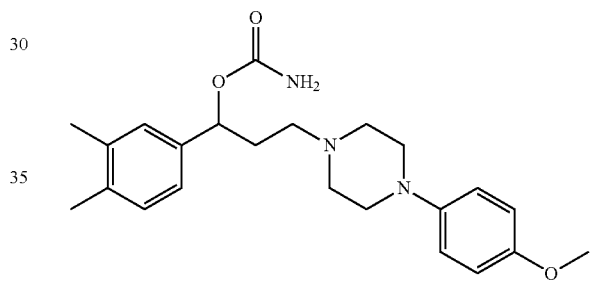

¹H NMR (200 MHz, CDCl₃) d: 2.01 (m, 1H), 2.11 (m, 1H), 2.32 (s, 3H), 2.41 (s, 3H), 2.44 (m, 2H), 2.62 (m, 4H), 3.12 (m, 4H), 3.80 (s, 3H), 4.65 (br, 2H), 5.69 (t, 1H), 6.91 (m, 4H), 7.14 (m, 3H)

Example 62

Carbamic acid 1-(2,5-dimethyl-phenyl)-3-[4-(4-methoxy-phenyl)-piperazin-1-yl]-propyl ester A title compound was prepared in the same manner as in Example 1 except for the use of 2',5'-dimethyl acetophenone and 4-methoxy-phenyl piperazine as starting materials.

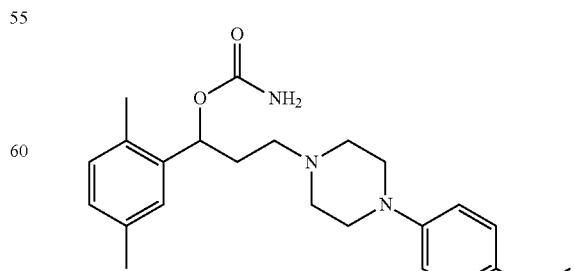

¹H NMR (200 MHz, CDCl3) d: 1.99 (m, 2H), 2.09 (m, 2H), 2.54 (m, 3H), 3.10 (m, 4H), 3.80 (s, 3H), 4.75 (br, 2H), 5.96 (t, 1H), 6.88 (m, 4H), 7.03 (dd, 2H), 7.18 (s, 1H)

Example 63

Carbamic acid 1-(4-chloro-3-trifluoromethyl-phenyl)-3-[4-(4-methoxy-phenyl)-piperazin-1-yl]-propyl ester A title compound was prepared in the same manner as in Example 1 except for the use of 4'-chloro-3'-trifluoromethyl acetophenone and 4-methoxy-phenyl piperazine as starting materials.

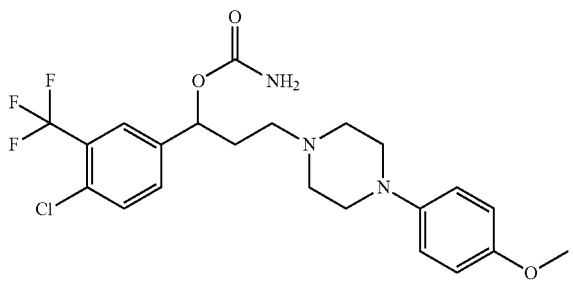 [SMILES: COc1ccc(N2CCN(CCC(OC(N)=O)c3ccc(Cl)c(C(F)(F)F)c3)CC2)cc1]

¹H NMR (200 MHz, CDCl3) d: 1.93 (m, 1H), 2.22 (m, 1H), 2.39 (m, 2H), 2.63 (m, 4H), 3.11 (m, 4H), 3.79 (s, 3H), 4.89 (br, 2H), 5.77 (t, 1H), 6.89 (m, 4H), 7.52 (m, 4H)

Example 64

Carbamic acid 3-[4-(4-methoxy-phenyl)-piperazin-1-yl]-1-(2-nitro-phenyl)-propyl ester A title compound was prepared in the same manner as in Example 1 except for the use of 2'-nitroacetophenone and 4-methoxy-phenyl piperazine as starting materials.

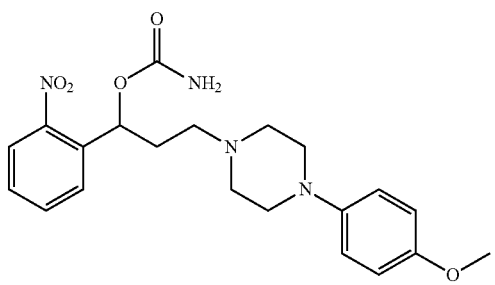 [SMILES: COc1ccc(N2CCN(CCC(OC(N)=O)c3ccccc3[N+](=O)[O-])CC2)cc1]

¹H NMR (200 MHz, CDCl₃) d: 2.07 (m, 2H), 2.62 (m, 6H), 3.09 (m, 4H), 3.78 (s, 3H), 4.80 (br, 2H), 6.27 (t, 1H), 6.88 (m, 4H), 7.45 (m, 1H), 7.64 (d, 2H), 7.98 (d, 1H)

Example 65

Carbamic acid 3-[4-(4-methoxy-phenyl)-piperazin-1-yl]-1-(3-nitro-phenyl)-propyl ester A title compound was prepared in the same manner as in Example 1 except for the use of 3'-nitroacetophenone and 4-methoxy-phenyl piperazine as starting materials.

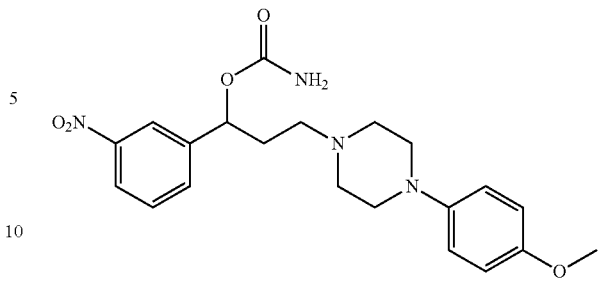

¹H NMR (200 MHz, CDCl3) d: 1.98 (m, 2H), 2.42-2.65 (m, 6H), 3.11 (m, 4H), 3.80 (s, 3H), 5.01 (br, 2H), 6.22 (t, 1H), 6.78 (m, 4H), 7.37 (m, 1H), 7.8 (d, 2H), 7.98 (d, 1H)

Example 66

Carbamic acid 3-[4-(4-methoxy-phenyl)-piperazin-1-yl]-1-(4-trifluoromethyl-phenyl)-propyl ester A title compound was prepared in the same manner as in Example 1 except for the use of 4'-trifluoromethyl acetophenone and 4-methoxy-phenyl piperazine as starting materials.

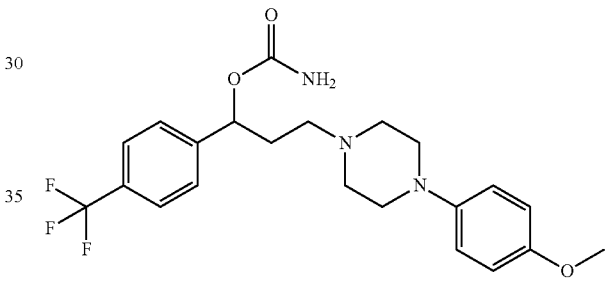

¹H NMR (200 MHz, CDCl₃) d: 1.97 (m, 1H), 2.20 (m, 1H), 2.44 (m, 2H), 2.61 (m, 4H), 3.15 (m, 4H), 3.79 (s, 3H), 4.73 (br, 2H), 5.80 (t, 1H), 6.89 (m, 4H), 7.42 (d, 2H), 7.64 (d, 2H)

Example 67

Carbamic acid 1-benzo1,3]dioxol-5-yl-3-[4-(4-methoxy-phenyl)-piperazin-1-yl]-propyl ester A title compound was prepared in the same manner as in Example 1 except for the use of 3',4'-methylenedioxy acetophenone and 4-methoxy-phenyl piperazine as starting materials.

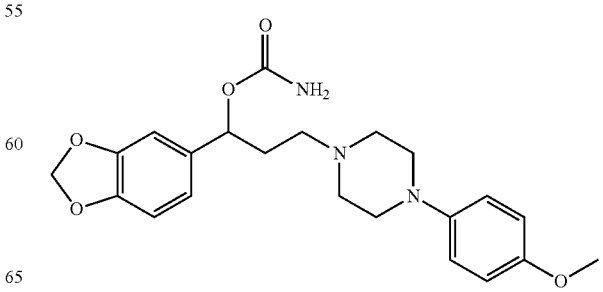

¹H NMR (200 MHz, CDCl₃) d: 1.19 (m, 1H), 2.19 (m, 1H), 2.39 (m, 2H), 2.60 (m, 4H), 3.11 (m, 4H), 3.78 (s, 3H), 4.75 (br, 2H), 5.65 (t, 1H), 5.97 (s, 2H), 6.76-6.94 (m, 7H)

Example 68

Carbamic acid 3-[4-(4-methoxy-phenyl)-piperazin-1-yl]-1-(3-trifluoromethyl-phenyl)-propyl ester A title compound was prepared in the same manner as in Example 1 except for the use of 3'-trifluoromethyl acetophenone and 4-methoxy-phenyl piperazine as starting materials.

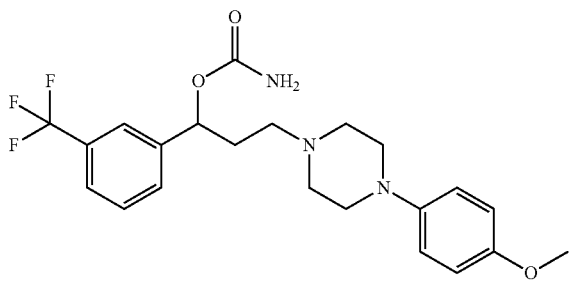 [SMILES: COc1ccc(N2CCN(CCC(OC(N)=O)c3cccc(C(F)(F)F)c3)CC2)cc1]

¹H NMR (200 MHz, CDCl₃) d: 1.99 (m, 1H), 2.22 (m, 1H), 2.39 (m, 2H), 2.61 (m, 4H), 3.11 (m, 4H), 3.79 (s, 3H), 4.77 (br, 2H) 5.82 (t, 1H), 6.89 (m, 4H), 7.56 (m, 4H)

Example 69

Carbamic acid 1-(2-fluoro-phenyl)-3-[4-(4-methoxy-phenyl)-piperazin-1-yl]-propyl ester A title compound was prepared in the same manner as in Example 1 except for the use of 2'-fluoroacetophenone and 4-methoxy-phenyl piperazine as starting materials.

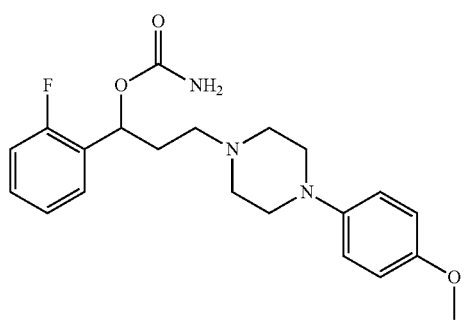 [SMILES: COc1ccc(N2CCN(CCC(OC(N)=O)c3ccccc3F)CC2)cc1]

¹H NMR (200 MHz, CDCl₃) d: 2.14 (m, 2H), 2.49 (m, 2H), 2.61 (m, 4H), 3.09 (m, 4H), 3.79 (s, 3H), 4.91 (br, 2H), 6.02 (t, 1H), 6.91 (m, 4H), 7.14 (m, 2H), 7.36 (m, 2H)

Example 70

Carbamic acid 1-(3,4-dichloro-phenyl)-3-[4-(4-methoxy-phenyl)-piperazin-1-yl]-propyl ester A title compound was prepared in the same manner as in Example 1 except for the use of 3',4'-dichloro acetophenone and 4-methoxy-phenyl piperazine as starting materials.

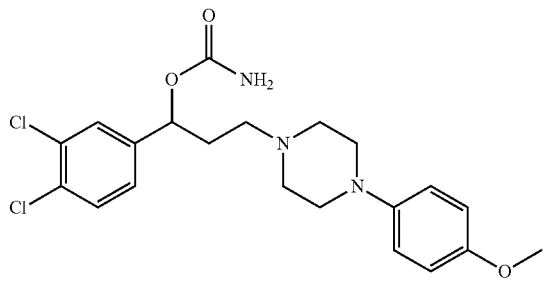 [SMILES: COc1ccc(N2CCN(CCC(OC(N)=O)c3ccc(Cl)c(Cl)c3)CC2)cc1]

¹H NMR (200 MHz, CDCl3) d: 2.11 (m, 2H), 2.17 (m, 2H), 2.68 (m, 4H), 3.15 (m, 4H), 3.72 (s, 3H), 4.81 (br, 2H), 5.90 (t, 1H), 6.92 (m, 4H), 7.12 (m, 1H), 7.28 (m, 2H)

Example 71

Carbamic acid 1-(4-chloro-phenyl)-3-[4-(4-methoxy-phenyl)-piperazin-1-yl]-propyl ester A title compound was prepared in the same manner as in Example 1 except for the use of 4'-dichloro acetophenone and 4-methoxy-phenyl piperazine as starting materials.

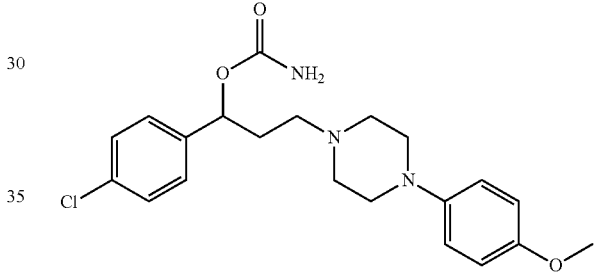

¹H NMR (200 MHz, CDCl3) d: 1.98 (m, 1H), 2.17 (m, 1H), 2.42 (m, 2H), 2.61 (m, 4H), 3.11 (m, 4H), 3.80 (s, 3H), 4.83 (br, 2H), 5.87 (t, 1H), 6.89 (m, 4H), 7.32 (m, 4H)

Example 72

Carbamic acid 1-(4-chloro-3-trifluoromethyl-phenyl)-3-[4-(4-hydroxy-phenyl)-piperazin-1-yl]-propyl ester A title compound was prepared in the same manner as in Example 1 except for the use of 4'-chloro-3'-trifluoromethyl acetophenone and 4-hydroxy-phenyl piperazine as starting materials.

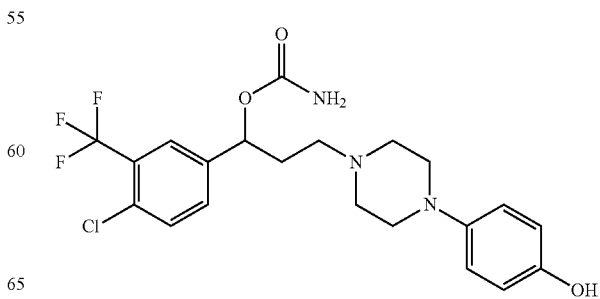

¹H NMR (200 MHz, CDCl3) d: 2.01 (m, 1H), 2.21 (m, 1H), 2.53 (m, 2H), 2.71 (m, 4H), 4.92 (br, 2H), 5.82 (t, 1H), 6.80 (m, 4H), 7.49 (m, 2H), 7.70 (s, 1H)

Example 73

Carbamic acid 1-(3,4-dichloro-phenyl)-3-[4-(4-hydroxy-phenyl)-piperazin-1-yl]-propyl ester A title compound was prepared in the same manner as in Example 1 except for the use of 3',4'-dichloroacetophenone and 4-hydroxy-phenyl piperazine as starting materials.

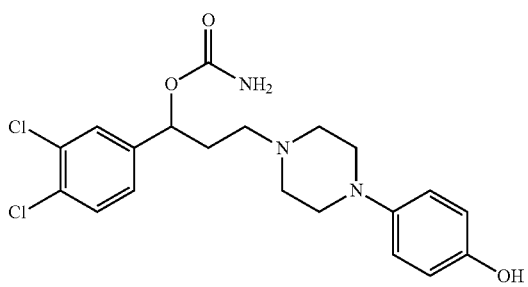 [SMILES: NC(=O)OC(CCN1CCN(c2ccc(O)cc2)CC1)c1ccc(Cl)c(Cl)c1]

¹H NMR (200 MHz, CDCl3) d: 2.08 (m, 2H), 2.16 (m, 2H), 2.65 (m, 4H), 3.11 (m, 4H), 4.75 (br, 2H), 5.83 (t, 1H), 6.82 (m, 4H), 7.29 (m, 1H), 7.43 (m, 2H)

Example 74

Carbamic acid 3-[4-(2-ethoxy-phenyl)-piperazin-1-yl]-1-(4-fluoro-phenyl)-propyl ester A title compound was prepared in the same manner as in Example 1 except for the use of 4'-fluoro acetophenone and 2-ethoxy-phenyl piperazine as starting materials.

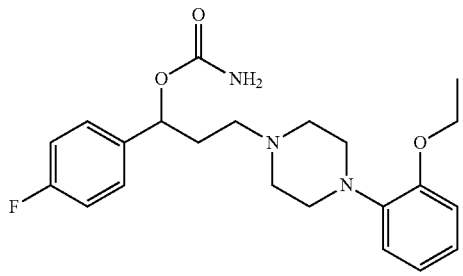 [SMILES: CCOc1ccccc1N1CCN(CCC(OC(N)=O)c2ccc(F)cc2)CC1]

¹H NMR (200 MHz, CDCl3) d: 1.43 (m, 3H), 2.18 (m, 2H), 2.55-3.05 (m, 10H), 4.11 (m, 2H), 5.76 (t, 1H), 5.99 (br, 2H), 7.08 (m, 3H), 7.13 (m, 3H), 7.44 (m, 2H)

Example 75

Carbamic acid 3-[4-(5-chloro-2-methoxy-phenyl)-piperazin-1-yl]-1-(4-fluoro-phenyl)-propyl ester A title compound was prepared in the same manner as in Example 1 except for the use of 4'-fluoro acetophenone and 5-chloro-2-methoxy phenyl piperazine as starting materials.

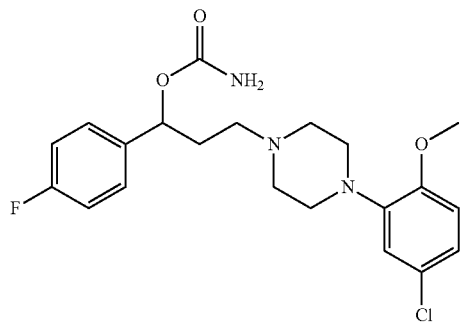 [SMILES: COc1ccc(Cl)cc1N1CCN(CCC(OC(N)=O)c2ccc(F)cc2)CC1]

¹H NMR (200 MHz, CDCl3) d: 2.38 (m, 2H), 2.54 (m, 6H), 3.04 (m, 4H), 3.86 (s, 3H), 5.73 (t, 1H), 5.93 (br, 2H), 6.93 (m, 4H), 7.16 (m, 2H), 7.51 (m, 1H)

Example 76

Carbamic acid 3-[4-(3,4-dichloro-phenyl)-piperazin-1-yl]-1-(4-fluoro-phenyl)-propyl ester A title compound was prepared in the same manner as in Example 1 except for the use of 4'-fluoro acetophenone and 3,4-dichloro phenyl piperazine as starting materials.

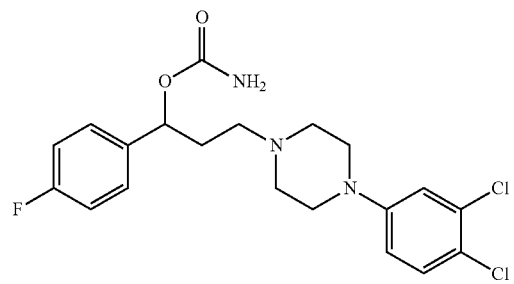 [SMILES: NC(=O)OC(CCN1CCN(c2ccc(Cl)c(Cl)c2)CC1)c1ccc(F)cc1]

¹H NMR (200 MHz, CDCl3) d: 2.22 (m, 1H), 2.48 (m, 3H), 2.54 (m, 6H), 3.24 (m, 2H), 5.72 (t, 1H), 5.97 (br, 2H), 6.91 (m, 1H), 7.08 (m, 3H), 7.45 (m, 3H)

Example 77

Carbamic acid 1-(4-fluoro-phenyl)-3-[4-(4-methoxy-phenyl)-piperazin-1-yl]-propyl ester A title compound was prepared in the same manner as in Example 1 except for the use of 4'-fluoro acetophenone and 4-methoxy phenyl piperazine as starting materials.

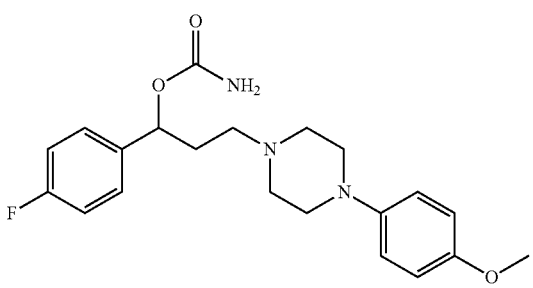 [SMILES: COc1ccc(N2CCN(CCC(OC(N)=O)c3ccc(F)cc3)CC2)cc1]

¹H NMR (200 MHz, CDCl3) d: 1.89 (m, 1H), 2.15 (m, 1H), 2.42 (m, 2H), 2.58 (m, 4H), 3.07 (m, 4H), 3.76 (s, 3H), 4.93 (br, 2H), 5.82 (t, 1H), 6.86 (m, 4H), 7.02 (m, 2H), 7.39 (m, 2H)

Example 78

Carbamic acid 1-(4-fluoro-phenyl)-3-[4-(2-methoxy-phenyl)-piperazin-1-yl]-propyl ester A title compound was prepared in the same manner as in Example 1 except for the use of 4'-fluoro acetophenone and 2-methoxy phenyl piperazine as starting materials.

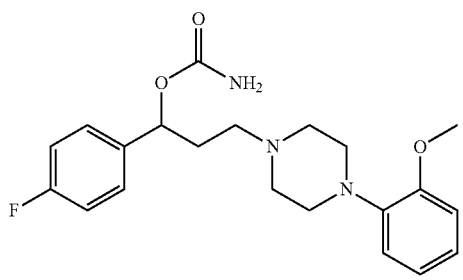 [SMILES: COc1ccccc1N1CCN(CCC(OC(N)=O)c2ccc(F)cc2)CC1]

¹H NMR (200 MHz, CDCl₃) d: 1.99 (m, 1H), 2.20 (m, 1H), 2.43 (m, 2H), 2.97 (m, 4H), 3.11 (m, 4H), 3.87 (s, 3H), 4.62 (br, 2H), 5.87 (t, 1H), 6.89-7.09 (m, 6H), 7.35 (m, 2H)

Example 79

Carbamic acid 1-(4-fluoro-phenyl)-3-[4-(4-nitro-phenyl)-piperazin-1-yl]-propyl ester A title compound was prepared in the same manner as in Example 1 except for the use of 4'-fluoro acetophenone and 4-nitro phenyl piperazine as starting materials.

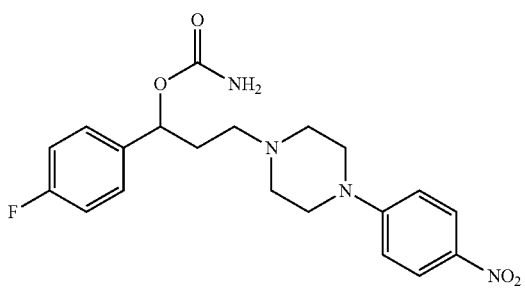 [SMILES: NC(=O)OC(CCN1CCN(c2ccc([N+](=O)[O-])cc2)CC1)c1ccc(F)cc1]

¹H NMR (200 MHz, CDCl3) d: 2.07 (m, 1H), 2.17 (m, 1H), 2.65 (m, 4H), 3.49 (m, 4H), 4.65 (br, 2H), 5.75 (t, 1H), 6.83 (m, 2H), 6.98 (m, 2H), 7.35 (m, 2H), 8.18 (m, 2H)

Example 80

Carbamic acid 1-(4-fluoro-phenyl)-3-(4-o-tolyl-piperazin-1-yl)-propyl ester

A title compound was prepared in the same manner as in Example 1 except for the use of 4'-fluoro acetophenone and 2-methyl phenyl piperazine as starting materials.

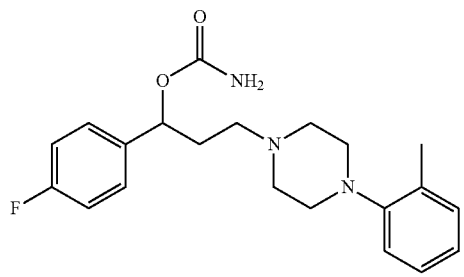 [SMILES: Cc1ccccc1N1CCN(CCC(OC(N)=O)c2ccc(F)cc2)CC1]

¹H NMR (200 MHz, CDCl3) d: 2.01 (m, 2H), 2.17 (m, 2H), 2.31 (s, 3H), 2.43 (m, 2H), 2.63 (m, 4H), 2.69 (m, 4H), 4.77 (br, 2H), 5.76 (t, 1H), 7.09 (m, 4H), 7.23 (m, 2H), 7.36 (m, 3H)

Example 81

Carbamic acid 1-(4-fluoro-phenyl)-3-[4-(4-fluoro-phenyl)-piperazin-1-yl]-propyl ester A title compound was prepared in the same manner as in Example 1 except for the use of 4'-fluoro acetophenone and 4-fluoro phenyl piperazine as starting materials.

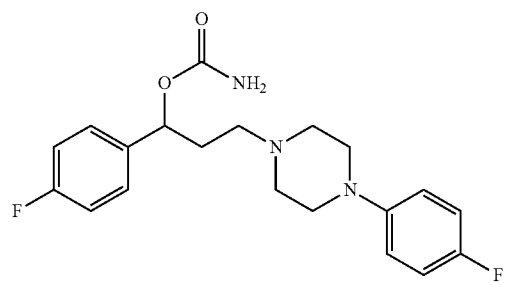 [SMILES: NC(=O)OC(CCN1CCN(c2ccc(F)cc2)CC1)c1ccc(F)cc1]

¹H NMR (200 MHz, CDCl3) d: 1.89 (m, 1H), 2.21 (m, 1H), 2.39 (m, 2H), 2.59 (m, 4H), 3.14 (m, 4H), 4.82 (br, 2H), 5.80 (t, 1H), 6.89-7.09 (m, 5H), 7.24 (m, 3H)

Example 82

Carbamic acid 2-[4-(4-methoxy-phenyl)-piperazin-1-ylmethyl]-1,2,3,4-tetrahydro-naphthalen-1-yl ester A title compound was prepared in the same manner as in Example 1 except for the use of α-tetralone and 4-methoxy phenyl piperazine as starting materials.

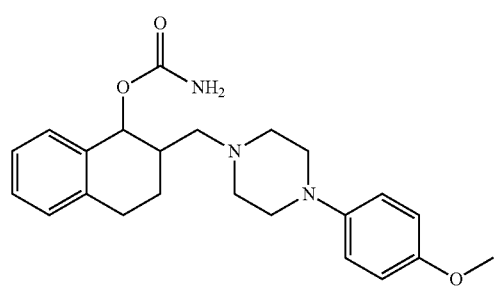 [SMILES: COc1ccc(N2CCN(CC3CCc4ccccc4C3OC(N)=O)CC2)cc1]

¹H NMR (200 MHz, CDCl3) d: 1.91 (m, 3H), 2.52 (m, 2H), 2.67 (m, 4H), 2.80 (m, 2H), 3.15 (m, 4H), 3.78 (s, 3H), 4.66 (br, 2H), 6.05 (t, 1H), 6.90 (m, 4H), 7.28 (m, 4H)

Example 83

Carbamic acid 1-(4-chloro-phenyl)-3-[4-(2-methoxy-phenyl)-piperazin-1-yl]-propyl ester A title compound was prepared in the same manner as in Example 1 except for the use of 4'-chloro acetophenone and 2-methoxy phenyl piperazine as starting materials.

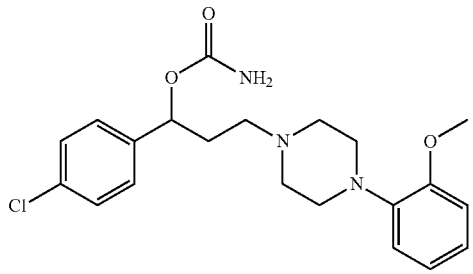 [SMILES: COc1ccccc1N1CCN(CCC(OC(N)=O)c2ccc(Cl)cc2)CC1]

¹H NMR (200 MHz, CDCl3) d: 2.28 (m, 2H), 2.39 (m, 2H), 3.09 (m, 4H), 3.23 (m, 4H), 3.70 (s, 3H), 4.99 (br, 2H), 5.88 (t, 1H), 7.11 (m, 4H), 7.31 (m, 4H)

Example 84

Carbamic acid 3-[4-(4-hydroxy-phenyl)-piperazin-1-yl]-1-phenyl-propyl ester

A title compound was prepared in the same manner as in Example 1 except for the use of acetophenone and 4-hydroxy phenyl piperazine as starting materials.

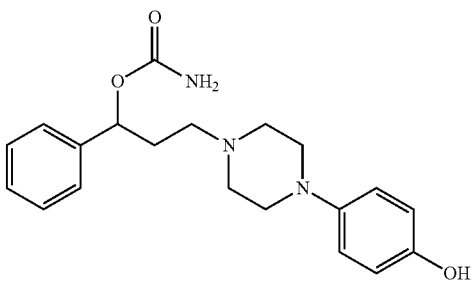 [SMILES: NC(=O)OC(CCN1CCN(c2ccc(O)cc2)CC1)c1ccccc1]

¹H NMR (200 MHz, CDCl₃) d: 1.99 (m, 2H), 2.14 (m, 2H), 2.58 (m, 4H), 3.12 (m, 4H), 5.12 (br, 2H), 5.78 (t, 1H), 6.99 (m, 4H), 7.21 (m, 5H)

Example 85

Carbamic acid 3-[4-(4-benzyloxyphenyl)-piperazin-1-yl]-1-phenyl-propyl ester

The compound 'carbamic acid 3-[4-(4-hydroxy-phenyl)-piperazin-1-yl]-1-phenyl-propyl ester (2 mmol) prepared in Example 84 was dissolved in tetrahydrofuran (25 mL), and potassium carbonate (K₂CO₃, 2.4 mmol) and benzylbromide (2.4 mmol) were added thereto, and the resulting mixture was stirred at 70° C. for 10 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

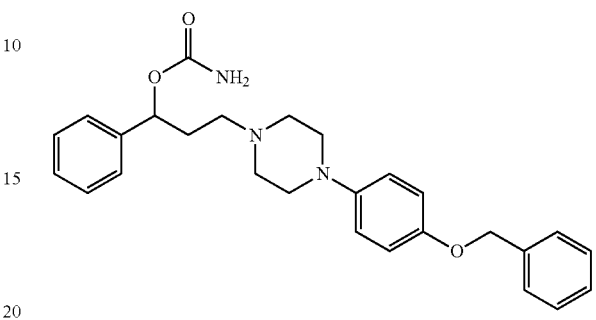

¹H NMR (200 MHz, CDCl3) d: 2.05 (m, 1H), 2.17 (m, 1H), 2.37 (m, 2H), 2.65 (m, 4H), 3.14 (m, 4H), 4.65 (br, 2H), 5.04 (s, 2H), 5.87 (t, 1H), 7.29-7.43 (m, 9H)

Example 86

Acetic acid 4-[4-(3-carbamoyloxy-3-phenyl-propyl)-piperazin-1-yl]-phenyl ester

The compound 'carbamic acid 3-[4-(4-hydroxy-phenyl)-piperazin-1-yl]-1-phenyl-propyl ester (2 mmol) prepared in Example 84 was dissolved in tetrahydrofuran (25 mL), and triethylamine (2.4 mmol) and acetylchloride (2.4 mmol) were added thereto, and the resulting mixture was stirred at a room temperature for 5 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

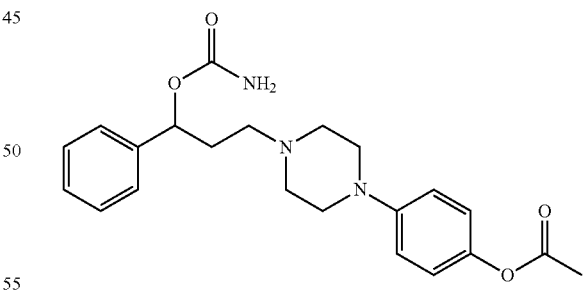

¹H NMR (200 MHz, CDCl₃) d: 2.04 (m, 1H), 2.17 (m, 1H), 2.29 (s, 3H), 2.43 (m, 2H), 2.61 (m, 4H), 3.19 (m, 4H), 4.74 (br, 2H), 5.75 (t, 1H), 6.95 (m, 4H), 7.33 (m, 5H)

Example 87

Carbamic acid 3-[4-(4-cyclopentyloxy-phenyl)-piperazin-1-yl]-1-phenyl-propyl ester The compound 'carbamic acid 3-[4-(4-hydroxy-phenyl)-piperazin-1-yl]-1-phenyl-propyl ester (2 mmol) prepared in Example 84 was dissolved in tetrahydrofuran (25 mL), and triethylamine (2.4 mmol) and bromopentyl (2.4 mmol) were added thereto, and the resulting mixture was stirred at 80? for 10 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

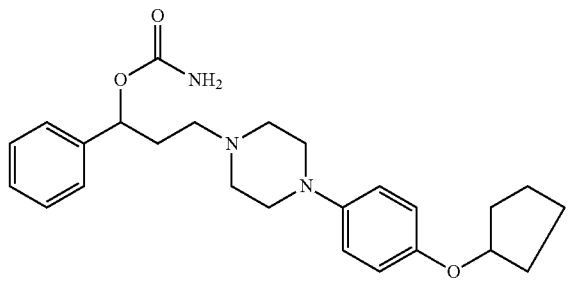 [SMILES: NC(=O)OC(CCN1CCN(c2ccc(OC3CCCC3)cc2)CC1)c1ccccc1]

$^1$H NMR (200 MHz, CDCl$_3$) d: 1.61 (m, 3H), 1.85 (m, 8H), 2.11 (m, 1H), 2.27 (m, 1H), 2.62 (m, 4H), 3.11 (m, 4H), 4.76 (br, 2H), 5.78 (t, 1H), 6.85 (m, 4H), 7.34 (m, 5H)

Example 88

Carbamic acid 1-(4-fluoro-phenyl)-3-[4-(4-hydroxy-phenyl)-piperazin-1-yl]-propyl ester A title compound was prepared in the same manner as in Example 1 except for the use of 4'-fluoro acetophenone and 4-hydroxy phenyl piperazine as starting materials.

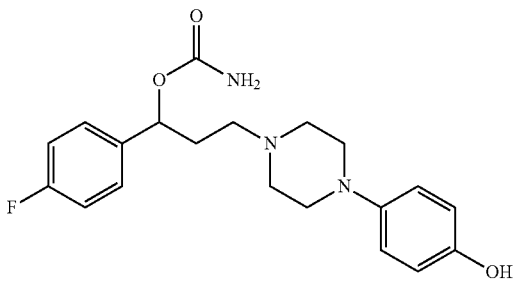 [SMILES: NC(=O)OC(CCN1CCN(c2ccc(O)cc2)CC1)c1ccc(F)cc1]

$^1$H NMR (200 MHz, CDCl3) d: 1.97 (m, 1H), 2.12 (m, 1H), 2.40 (m, 2H), 2.62 (m, 4H), 3.08 (m, 4H), 4.78 (br, 2H), 5.82 (t, 1H), 7.07 (m, 5H), 7.23 (m, 3H)

Example 89

1-(4-fluorophenyl)-3-(4-(4-(pivaloyloxy)phenyl)piperazin-1-yl)propyl carbamate

The compound 'carbamic acid 1-(4-fluoro-phenyl)-3-[4-(4-hydroxy-phenyl)-piperazin-1-yl]-propyl ester (2 mmol) prepared in Example 88 was dissolved in acetone (15 mL), and triethylamine (2.4 mmol) was added and trimethyl acetylchloride (2.4 mmol) was added dropwise, and the resulting mixture was then stirred at a room temperature for 5 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

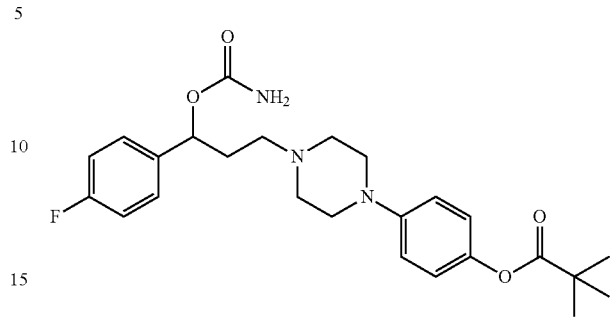

$^1$H NMR (200 MHz, CDCl3) d: 1.35 (m, 9H), 1.97 (m, 1H), 2.21 (m, 1H), 2.42 (m, 2H), 2.64 (m, 4H), 3.17 (m, 4H), 4.90 (br, 2H), 5.75 (t, 1H), 6.94 (m, 4H), 7.08-7038 (m, 4H)

Example 90

Carbonic acid 4-{4-[3-carbamoyloxy-3-(4-fluoro-phenyl)-propyl]-piperazin-1-yl}-phenyl ethyl ester The compound 'carbamic acid 1-(4-fluoro-phenyl)-3-[4-(4-hydroxy-phenyl)-piperazin-1-yl]-propyl ester (0.93 mmol) prepared in Example 88 was dissolved in acetone (15 mL), and triethylamine (1.86 mmol) was added and ethyl chloroformate (2.4 mmol) was added dropwise, and the resulting mixture was then stirred at a room temperature for 5 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

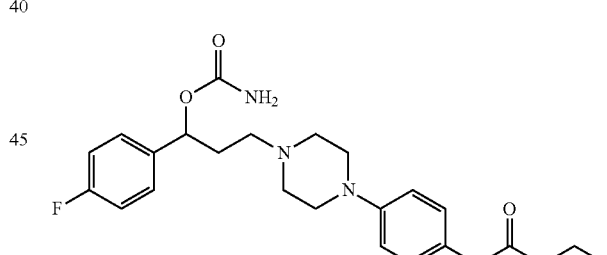

$^1$H NMR (200 MHz, CDCl3) d: 1.40 (m, 3H), 2.04 (m, 1H), 2.21 (m, 1H), 2.43 (m, 2H), 2.63 (m, 4H), 3.19 (m, 4H), 4.30 (m, 2H), 4.79 (br, 2H), 5.72 (t, 1H), 6.88 (m, 2H), 7.06 (m, 4H), 7.34 (m, 4H)

Example 91

Carbonic acid benzyl ester 4-{4-[3-carbamoyloxy-3-(4-fluoro-phenyl)-propyl]-piperazin-1-yl}-phenyl ester The compound 'carbamic acid 1-(4-fluoro-phenyl)-3-[4-(4-hydroxy-phenyl)-piperazin-1-yl]-propyl ester (1 mmol) prepared in Example 88 was dissolved in acetone (20 mL), and triethylamine (2 mmol) was added and benzyl chloroformate (2.4 mmol) was added dropwise, and the resulting mixture was then stirred at a room temperature for 5 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

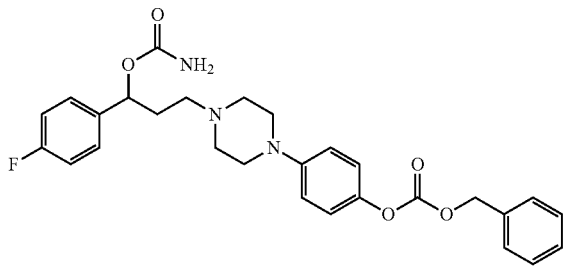 [SMILES: NC(=O)OC(CCN1CCN(c2ccc(OC(=O)OCc3ccccc3)cc2)CC1)c1ccc(F)cc1]

¹H NMR (200 MHz, CDCl3) d: 1.99 (m, 2H), 2.12 (m, 2H), 2.66 (m, 4H), 3.12 (m, 4H), 3.52 (s, 2H), 4.90 (br, 2H), 5.81 (t, 1H), 6.89 (m, 4H), 7.33 (m, 9H)

Example 92

Acetic acid 4-{4-[3-carbamoyloxy-3-(4-fluoro-phenyl)-propyl]-piperazin-1-yl}-phenyl ester The compound 'carbamic acid 1-(4-fluoro-phenyl)-3-[4-(4-hydroxy-phenyl)-piperazin-1-yl]-propyl ester (0.6 mmol) prepared in Example 88 was dissolved in acetone (15 mL), and triethylamine (1.2 mmol) was added and acetylchloride (2.4 mmol) was added dropwise, and the resulting mixture was then stirred at a room temperature for 5 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

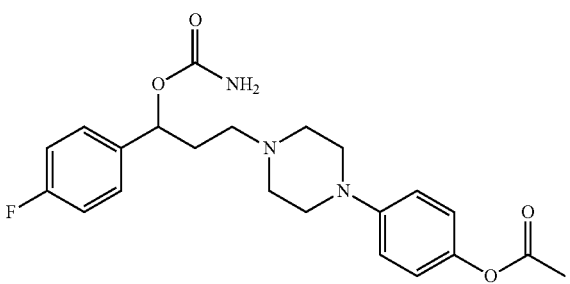 [SMILES: CC(=O)Oc1ccc(N2CCN(CCC(OC(N)=O)c3ccc(F)cc3)CC2)cc1]

¹H NMR (200 MHz, CDCl3) d: 2.02 (m, 1H), 2.17 (m, 1H), 2.38 (s, 3H), 2.42 (m, 2H), 2.60 (m, 4H), 3.18 (m, 4H), 4.82 (br, 2H), 5.75 (t, 1H), 6.88-7.09 (m, 6H), 7.33 (m, 2H)

Example 93

Carbamic acid 3-{4-[bis-(4-fluoro-phenyl)-methyl]-piperazin-1-yl}-1-phenyl-propyl ester 3-chloro propiophenone (4 mmol) and 4,4'-bisfluorophenylpiperazine (5.2 mmol) were dissolved in acetonitrile (50 mL), and triethylamine (5.2 mmol) was added dropwise thereto, and the resulting mixture was stirred at 80° C. for 24 hours. The resulting reaction mixture was diluted with water, and extracted several times with ethylacetate. The resulting organic phase was dried over magnesium sulfate and filtered, and the resulting filtrate was concentrated under a reduced pressure, and separated and purified with column chromatography (hexane:ethylacetate=1:1). The resulting compound (3.5 mmol) was dissolved in methanol (20 mL), and cooled to 0° C., and sodium borohydride (5 mmol) was added slowly to the mixture. The resulting mixture was stirred at a room temperature for 2 hours, and concentrated under a reduced pressure, and obtained a yellow pellet. Then, the prepared yellow pellet was purified with column chromatography (hexane:ethylacetate=1:1) to obtain a crude compound.

The prepared crude compound (2 mmol) was dissolved in tetrahydrofuran (10 mL), and 1,1'-carbodiimidazole (4 mmol) was added thereto, and the resulting mixture was stirred at a room temperature for 1 hour. Then, excessive ammonium hydroxide was added to the mixture, and the resulting mixture was then stirred at a room temperature for 1 hour. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

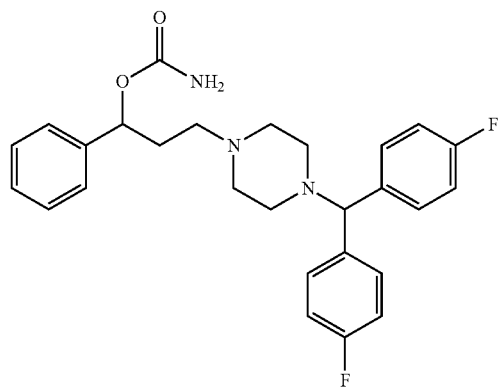 [SMILES: NC(=O)OC(CCN1CCN(C(c2ccc(F)cc2)c2ccc(F)cc2)CC1)c1ccccc1]

¹H NMR (200 MHz, Acetone) d 2.34 (m, 10H), 2.84 (m, 2H), 4.35 (s, 1H), 5.7 (t, 1H), 5.99 (br, 2H), 7.07 (m, 4H), 7.31 (m, 5H), 7.50 (m, 4H)

Example 94

Carbamic acid 1-phenyl-4-(4-phenyl-piperazin-1-yl)-butyl ester

A title compound was prepared in the same manner as in Example 93 except for the use of 4-bromobutyrophenone and phenylpiperazine as starting materials.

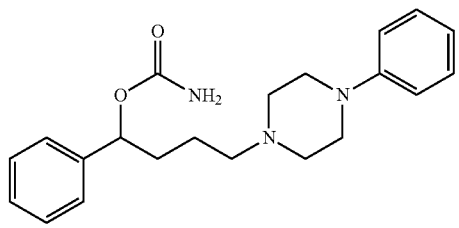 [SMILES: NC(=O)OC(CCCN1CCN(c2ccccc2)CC1)c1ccccc1]

¹H NMR (500 MHz, DMSO) d 1.82 (m, 2H), 2.78 (m, 3H), 3.08 (m, 4H), 3.21 (m, 4H), 3.52 (m, 2H), 5.51 (br, 2H), 5.78 (t, 1H), 7.01 (m, 5H), 7.23 (m, 5H)

Example 95

Carbamic acid 4-[4-(2-methoxy-phenyl)-piperazin-1-yl]-1-phenyl-butyl ester

A title compound was prepared in the same manner as in Example 93 except for the use of 4-bromobutyrophenone and 2-methoxyphenylpiperazine as starting materials.

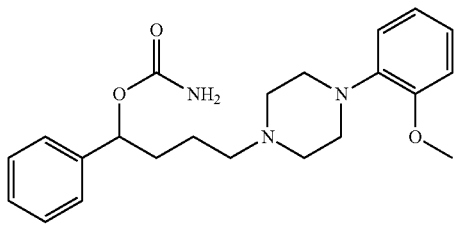 [SMILES: COc1ccccc1N1CCN(CCCC(OC(N)=O)c2ccccc2)CC1]

¹H NMR (500 MHz, DMSO) d 1.88 (m, 4H), 3.10-3.30 (m, 6H), 3.52 (m, 4H), 3.80 (s, 3H), 5.42 (br, 2H), 5.51 (t, 1H), 6.91 (m, 1H), 7.01 (m, 2H), 7.09 (m, 1H), 7.33 (m, 5H)

Example 96

Carbamic acid 1-phenyl-4-(4-pyridin-2-yl-piperazin-1-yl)-butyl ester

A title compound was prepared in the same manner as in Example 93 except for the use of 4-bromobutyrophenone and 2-pyridylpiperazine as starting materials.

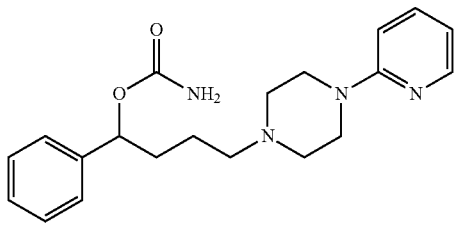 [SMILES: NC(=O)OC(CCCN1CCN(c2ccccn2)CC1)c1ccccc1]

¹H NMR (500 MHz, DMSO) d 3.12 (m, 6H), 3.44 (m, 4H), 3.64 (m, 4H), 4.52 (m, 4H), 5.55 (t, 1H), 6.51-6.91 (br, 2H), 7.01 (m, 2H), 7.30-7.40 (m, 5H), 8.01 ((m, 2H)

Example 97

Carbamic acid 4-[4-(3-chloro-pyridin-2-yl)-piperazin-1-yl]-1-phenyl-butyl ester

A title compound was prepared in the same manner as in Example 93 except for the use of 4-bromobutyrophenone and 1-(3-chloro-pyridin-2-yl)-piperazine as starting materials.

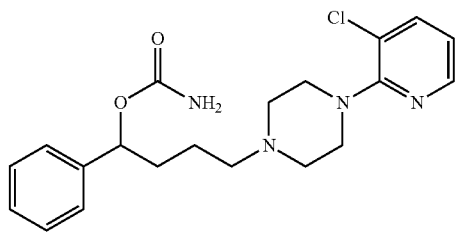 [SMILES: NC(=O)OC(CCCN1CCN(c2ncccc2Cl)CC1)c1ccccc1]

¹H NMR (500 MHz, DMSO) d 1.78 (m, 5H), 3.80 (m, 3H), 3.52 (m, 3H), 3.41 (m, 3H), 5.02 (br, 2H), 5.50 (t, 1H), 7.10 (m, 1H), 7.41 (m, 5H), 7.91 (m, 1H), 8.31 ((m, 1H)

Example 98

Carbamic acid 3-(4-benzo[1,3]dioxol-5-ylmethyl-piperazin-1-yl)-1-phenyl-propyl ester A title compound was prepared in the same manner as in Example 93 except for the use of 3-chloropropiophenone and 3,4-methylene dioxy benzylpiperazine as starting materials.

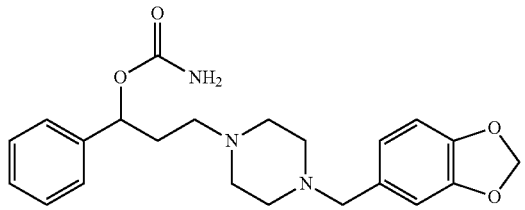 [SMILES: NC(=O)OC(CCN1CCN(Cc2ccc3c(c2)OCO3)CC1)c1ccccc1]

¹H NMR (200 MHz, Acetone) d 1.99 (m, 2H), 2.35 (m, 10H), 3.40 (d, 2H), 5.78 (t, 1H), 5.97 (br, 4H), 6.78 (d, 2H), 6.87 (s, 1H), 7.36 (m, 5H)

Example 99

Carbamic acid 3-(4-benzoyl-piperazin-1-yl)-1-phenyl-propyl ester

A title compound was prepared in the same manner as in Example 93 except for the use of 3-chloropropiophenone and benzoyl piperazine as starting materials.

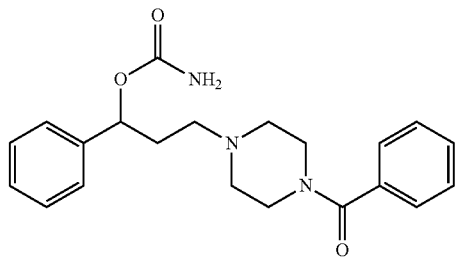 [SMILES: NC(=O)OC(CCN1CCN(C(=O)c2ccccc2)CC1)c1ccccc1]

¹H NMR (200 MHz, CDCl₃) d 1.9-2.3 (m, 8H), 3.2-3.8 (br, 4H), 4.95 (br, 2H), 5.82 (t, 1H), 7.32-7.39 (m, 10H)

Example 100

Carbamic acid 3-(4-benzyl-piperazin-1-yl)-1-phenyl-propyl ester

A title compound was prepared in the same manner as in Example 93 except for the use of 3-chloropropiophenone and benzyl piperazine as starting materials.

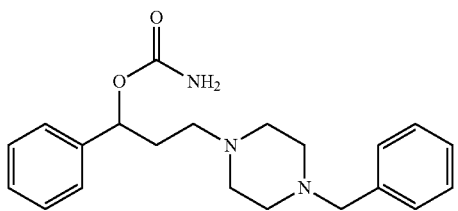 [SMILES: NC(=O)OC(CCN1CCN(Cc2ccccc2)CC1)c1ccccc1]

¹H NMR (200 MHz, Acetone) d 2.07 (m, 2H), 2.41 (m, 10H), 3.53 (s, 2H), 4.90 (br, 2H), 5.70 (t, 1H), 7.31 (m, 10H)

Example 101

Carbamic acid (R)-3-[4-(4-methoxy-phenyl)-2,6-dimethyl-piperazin-1-yl]-1-phenyl-propyl ester (R)-3-chloro-1-phenyl-1-propanol (10 mmol) was dissolved in acetonitrile (100 ml), and 2,6-dimethyl-4-methoxy phenylpiperazine (12 mmol) and triethylamine (12 mmol) were added to the resulting mixture. The prepared mixture was stirred at 80° C. for 24 hours. The resulting reaction mixture was diluted with water, and extracted several times with ethyl acetate. The extracted organic phase was washed with an aqueous sodium chloride solution, dried over magnesium sulfate, and then concentrated under a reduced pressure to obtain a pellet. The prepared pellet (8.2 mmol) was dissolved in tetrahydrofuran (50 mL), and 1,1'-carbonyl dimidazole (16.5 mmol) was added thereto, and the resulting mixture was stirred at a room temperature for 1 hour. Excessive ammonium hydroxide was added to the mixture, and the resulting mixture was stirred for 2. The resulting reaction mixture was diluted with water, and extracted several times with ethyl acetate to obtain an organic phase. Then, the prepared organic phase was dried over magnesium sulfate, and concentrated under a reduced pressure. The resulting yellow pellet was purified with column chromatography (hexane: ethyl acetate=1:1) to obtain a title compound.

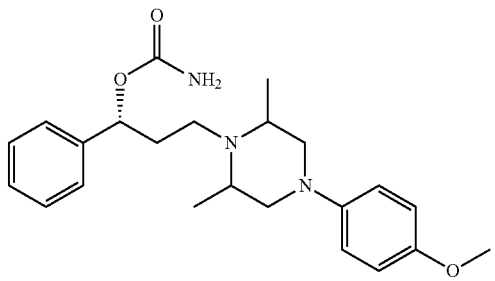 [SMILES: COc1ccc(N2CC(C)N(CC[C@@H](OC(N)=O)c3ccccc3)C(C)C2)cc1]

¹H NMR (200 MHz, CDCl₃) d 1.05 (dd, 6H), 1.99 (m, 2H), 2.45 (m, 2H), 2.78 (m, 4H), 3.27 (m, 2H), 3.78 (s, 3H), 4.71 (br, 2H), 5.66 (t, 1H), 6.85 (m, 4H), 7.3 (m, 5H)

Example 102

(R)-carbamic acid 3-[4-(4-methoxy-phenyl)-piperazin-1-yl]-1-phenyl-propyl ester

A title compound was prepared in the same manner as in Example 101 except for the use of (R)-3-chloro-1-phenyl-1-propanol and 4-methoxyphenylpiperazine as starting materials.

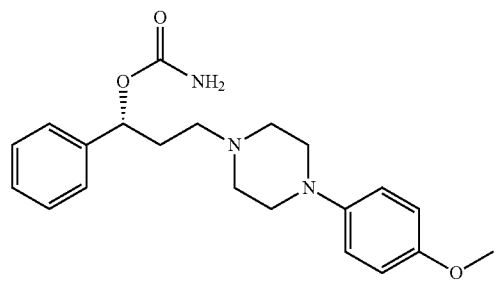 [SMILES: COc1ccc(N2CCN(CC[C@@H](OC(N)=O)c3ccccc3)CC2)cc1]

¹H NMR (200 MHz, CDCl3) d: 2.12 (m, 1H), 2.27 (m, 1H), 2.42 (m, 2H), 2.65 (m, 4H), 3.13 (m, 4H), 3.79 (s, 3H), 4.87 (br, 2H), 5.79 (t, 1H), 6.89 (m, 4H), 7.33 (m, 5H)

Example 103

(R)-carbamic acid 3-[4-(4-chloro-phenyl)-piperazin-1-yl]-1-phenyl-propyl ester

A title compound was prepared in the same manner as in Example 101 except for the use of (R)-3-chloro-1-phenyl-1-propanol and 4-chlorophenylpiperazine as starting materials.

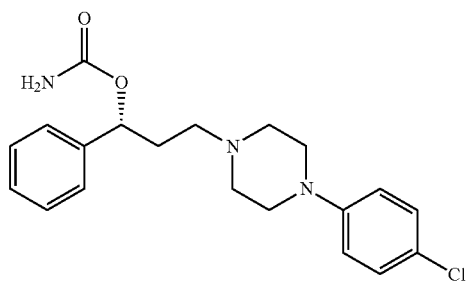 [SMILES: NC(=O)O[C@H](CCN1CCN(c2ccc(Cl)cc2)CC1)c1ccccc1]

¹H NMR (200 MHz, CDCl3) d: 1.98 (m, 1H), 2.21 (m, 1H), 2.43 (m, 2H), 2.60 (m, 4H), 3.18 (m, 4H), 4.67 (br, 2H), 5.76 (t, 1H), 6.85 (m, 2H), 7.24 (m, 2H), 7.37 (m, 5H)

Example 104

(R)-carbamic acid 3-[4-(4-fluoro-phenyl)-piperazin-1-yl]-1-phenyl-propyl ester

A title compound was prepared in the same manner as in Example 101 except for the use of (R)-3-chloro-1-phenyl-1-propanol and 4-fluorophenylpiperazine as starting materials.

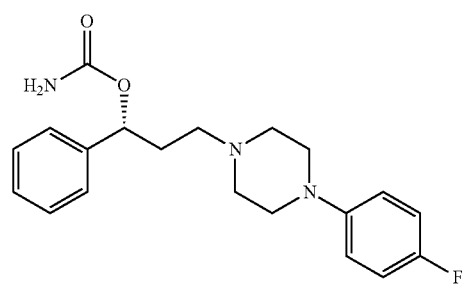 [SMILES: NC(=O)O[C@H](CCN1CCN(c2ccc(F)cc2)CC1)c1ccccc1]

¹H NMR (200 MHz, CDCl₃) d: 2.11 (m, 1H), 2.21 (m, 1H), 2.29 (m, 2H), 2.61 (m, 4H), 3.14 (m, 4H), 4.83 (br, 2H), 5.75 (t, 1H), 6.93 (m, 4H), 7.33 (m, 5H)

Example 105

(R)-carbamic acid 3-[4-(4-hydroxy-phenyl)-piperazin-1-yl]-1-phenyl-propyl ester

A title compound was prepared in the same manner as in Example 101 except for the use of (R)-3-chloro-1-phenyl-1-propanol and 4-hydroxyphenylpiperazine as starting materials.

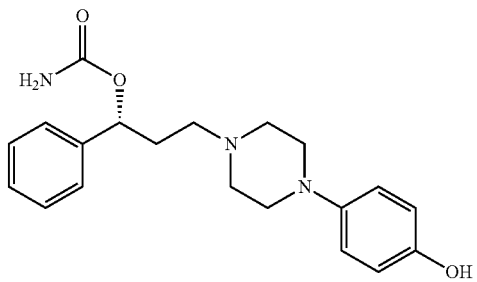 [SMILES: NC(=O)O[C@H](CCN1CCN(c2ccc(O)cc2)CC1)c1ccccc1]

¹H NMR (200 MHz, CDCl3) d: 1.99 (m, 2H), 2.14 (m, 2H), 2.58 (m, 4H), 3.12 (m, 4H), 5.12 (br, 2H), 5.78 (t, 1H), 6.99 (m, 4H), 7.21 (m, 5H)

Example 106

(S)-carbamic acid 3-[4-(4-methoxy-phenyl)-piperazin-1-yl]-1-phenyl-propyl ester

A title compound was prepared in the same manner as in Example 101 except for the use of (S)-3-chloro-1-phenyl-1-propanol and 4-methoxyphenylpiperazine as starting materials.

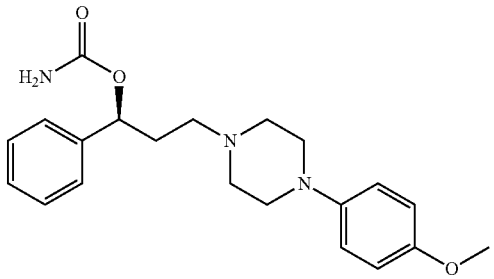 [SMILES: COc1ccc(N2CCN(CC[C@H](OC(N)=O)c3ccccc3)CC2)cc1]

¹H NMR (200 MHz, CDCl3) d: 2.12 (m, 1H), 2.27 (m, 1H), 2.42 (m, 2H), 2.65 (m, 4H), 3.13 (m, 4H), 3.79 (s, 3H), 4.87 (br, 2H), 5.79 (t, 1H), 6.89 (m, 4H), 7.33 (m, 5H)

Example 107

4-{2-[4-(4-methoxy-phenyl)-piperazin-1-yl]-ethyl}-1,4-dihydro-benzo[d][1,3]oxazin-2-one 2'-nitro acetophenone (4.67 mmol) and 4-methoxyphenylpiperazine (5.61 mmol) were dissolved in ethanol (30 mL), and the resulting mixture was adjusted to pH 2 to 3 by adding concentrated hydrochloric acid dropwise. Paraformaldehyde (37.36 mmol) was added to the mixture, and the resulting mixture was refluxed for 24 hours. The resulting reaction mixture were distilled under a reduced pressure, neutralized with 1 normal sodium chloride aqueous solution, diluted with water, and then extracted several times with ethylacetate. The resulting organic phase was dried over magnesium sulfate, and filtered, and the resulting filtrate was concentrated under a reduced pressure, and separated and purified with column chromatography (hexane:ethyl acetate=1:1) to obtain a crude compound. The separated crude compound (3.65 mmol) was dissolved in methanol (30 mL), and cooled to 0° C., and sodium borohydride (NaBH₄, 7 mmol) was added slowly to the mixture. The resulting mixture was stirred at a room temperature for 2 hours, and concentrated under a reduced pressure. Then, the resulting orange pellet was purified with column chromatography (hexane:ethylacetate=1:1). The purified compound (3.1 mmol) was dissolved in methanol, and subject to the hydrogenation reaction at the presence of platinum catalyst to obtain an amino compound with a reduced nitro group. The prepared compound (1.21 mmol) was dissolved in tetrahydrofuran (20 mL), and triethylamine (3 mmol) was added, and phosgene (a 2.4 M toluene solution, 1.21 mmol) was added slowly to the mixture. In this case, a temperature of the reaction product was carefully maintained in a temperature range of no more than 10° C. The reaction product was stirred at a room temperature for 16 hours, diluted with ammonium hydroxide, and then extracted several times with ethyl acetate. The resulting organic phase was dried over magnesium sulfate, and filtered, and the resulting filtrate was concentrated under a reduced pressure, and re-crystallized from ethyl acetate to prepare a final compound.

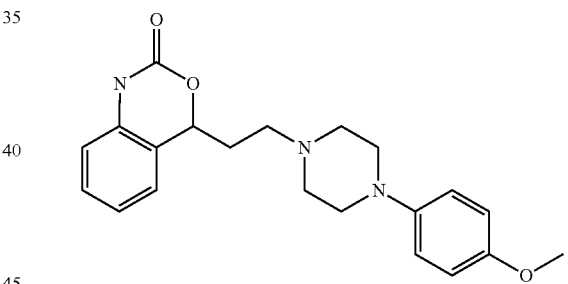

¹H NMR (200 MHz, CDCl3) d 2.07 (m, 4H), 2.61 (m, 4H), 3.12 (m, 4H), 3.78 (s, 3H), 5.58 (t, 1H), 6.85 (m, 5H), 7.16 (m, 1H), 7.22 (m, 3H), 9.14 (s, 1H)

Example 108

Carbamic acid 3-[4-(4-methoxy-phenyl)-piperazin-1-yl]-1-phenyl-butyl ester

Phenyl-1-propenyl-ketone (4.1 mmol) and 4-methoxy phenylpiperazine (4.9 mmol) were dissolved in ethanol (30 mL), and the resulting mixture was stirred at 72° C. for 48 hours. The mixture was distilled under a reduced pressure, diluted with water, and then extracted twice with ethyl acetate. The resulting organic phase was distilled under a reduced pressure, dried over magnesium sulfate, and filtered, and the resulting filtrate was concentrated under a reduced pressure, and purified with column chromatography (hexane: ethylacetate=4:1) to obtain a crude compound. The prepared crude compound (2.9 mmol) was dissolved in methanol (20 mL), and NaBH₄ (3.8 mmol) was added slowly to the mixture. The resulting mixture was stirred at a room temperature for 2 hour, and concentrated under a reduced pressure, and obtained a yellow pellet. The prepared yellow pellet was purified with column chromatography (hexane:ethylacetate=1:1). The purified compound (2 mmol) was dissolved in tetrahydrofuran (15 mL), and 1,1'-carbodiimidazole (4 mmol) was added to the purified compound. The resulting mixture was stirred at a room temperature for 1 hour, and excessive ammonium hydroxide was added to the mixture, and the resulting mixture was stirred at a room temperature for additional 2 hours. The resulting reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a final compound.

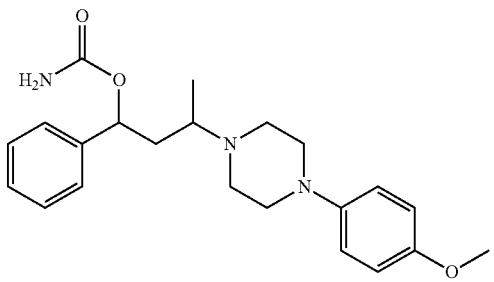 [SMILES: COc1ccc(N2CCN(C(C)CC(OC(N)=O)c3ccccc3)CC2)cc1]

$^1$H NMR (200 MHz, CDCl$_3$) d 1.81 (m, 1H), 2.32 (m, 1H), 2.5 (m, 3H), 2.8 (m, 2H), 3.14 (m, 4H), 3.80 (s, 3H), 4.80 (br, 2H), 6.02 (t, 1H), 6.92 (m, 4H), 7.36 (m, 5H)

Example 109

Carbamic acid 3-[4-(4-chloro-phenyl)-piperazin-1-yl]-1-phenyl-butyl ester

A title compound was prepared in the same manner as in Example 104 except for the use of phenyl-1-propenyl-ketone and 4-chlorophenylpiperazine as starting materials.

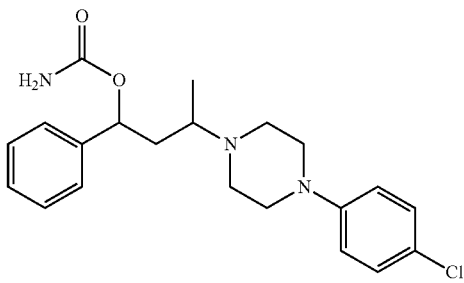 [SMILES: CC(CC(OC(N)=O)c1ccccc1)N1CCN(c2ccc(Cl)cc2)CC1]

$^1$H NMR (200 MHz, CDCl$_3$) d 1.82 (m, 2H), 2.31 (m, 1H), 2.74-2.55 (m, 8H), 3.18 (m, 3H), 4.69 (br, 2H), 5.90 (t, 1H), 6.87 (m, 2H), 7.22 (m, 2H), 7.32 (m, 5H)

Example 110

Carbamic acid 3-[4-(4-nitro-phenyl)-piperazin-1-yl]-1-phenyl-butyl ester

A title compound was prepared in the same manner as in Example 104 except for the use of phenyl-1-propenyl-ketone and 4-nitrophenylpiperazine as starting materials.

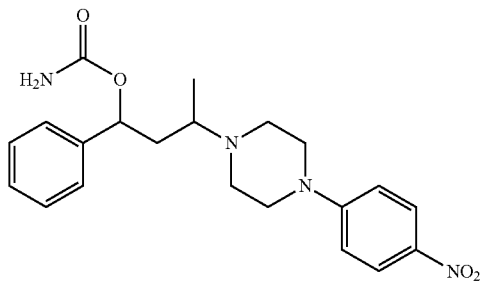 [SMILES: CC(CC(OC(N)=O)c1ccccc1)N1CCN(c2ccc([N+](=O)[O-])cc2)CC1]

$^1$H NMR (200 MHz, CDCl$_3$) d 1.81 (m, 2H), 1.91 (m, 1H), 2.20-2.90 (m, 8H), 3.45 (m, 3H), 4.75 (br, 2H), 5.92 (t, 1H), 6.84 (m, 2H), 7.35 (m, 5H), 8.13 (m, 2H)

Example 111

Carbamic acid 3-[4-(3,4-dimethyl-phenyl)-piperazin-1-yl]-1-phenyl-butyl ester

A title compound was prepared in the same manner as in Example 104 except for the use of phenyl-1-propenyl-ketone and 3,4-dimethylphenylpiperazine as starting materials.

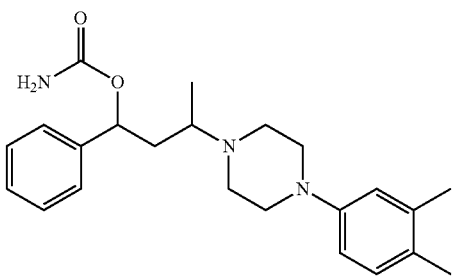 [SMILES: Cc1ccc(N2CCN(C(C)CC(OC(N)=O)c3ccccc3)CC2)cc1C]

$^1$H NMR (200 MHz, CDCl$_3$) d 1.72 (m, 2H), 2.20 (s, 3H), 2.52 (s, 3H), 2.52 (m, 4H), 2.80 (m, 3H), 3.17 (m, 5H), 5.01 (br, 2H), 5.82 (t, 1H), 6.90 (m, 2H), 7.05 (m, 1H), 7.37 (m, 5H)

Example 112

Carbamic acid 3-[4-(4-quinoxaline-phenyl)-piperazin-1-yl]-1-phenyl-butyl ester

A title compound was prepared in the same manner as in Example 104 except for the use of phenyl-1-propenyl-ketone and 2-piperazin-1-yl-quinoxaline as starting materials.

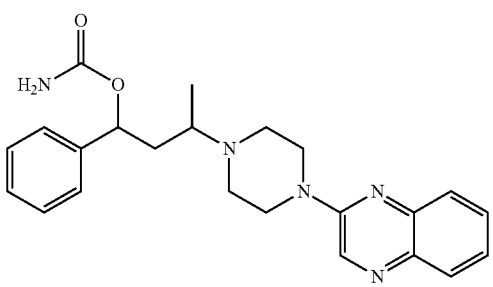 [SMILES: CC(CC(OC(N)=O)c1ccccc1)N1CCN(c2cnc3ccccc3n2)CC1]

¹H NMR (200 MHz, CDCl₃) d 1.71 (m, 2H), 2.21 (m, 2H), 2.48-2.78 (m, 7H), 3.83 (m, 3H), 4.69 (br, 2H), 5.87 (t, 1H), 7.38 (m, 5H), 7.61 (m, 3H), 7.86 (m, 1H), 8.59 (d, 1H)

Example 113

Carbamic acid 3-[4-(3,4-dimethoxy-phenyl)-piperazin-1-yl]-1-phenyl-butyl ester

A title compound was prepared in the same manner as in Example 104 except for the use of phenyl-1-propenyl-ketone and 3,4-dimethoxyphenylpiperazine as starting materials.

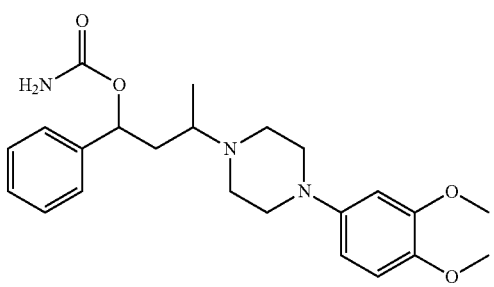 [SMILES: COc1ccc(N2CCN(C(C)CC(OC(N)=O)c3ccccc3)CC2)cc1OC]

¹H NMR (200 MHz, CDCl3) d 1.32 (m, 1H), 2.21 (m, 1H), 2.42 (m, 4H), 2.72 (m, 4H), 3.10 (m, 5H), 3.80 (s, 3H), 3.83 (s, 3H), 5.01 (br, 2H), 5.89 (t, 1H), 6.42 (d, 1H), 6.80 (d, 1H), 6.89 (d, 1H), 7.33 (m, 5H)

Example 114

Carbamic acid 3-[4-(3,5-dichloro-pyridin-2-yl-piperazin-1-yl]-1-phenyl-butyl ester A title compound was prepared in the same manner as in Example 104 except for the use of phenyl-1-propenyl-ketone and 3,5-dichloropyridylpiperazine as starting materials.

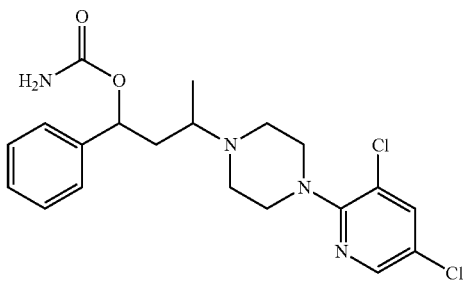 [SMILES: CC(CC(OC(N)=O)c1ccccc1)N1CCN(c2ncc(Cl)cc2Cl)CC1]

¹H NMR (200 MHz, CDCl₃) d 1.68 (m, 1H) 2.21 (m, 2H), 2.54 (m, 4H), 2.71 (m, 2H), 3.36 (m, 5H), 5.01 (br, 2H), 5.91 (t, 1H), 7.2-7.4 (m, 5H), 7.60 (m, 1H), 8.10 (m, 1H)

Example 115

Carbamic acid 3-[4-(3,4-dichloro-phenyl)-piperazin-1-yl]-1-phenyl-butyl ester

A title compound was prepared in the same manner as in Example 104 except for the use of phenyl-1-propenyl-ketone and 3,4-dichlorophenylpiperazine as starting materials.

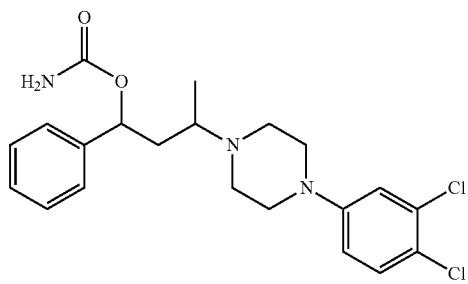 [SMILES: CC(CC(OC(N)=O)c1ccccc1)N1CCN(c2ccc(Cl)c(Cl)c2)CC1]

¹H NMR (200 MHz, CDCl₃) d 1.62 (m, 2H), 1.96 (m, 2H), 2.20-2.60 (m, 5H), 2.75 (m, 2H), 3.16 (m, 3H), 4.96 (br, 2H), 5.91 (t, 1H), 6.77 (m, 1H), 7.00 (m, 1H), 7.36 (m, 6H)

Example 116

Carbamic acid 3-[4-(2,4-difluoro-phenyl)-piperazin-1-yl]-1-phenyl-butyl ester

A title compound was prepared in the same manner as in Example 104 except for the use of phenyl-1-propenyl-ketone and 2,4-difluorophenylpiperazine as starting materials.

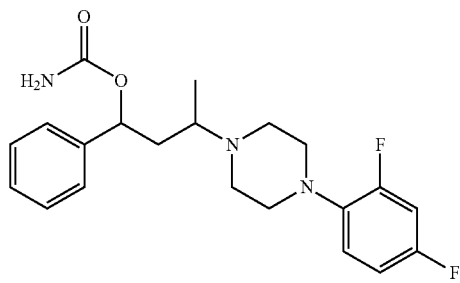 [SMILES: CC(CC(OC(N)=O)c1ccccc1)N1CCN(c2ccc(F)cc2F)CC1]

¹H NMR (200 MHz, CDCl₃) 1.86 (m, 2H), 2.12 (m, 2H), 2.52 (m, 4H), 2.75 (m, 3H), 3.06 (m, 3H), 4.98 (br, 2H), 5.81 (t, 1H), 6.79 (m, 3H), 7.36 (m, 5H)

Example 117

Carbamic acid 2-fluoro-1-phenyl-3-(4-phenyl-piperazin-1-yl)-propyl ester 3-chloropropiophenone (14.77 mmol) and phenylpiperazine (17.7 mmol) were dissolved in acetonitrile (50 mL), and triethylamine (17.7 mmol) was added thereto, and the resulting mixture was stirred at 80° C. for 24 hours. The resulting reaction mixture was diluted with water, and extracted several times with ethyl acetate. The extracted organic phase was collected, washed with water and an aqueous saturated sodium chloride solution, dried over magnesium sulfate, and then concentrated under a reduced pressure to obtain a pellet. The prepared pellet (1.75 mmol) was dissolved in tetrahydrofuran (20 mL), and 1.5 mole of a cyclohexanelithium diimide (1.92 mmol) solution was added dropwise while the resulting mixture was maintained to a temperature of −78° C. Then, the resulting mixture was stirred at −78° C. for 10 minutes, and then stirred at 0° C. for 30 minutes. After the resulting mixture was cooled again and maintained to a temperature of −78° C., N-fluorobenzenesulfonimide (2.27 mmol) was added to the mixture, and the resulting mixture was stirred at a room temperature for 2 hours. The resulting reaction mixture was diluted by adding a saturated ammonium chloride solution, and the diluted reaction mixture was extracted several times with ethylacetate. The resulting organic phase was dried over magnesium sulfate, and concentrated under a reduced pressure. In this case, the resulting pellet was purified with column chromatography (hexane:ethyl acetate=1:4) to obtain a crude compound. The prepared crude compound (1.5 mmol) was dissolved in methanol (20 mL), and NaBH$_4$ (3.0 mmol) was added slowly to the mixture. The resulting mixture was stirred at a room temperature for 1 hour, and concentrated under a reduced pressure to remove off solvents. The resulting pellet was then purified with column chromatography (hexane:ethylacetate=1:2) to obtain a crude compound. The prepared crude compound (1 mmol) was dissolved in tetrahydrofuran (20 mL), and 1,1'-carbodiimidazole (2 mmol) was added thereto, and the resulting mixture was stirred at a room temperature for 2 hour. Then, excessive ammonium hydroxide was added to the mixture, and the resulting mixture was stirred at a room temperature for additional 2 hours. The resulting reaction mixture was diluted with water, and extracted several times with ethyl acetate to obtain an organic phase. The prepared organic phase was dried over magnesium sulfate, and then concentrated under a reduced pressure. The resulting pellet was purified with column chromatography (hexane:ethyl acetate=1:4) to obtain a final compound.

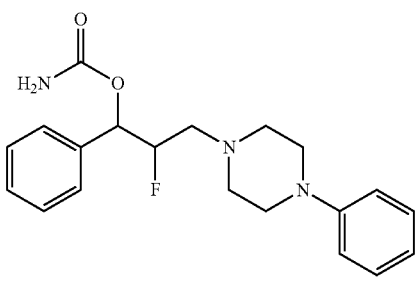 [SMILES: NC(=O)OC(c1ccccc1)C(F)CN1CCN(c2ccccc2)CC1]

$^1$H NMR (200 MHz, CDCl3) d 2.59 (m, 6H), 3.19 (m, 4H), 4.92 (m, 1H, J=48 Hz), 5.52 (br, 2H), 5.92 (m, 1H, J=18 Hz), 6.90 (m, 3H), 7.34 (m, 7H)

The compounds as listed above were tested for analgesic effects using the following animal models.

2. Acetic Acid-Induced Writhing Test in Mouse

An acetic acid-induced writhing test is one of models for measuring an analgesic effect of drugs. A test material dissolved in a suitable vehicle was orally administered to a male ICR mouse weighing 30 to 35 g at an amount of 10 mg/kg. After 1 hour of the oral administration, 10 mg/ml of an aqueous 0.8% acetic acid solution was intraperitoneally injected into the male ICR mouse to induce the abdominal pain of the male ICR mouse. Right after the administration of acetic acid, the male ICR mouse was put into an empty cage, and the number of writhing behaviors of the mice was counted for 10 minutes. The term "writhing represents a reflex action in which the mouse overtly extends its abdomen by stretching its hind legs due to the abdominal pain. The analgesic effect of the test material is represented by the 'suppression ratio of pain response' {[(Writhing number of Vehicle-administered group–Writhing number of Test material-administered group)/(Writhing number of Vehicle-administered group)]× 100%} or 50% of Effective amount (ED$_{50}$ (median effective dose); an amount of test material that is required to suppress 50% of pain behaviors) of Test material. The ED$_{50}$ (median effective dose) was determined by calculating the suppression ratio of pain response in at least three doses of test materials and subjecting to the linear regression. From these results, it was observed that the higher analgesic effect shows the higher suppression ratio of pain response (%), but the lower ED$_{50}$ value.

3. Formalin Test—Late Phase in Mouse

A formalin test is another model for measuring an analgesic effect of drugs. When a formalin solution was subcutaneously administered into the planta surface of a mouse's hindlimb, the mouse shows specific pain behaviors such as immediately holding up and down, flinching and licking a mouse's left foot. These pain behaviors have a biphasic pattern, and therefore they are divided into an early-phase behavior within 10 seconds after the formalin administration; and a late-phase behavior up to 10 to 60 minutes. The medicinal effect observed in the formalin test-late phase means an analgesic effect of the test material in the inflammatory pain model, and also becomes a measure that may predict the medicinal effects in the neuropathic pain model (Vissers K et. al, 2003). A test material was orally administered to a male ICR mouse weighing 30 to 35 g. After 1 hour of the oral administration, 20 μl of a 2.5% formalin solution was subcutaneously injected into the planta surface of a mouse's hindlimb to induce pain. After 20 minutes of the administration of the formalin solution, the time when the mouse shows the pain behaviors (flinching, licking, etc.) was recorded for 15 minutes, and quantified. The analgesic effect of the test material is represented by the 'suppression ratio of pain response' {[(Pain response time of Vehicle-administered group–Pain response time of Test material-administered group)/(Pain response time of Vehicle-administered group)]×100%}, or '50% of Effective amount (ED$_{50}$; an amount of a test material that is required to suppress 50% of pain behaviors) of Test material'. The ED$_{50}$ (median effective dose) was determined by calculating the suppression ratio of pain response in at least three doses of test materials and subjecting to the linear regression. From these results, it was observed that the higher analgesic effect shows the higher suppression ratio of pain response (%), but the lower ED$_{50}$ value.

TABLE 1

Results on Acetic acid - induced writhing test and Formalin test - late phase in mouse

| compound | Suppression ratio of Pain response (% at 10 po) or ED$_{50}$ (po or ip) | |
| --- | --- | --- |
| | AA Writhing | Formalin |
| Example 1: carbamic acid 1-phenyl-3-(4-phenyl-piperazin-1-yl)-propyl ester | ED$_{50}$ = 6.31 po | ED$_{50}$ = 8.43 po |

TABLE 1-continued

Results on Acetic acid - induced writhing
test and Formalin test - late phase in mouse

| compound | Suppression ratio of Pain response (% at 10 po) or $ED_{50}$ (po or ip) | |
| --- | --- | --- |
| | AA Writhing | Formalin |
| Example 2: carbamic acid 1-(4-chloro-phenyl)-3-(4-phenyl-piperazin-1-yl)-propyl ester | $ED_{50}$ = 2.14 po | $ED_{50}$ = 2.20 po |
| Example 4: carbamic acid 1-(3-nitro-phenyl)-3-(4-phenyl-piperazin-1-yl)-propyl ester | 48% | 13% |
| Example 5: carbamic acid 1-(4-tert-butyl-phenyl)-3-(4-phenyl-piperazin-1-yl)-propyl ester | 62% | 51% |
| Example 6: carbamic acid 1-(4-fluoro-phenyl)-3-(4-phenyl-piperazin-1-yl)-propyl ester | $ED_{50}$ = 2.79 po | $ED_{50}$ = 4.45 po |
| Example 7: carbamic acid 1-(3-chloro-phenyl)-3-(4-phenyl-piperazin-1-yl)-propyl ester | 59% | 27% |
| Example 8: carbamic acid 1-(4-methoxy-phenyl)-3-(4-phenyl-piperazin-1-yl)-propyl ester | 43% | 38% |
| Example 9: carbamic acid 1-(4-nitro-phenyl)-3-(4-phenyl-piperazin-1-yl)-propyl ester | 91% | $ED_{50}$ = 2.39 po |
| Example 10: carbamic acid 3-(4-phenyl-piperazin-1-yl)-1-p-tolyl-propyl ester | 100% (10 ip) | 64% |
| Example 11: carbamic acid 3-[4-(2,3-dihydro-benzo[1,4]dioxin-6-yl)-piperazin-1-yl]-1-phenyl-propyl ester | 48% | — |
| Example 12: carbamic acid 1-phenyl-3-[4-(4-trifluoromethoxy-phenyl)-piperazin-1-yl]-propyl ester | 18% | — |
| Example 13: carbamic acid 3-[4-(2,4-dimethyl-phenyl)-piperazin-1-yl]-1-phenyl-propyl ester | 34% | — |
| Example 16: carbamic acid 1-phenyl-3-[4-(4-nitro-phenyl)-piperazin-1-yl]-propyl ester | $ED_{50}$ = 2.92 ip | $ED_{50}$ = 11.6 po |
| Example 17: carbamic acid 3-[4-(2,4-dimethoxy-phenyl)-piperazin-1-yl]-1-phenyl-propyl ester | 19% | — |
| Example 18: carbamic acid 3-[4-(4-chloro-3-trifluoromethyl-phenyl)-piperazin-1-yl]-1-phenyl-propyl ester | 52% | — |
| Example 19: carbamic acid 3-[4-(2,6-dimethyl-phenyl)-piperazin-1-yl]-1-phenyl-propyl ester | 48% | — |
| Example 20: carbamic acid 3-[4-(4-methoxy-phenyl)-piperazin-1-yl]-1-phenyl-propyl ester | $ED_{50}$ = 3.12 po | $ED_{50}$ = 5.77 po |
| Example 21: carbamic acid 3-[4-(4-fluoro-phenyl)-piperazin-1-yl]-1-phenyl-propyl ester | 88% | 61% |
| Example 22: carbamic acid 3-[4-(4-chloro-phenyl)-piperazin-1-yl]-1-phenyl-propyl ester | 52% (10 ip) | −7% |
| Example 23: carbamic acid 3-[4-(2-hydroxy-phenyl)-piperazin-1-yl]-1-phenyl-propyl ester | 37% | — |
| Example 24: carbamic acid 1-phenyl-3-(4-m-tolyl-piperazin-1-yl)-propyl ester | $ED_{50}$ = 0.81 ip | — |
| Example 25: carbamic acid 1-phenyl-3-(4-pyridin-2-yl-piperazin-1-yl)-propyl ester | 86% (10 ip) | — |
| Example 26: carbamic acid 3-[4-(3-methoxy-phenyl)-piperazin-1-yl]-1-phenyl-propyl ester | 55% (10 ip) | — |
| Example 27: carbamic acid 3-[4-(2-methoxy-phenyl)-piperazin-1-yl]-1-phenyl-propyl ester | $ED_{50}$ = 7.80 po | — |

TABLE 1-continued

Results on Acetic acid - induced writhing
test and Formalin test - late phase in mouse

| compound | Suppression ratio of Pain response (% at 10 po) or $ED_{50}$ (po or ip) | |
| --- | --- | --- |
| | AA Writhing | Formalin |
| Example 28: carbamic acid 3-[4-(3-chloro-pyridin-2-yl)-piperazin-1-yl]-1-phenyl-propyl ester | 48% (10 ip) | — |
| Example 29: carbamic acid 3-[4-(3,4-dimethyl-phenyl)-piperazin-1-yl]-1-phenyl-propyl ester | 99% | — |
| Example 30: carbamic acid 3-(4-benzo[1,3]dioxol-5-yl-piperazin-1-yl)-1-phenyl-propyl ester | 93% | — |
| Example 31: carbamic acid 3-[4-(3,4-dichloro-phenyl)-piperazin-1-yl]-1-phenyl-propyl ester | 85% | — |
| Example 32: carbamic acid 3-[4-(5-chloro-2-methoxy-phenyl)-piperazin-1-yl]-1-phenyl-propyl ester | 23% | — |
| Example 33: carbamic acid 3-[4-(3,5-dimethoxy-phenyl)-piperazin-1-yl]-1-phenyl-propyl ester | 13% | — |
| Example 34: carbamic acid 1-phenyl-3-(4-pyrimidin-2-yl-piperazin-1-yl)-propyl ester | 21% | — |
| Example 35: carbamic acid 3-[4-(2-nitro-4-trifluoromethyl-phenyl)-piperazin-1-yl]-1-phenyl-propyl ester | 50% | — |
| Example 36: carbamic acid 3-[4-(3-chloro-phenyl)-piperazin-1-yl]-1-phenyl-propyl ester | $ED_{50}$ = 17.5 po | — |
| Example 37: carbamic acid 1-phenyl-3-(4-o-tolyl-piperazin-1-yl)-propyl ester | $ED_{50}$ = 1.96 ip | $ED_{50}$ = 42.4 po |
| Example 38: carbamic acid 1-phenyl-3-(4-p-tolyl-piperazin-1-yl)-propyl ester | | |
| Example 39: carbamic acid 1-phenyl-3-[4-(3-trifluoromethyl-phenyl)-piperazin-1-yl]-propyl ester | 15% (10 ip) | — |
| Example 40: carbamic acid 1-phenyl-3-[4-(4-trifluoromethyl-phenyl)-piperazin-1-yl]-propyl ester | $ED_{50}$ = 1.64 ip | — |
| Example 41: carbamic acid 3-[4-(2-fluoro-phenyl)-piperazin-1-yl]-1-phenyl-propyl ester | $ED_{50}$ = 0.34 ip | $ED_{50}$ = 33.2 po |
| Example 42: carbamic acid 3-[4-(3-fluoro-phenyl)-piperazin-1-yl]-1-phenyl-propyl ester | 96% (10 ip) | — |
| Example 43: carbamic acid 3-[4-(2-nitro-phenyl)-piperazin-1-yl]-1-phenyl-propyl ester | 25% (10 ip) | — |
| Example 44: carbamic acid 3-[4-(4-methoxy-phenyl)-piperazin-1-yl]-1-(4-nitro-phenyl)-propyl ester | 64% | — |
| Example 45: carbamic acid 1-(3-chloro-phenyl)-3-[4-(4-methoxy-phenyl)-piperazin-1-yl]-propyl ester | 62% | — |
| Example 46: carbamic acid 1-(2-fluoro-phenyl)-3-[4-(4-methoxy-phenyl)-piperazin-1-yl]-propyl ester | 42% | — |
| Example 47: carbamic acid 1-(4-methoxy-phenyl)-3-[4-(4-methoxy-phenyl)-pinerazin-1-yl]-propyl ester | 53% | — |
| Example 48: carbamic acid 1-(4-tert-butyl-phenyl)-3-[4-(4-methoxy-phenyl)-pinerazin-1-yl]-propyl ester | 93% | — |
| Example 49: carbamic acid 3-[4-(4-methoxy-phenyl)-piperazin-1-yl]-1-naphthalen-2-yl-propyl ester | 64% | — |
| Example 50: carbamic acid 1-(2-chloro-phenyl)-3-[4-(4-methoxy-phenyl)-piperazin-1-yl]-propyl ester | 49% | — |

TABLE 1-continued

Results on Acetic acid - induced writhing
test and Formalin test - late phase in mouse

| compound | Suppression ratio of Pain response (% at 10 po) or $ED_{50}$ (po or ip) | |
| --- | --- | --- |
| | AA Writhing | Formalin |
| Example 51: carbamic acid 3-[4-(4-methoxy-phenyl)-piperazin-1-yl]-1-(4-trifluoromethyl-phenyl)-propyl ester | 95% | — |
| Example 52: carbamic acid 1-(3,4-difluoro-phenyl)-3-[4-(4-methoxy-phenyl)-piperazin-1-yl]-propyl ester | 61% | — |
| Example 53: carbamic acid 1-(3-fluoro-phenyl)-3-[4-(4-methoxy-phenyl)-piperazin-1-yl]-propyl ester | 57% | — |
| Example 54: carbamic acid 1-(3-methoxy-phenyl)-3-[4-(4-methoxy-phenyl)-piperazin-1-yl]-propyl ester | 69% | — |
| Example 55: carbamic acid 3-[4-(4-methoxy-phenyl)-piperazin-1-yl]-1-naphthalen-1-yl-propyl ester | 16% | — |
| Example 56: carbamic acid 3-[4-(4-methoxy-phenyl)-piperazin-1-yl]-1-p-tolyl-propyl ester | 93% | — |
| Example 57: carbamic acid 3-[4-(4-methoxy-phenyl)-piperazin-1-yl]-1-m-tolyl-propyl ester | 52% | — |
| Example 58: carbamic acid 1-(2,4-dichloro-phenyl)-3-[4-(4-methoxy-phenyl)-piperazin-1-yl]-propyl ester | 16% | — |
| Example 59: carbamic acid 3-[4-(4-methoxy-phenyl)-piperazin-1-yl]-1-o-tolyl-propyl ester | 48% | — |
| Example 60: carbamic acid 1-(2,4-dimethyl-phenyl)-3-[4-(4-methoxy-phenyl)-piperazin-1-yl-propyl ester | 62% | — |
| Example 61: carbamic acid 1-(3,4-dimethyl-phenyl)-3-[4-(4-methoxy-phenyl)-piperazin-1-yl]-propyl ester | 58% | — |
| Example 62: carbamic acid 1-(2,5-dimethyl-phenyl)-3-[4-(4-methoxy-phenyl)-piperazin-1-yl]-propyl ester | 62% | — |
| Example 63: carbamic acid 1-(4-chloro-3-trifluoromethyl-phenyl)-3-[4-(4-methoxy-phenyl)-piperazin-1-yl]-propyl ester | 46% | — |
| Example 64: carbamic acid 3-[4-(4-methoxy-phenyl)-piperazin-1-yl]-1-(2-nitro-phenyl)-propyl ester | 59% | — |
| Example 65: carbamic acid 3-[4-(4-methoxy-phenyl)-piperazin-1-yl]-1-(3-nitro-phenyl)-propyl ester | 39% | — |
| Example 66: carbamic acid 3-[4-(4-methoxy-phenyl)-piperazin-1-yl]-1-(4-trifluoromethyl-phenyl)-propyl ester | 95% | — |
| Example 67: carbamic acid 1-benzo1,3]dioxol-5-yl-3-[4-(4-methoxy-phenyl)-piperazin-1-yl]-propylester | 57% | — |
| Example 68: carbamic acid 3-[4-(4-methoxy-phenyl)-piperazin-1-yl]-1-(3-trifluoromethyl-phenyl)-propyl ester) | 48% | — |
| Example 69: carbamic acid 1-(2-fluoro-phenyl)-3-[4-(4-methoxy-phenyl)-piperazin-1-yl]-propyl ester | 57% | — |
| Example 70: carbamic acid 1-(3,4-dichloro-phenyl)-3-[4-(4-methoxy-phenyl)-piperazin-1-yl]-propyl ester | 51% | — |
| Example 71: carbamic acid 1-(4-chloro-phenyl)-3-[4-(4-methoxy-phenyl)-piperazin-1-yl]-propyl ester | 61% | — |
| Example 72: carbamic acid 1-(4-chloro-3-trifluoromethyl-phenyl)-3-[4-(4-hydroxy-phenyl)-piperazin-1-yl]-propyl ester | 53% | — |
| Example 73: carbamic acid 1-(3,4-dichloro-phenyl)-3-[4-(4-hydroxy-phenyl)-piperazin-1-yl]-propyl ester | 55% | — |

TABLE 1-continued

Results on Acetic acid - induced writhing test and Formalin test - late phase in mouse

| compound | Suppression ratio of Pain response (% at 10 po) or $ED_{50}$ (po or ip) | |
|---|---|---|
| | AA Writhing | Formalin |
| Example 74: carbamic acid 3-[4-(2-ethoxy-phenyl)-piperazin-1-yl]-1-(4-fluoro-phenyl)-propyl ester | 44% | — |
| Example 75: carbamic acid 3-[4-(5-chloro-2-methoxy-phenyl)-piperazin-1-yl]-1-(4-fluoro-phenyl)-propyl ester | 14% | — |
| Example 76: carbamic acid 3-[4-(3,4-dichloro-phenyl)-piperazin-1-yl]-1-(4-fluoro-phenyl)-propyl ester | 50% | — |
| Example 77: carbamic acid 1-(4-fluoro-phenyl)-3-[4-(4-methoxy-phenyl)-piperazin-1-yl]-propyl ester | $ED_{50}$ = 12.4 po | −18% |
| Example 78: carbamic acid 1-(4-fluoro-phenyl)-3-[4-(2-methoxy-phenyl)-piperazin-1-yl]-propyl ester | 34% | — |
| Example 79: carbamic acid 1-(4-fluoro-phenyl)-3-[4-(4-nitro-phenyl)-piperazin-1-yl]-propyl ester | 70% | −5% |
| Example 80: carbamic acid 1-(4-fluoro-phenyl)-3-(4-o-tolyl-piperazin-1-yl)-propyl ester | 29% | — |
| Example 81: carbamic acid 1-(4-fluoro-phenyl)-3-[4-(4-fluoro-phenyl)-piperazin-1-yl]-propyl ester | 52% | — |
| Example 82: carbamic acid 2-[4-(4-methoxy-phenyl)-piperazin-1-ylmethyl]-1,2,3,4-tetrahydro-naphthalen-1-yl ester | 55% | — |
| Example 85: carbamic acid 3-[4-(4-benzyloxyphenyl)-piperazin-1-yl]-1-phenyl-propyl ester | 58% | — |
| Example 86: acetic acid 4-[4-(3-carbamoyloxy-3-phenyl-propyl)-piperazin-1-yl]-phenyl ester | $ED_{50}$ = 7.52 po | 34% |
| Example 87: carbamic acid 3-[4-(4-cyclopentyloxy-phenyl)-piperazin-1-yl]-1-phenyl-propyl ester | 58% | — |
| Example 88: carbamic acid 1-(4-fluoro-phenyl)-3-[4-(4-hydroxy-phenyl)-piperazin-1-yl]-propyl ester | $ED_{50}$ = 7.24 po | 22% |
| Example 89: 1-(4-fluorophenyl)-3-(4-(4-(pivaloyloxy)phenyl)piperazin-1-yl)propyl carbamate | 63% | — |
| Example 90: carbonic acid 4-{4-[3-carbamoyloxy-3-(4-fluoro-phenyl)-propyl]-piperazin-1-yl}-phenyl ethyl ester | $ED_{50}$ = 23.4 po | — |
| Example 91: carbonic acid benzyl ester 4-{4-[3-carbamoyloxy-3-(4-fluoro-phenyl)-propyl]-piperazin-1-yl}-phenyl ester | 45% | — |
| Example 92: acetic acid 4-{4-[3-carbamoyloxy-3-(4-fluoro-phenyl)-propyl]-piperazin-1-yl}-phenyl ester | $ED_{50}$ = 0.22 ip $ED_{50}$ = 5.66 po | — |
| Example 93: carbamic acid 3-{4-[bis-(4-fluoro-phenyl)-methyl]-piperazin-1-yl}-1-phenyl-propyl ester | 47% (10 ip) | 30% |
| Example 94: carbamic acid 1-phenyl-4-(4-phenyl-piperazin-1-yl)-butyl ester | $ED_{50}$ = 0.25 ip $ED_{50}$ = 3.61 po | $ED_{50}$ = 2.79 ip |
| Example 95: carbamic acid 4-[4-(2-methoxy-phenyl)-piperazin-1-yl]-1-phenyl-butyl ester | 100% (10 ip) | — |
| Example 96: carbamic acid 1-phenyl-4-(4-pyridin-2-yl-piperazin-1-yl)-butyl ester | 79% (10 ip) | — |
| Example 97: carbamic acid 4-[4-(3-chloro-pyridin-2-yl)-piperazin-1-yl]-1-phenyl-butyl ester | 100% (10 ip) | — |
| Example 98: carbamic acid 3-(4-benzo[1,3]dioxol-5-ylmethyl-piperazin-1-yl)-1-phenyl-propyl ester | −13% (10 ip) | — |
| Example 99: carbamic acid 3-(4-benzoyl-piperazin-1-yl)-1-phenyl-propyl ester | 44% (10 ip) | — |

TABLE 1-continued

Results on Acetic acid - induced writhing
test and Formalin test - late phase in mouse

| compound | Suppression ratio of Pain response (% at 10 po) or $ED_{50}$ (po or ip) | |
|---|---|---|
| | AA Writhing | Formalin |
| Example 100: carbamic acid 3-(4-benzyl-piperazin-1-yl)-1-phenyl-propyl ester | 32% (10 ip) | — |
| Example 101: carbamic acid (R)-3-[4-(4-methoxy-phenyl)-2,6-dimethyl-piperazin-1-yl]-1-phenyl-propyl ester | 48% | — |
| Example 102:(R)-carbamic acid 3-[4-(4-methoxy-phenyl)-piperazin-1-yl]-1-phenyl-propyl ester | $ED_{50}$ = 3.15 po | $ED_{50}$ = 4.77 po |
| Example 105: (R)-carbamic acid 3-[4-(4-hydroxy-phenyl)-piperazin-1-yl]-1-phenyl-propyl ester | $ED_{50}$ = 6.49 po | 20.9% @ 10 ip |
| Example 106: (S)-carbamic acid 3-[4-(4-methoxy-phenyl)-piperazin-1-yl]-1-phenyl-propyl ester | $ED_{50}$ = 1.43 ip | $ED_{50}$ = 12.5 po |
| Example 107: 4-{2-[4-(4-methoxy-phenyl)-piperazin-1-yl]-ethyl}-1,4-dihydro-benzo [d] [1,3]oxazin-2-one | 35% | — |
| Example 108: carbamic acid 3-[4-(4-methoxy-phenyl)-piperazin-1-yl]-1-phenyl-butyl ester | 83.5% | — |
| Example 109: carbamic acid 3-[4-(4-chloro-phenyl)-piperazin-1-yl]-1-phenyl-butyl ester | 84% | — |
| Example 110: carbamic acid 3-[4-(4-nitro-phenyl)-piperazin-1-yl]-1-phenyl-butyl ester | 17% | — |
| Example 111: carbamic acid 3-[4-(3,4-dimethyl-phenyl)-piperazin-1-yl]-1-phenyl-butyl ester | 95% | — |
| Example 112: carbamic acid 3-[4-(4-quinoxaline-phenyl)-piperazin-1-yl]-1-phenyl-butyl ester | 72% | — |
| Example 113: carbamic acid 3-[4-(3,4-dimethoxy-phenyl)-piperazin-1-yl]-1-phenyl-butyl ester | 57% | — |
| Example 114: carbamic acid 3-[4-(3,5-dichloro-pyridin-2-yl-piperazin-1-yl]-1-phenyl-butyl ester | 39% | — |
| Example 115: carbamic acid 3-[4-(3,4-dichloro-phenyl)-piperazin-1-yl]-1-phenyl-butyl ester | 68% | — |
| Example 116: carbamic acid 3-[4-(2,4-difluoro-phenyl)-piperazin-1-yl]-1-phenyl-butyl ester | 87% | — |
| Example 117: carbamic acid 2-fluoro-1-phenyl-3-(4-phenyl-piperazin-1-yl)-propyl ester | $ED_{50}$ = 32.2 po | — |

It has been known that the actions of serotonin (5-HT) receptors are closely related to the induction of various psychiatry disorders, for example, depression, anxiety, schizophrenia, phobia, obsession, migraine headache, panic disorder, etc. The serotonin receptor is divided into subtypes including 5-HT1, 5-HT2, 5HT3, 5-HT4, 5-HT6, 5-HT7, etc. In particular, the 5-HT1 receptor is divided into subtypes: 5-HT1A, 5-HT1B, 5-HT1E, 5-HT1F, etc. From the preclinical electrophysiologic test, it was found that the 5-HT1A receptor of postsynaptic neuron is associated with the antidepression effect. Also, it was found that stimulation of the 5-HT1A receptor of the postsynaptic increases the anxiety, and activation of the 5-HT1A receptor of presynaptic reduces the anxiety. The 5-HT2A receptor tends to sharply decrease from adolescence to middle age of a normal human, and to slowly decrease after the middle age. A level of the 5-HT2A receptor in an elderly patient suffering from depression is very lower than that of the normal human, and therefore it was found that the deficiency of serotonin in a wide region of brain may be one cause of the depression in the elderly. The above-mentioned compounds were tested for medicinal effects against depression and anxiety through their binding to the 5-HT1A receptor and the 5-HT2A receptor.

Binding to 5-HT1A Receptor 6-week-old Sprague-Dawley (SD) rats were anesthetized in an ether container for 5 minutes, brains were separated from rats, and cortical regions were then separated from the brains of the rats. The cortical regions of the rats were put into a Tris-HCl buffer solution (50 mM, pH 7.4) and homogenized, and the homogenate was centrifuged twice at 4? at a rotary speed of 50,000 g to obtain a precipitate (membrane protein). The precipitate was put into a buffer solution, and homogenized, which was used later as a protein source. 2 nM [3H]-8-OH-DPAT was used as a radioactive isotope, and 10 uM serotonin was used to remove non-specific bindings. 25 ul of the compound, 100 ul of an aqueous radioactive isotope solution, and 100 ul of the protein source were put together, and kept at 25° C. for 1 hour. The resulting mixture was filtered with a membrane filter in a 96-well harvester when the 96-well plate reaction was completed. The competitivity of the compound to [3H]-8-OH-DPAT was determined by taking the membrane filter and measuring the radioactivity of the membrane filter in a scintillation counter, and an $IC_{50}$ value was determined by measuring the increasing concentration of the compound. The specific reaction of the compound accounted for 90% or more. The general experiments were carried out according to the method by Middlemiss et al. (1984, Eur. J. Pharmacol.).

Binding to 5-HT2A Receptor 6-week-old Sprague-Dawley (SD) rats were anesthetized in an ether container for 5 minutes, brains were separated from rats, and cortical regions were then separated from the brains of the rats. The cortical regions of the rats were put into a Tris-HCl buffer solution (50 mM, pH 7.7) and homogenized, and the homogenate was centrifuged twice at 4° C. at a rotary speed of 50,000 g to obtain a precipitate (membrane protein). The precipitate was put into a buffer solution, and homogenized, which was used later as a protein source. 0.5 nM [3H]-Ketanserin was used as a radioactive isotope, and 10 uM serotonin was used to remove non-specific bindings. 25 ul of the compound, 100 ul of an aqueous radioactive isotope solution, and 100 ul of the protein source were put together, and kept at 25° C. for 1 hour. The resulting mixture was filtered with a membrane filter in a 96-well harvester when the 96-well plate reaction was completed. The competitivity of the compound to [3H]-Ketanserin was determined by taking the membrane filter and measuring the radioactivity in a scintillation counter, and an $IC_{50}$ value was determined by measuring the increasing concentration of the compound. The specific reaction of the compound accounted for 90% or more. The general experiments were carried out according to the method by Leysen et al. (1982, Eur. J. Pharmacol).

TABLE 2

Test results on Binding of 5-HT1A and 5-HT2A Receptors

| Compound | Suppression (at 1 uM) or Concentration (nM) required to be 50% suppressed | |
|---|---|---|
| | 5-HT1A | 5-HT2A |
| Example 1: carbamic acid 1-phenyl-3-(4-phenyl-piperazin-1-yl)-propyl ester | $IC_{50}$ = 434 nM | $IC_{50}$ = 139 nM |
| Example 2: carbamic acid 1-(4-chloro-phenyl)-3-(4-phenyl-piperazin-1-yl)-propyl ester | 64.6% | 84.6% |
| Example 4: carbamic acid 1-(3-nitro-phenyl)-3-(4-phenyl-piperazin-1-yl)-propyl ester | 74.6% | 86.4% |
| Example 5: carbamic acid 1-(4-tert-butyl-phenyl)-3-(4-phenyl-piperazin-1-yl)-propyl ester | 44.4% | 98.8% |
| Example 6: carbamic acid 1-(4-fluoro-phenyl)-3-(4-phenyl-piperazin-1-yl)-propyl ester | 65.5% | 84.7% |
| Example 7: carbamic acid 1-(3-chloro-phenyl)-3-(4-phenyl-piperazin-1-yl)-propyl ester | 76.4% | 93.7% |
| Example 8: carbamic acid 1-(4-methoxy-phenyl)-3-(4-phenyl-piperazin-1-yl)-propyl ester | 67.7% | 82.0% |
| Example 9: carbamic acid 1-(4-nitro-phenyl)-3-(4-phenyl-piperazin-1-yl)-propyl ester | 81.4% | 88.0% |
| Example 10: carbamic acid 3-(4-phenyl-piperazin-1-yl)-1-p-tolyl-propyl ester | 59.6% | 85.6% |
| Example 16: carbamic acid 1-phenyl-3-[4-(4-nitro-phenyl)-piperazin-1-yl]-propyl ester | $IC_{50}$ = 6.57 uM | $IC_{50}$ = 2.05 uM |
| Example 20: carbamic acid 3-[4-(4-methoxy-phenyl)-piperazin-1-yl]-1-phenyl-propyl ester | $IC_{50}$ = 19.8 uM | $IC_{50}$ = 5.85 uM |
| Example 21: carbamic acid 3-[4-(4-fluoro-phenyl)-piperazin-1-yl]-1-phenyl-propyl ester | $IC_{50}$ = 1.05 uM | $IC_{50}$ = 64.5 nM |
| Example 22: carbamic acid 3-[4-(4-chloro-phenyl)-piperazin-1-yl]-1-phenyl-propyl ester | $IC_{50}$ = 1.86 uM | $IC_{50}$ = 264 nM |
| Example 25: carbamic acid 1-phenyl-3-(4-pyridin-2-yl-piperazin-1-yl)-propyl ester | $IC_{50}$ = 338 nM | $IC_{50}$ = 448 nM |
| Example 26: carbamic acid 3-[4-(3-methoxy-phenyl)-piperazin-1-yl]-1-phenyl-propyl ester | $IC_{50}$ = 80.8 nM | $IC_{50}$ = 502 nM |
| Example 27: carbamic acid 3-[4-(2-methoxy-phenyl)-piperazin-1-yl]-1-phenyl-propyl ester | $IC_{50}$ = 97.6 nM | $IC_{50}$ = 164 nM |

TABLE 2-continued

Test results on Binding of 5-HT1A and 5-HT2A Receptors

| | Suppression (at 1 uM) or Concentration (nM) required to be 50% suppressed | |
|---|---|---|
| Compound | 5-HT1A | 5-HT2A |
| Example 36: carbamic acid 3-[4-(3-chloro-phenyl)-piperazin-1-yl]-1-phenyl-propyl ester | $IC_{50} = 93.8$ nM | $IC_{50} = 61.5$ nM |
| Example 39: carbamic acid 1-phenyl-3-[4-(3-trifluoromethyl-phenyl)-piperazin-1-yl]-propyl ester | $IC_{50} = 12.6$ nM | $IC_{50} = 660$ nM |
| Example 41: carbamic acid 3-[4-(2-fluoro-phenyl)-piperazin-1-yl]-1-phenyl-propyl ester | $IC_{50} = 160$ nM | $IC_{50} = 110$ nM |
| Example 78: carbamic acid 1-(4-fluoro-phenyl)-3-[4-(2-methoxy-phenyl)-piperazin-1-yl]-propyl ester | 79.0% | 71.5% |
| Example 79: carbamic acid 1-(4-fluoro-phenyl)-3-[4-(4-nitro-phenyl)-piperazin-1-yl]-propyl ester | 29.6% | 29.6% |
| Example 80: carbamic acid 1-(4-fluoro-phenyl)-3-(4-o-tolyl-piperazin-1-yl)-propyl ester | 75.3% | 76.8% |
| Example 81: carbamic acid 1-(4-fluoro-phenyl)-3-[4-(4-fluoro-phenyl)-piperazin-1-yl]-propyl ester | 60.9% | 93.9% |
| Example 93: carbamic acid 3-{4-[bis-(4-fluoro-phenyl)-methyl]-piperazin-1-yl}-1-phenyl-propyl ester | $IC_{50} = >10$ uM | $IC_{50} = 940$ nM |
| Example 94: carbamic acid 1-phenyl-4-(4-phenyl-piperazin-1-yl)-butyl ester | IC50 = 89.8 nM | IC50 = 514 nM |
| Example 95: carbamic acid 4-[4-(2-methoxy-phenyl)-piperazin-1-yl]-1-phenyl-butyl ester | $IC_{50} = 5.82$ nM | $IC_{50} = 1.5$ uM |
| Example 96: carbamic acid 1-phenyl-4-(4-pyridin-2-yl-piperazin-1-yl)-butyl ester | $IC_{50} = 20.4$ nM | $IC_{50} = 3.14$ uM |
| Example 97: carbamic acid 4-[4-(3-chloro-pyridin-2-yl)-piperazin-1-yl]-1-phenol-butyl ester | $IC_{50} = 181$ nM | $IC_{50} = 519$ nM |
| Example 102: (R)-carbamic acid 3-[4-(4-methoxy-phenyl)-piperazin-1-yl]-1-phenyl-propyl ester | $IC_{50} = 4.31$ uM | $IC_{50} = 2.78$ uM |

For the use in treating various diseases such as a wide range of pains including acute pain, chronic pain, neuropathic pain, post-surgery neuropathic pain, diabetic neuropathic pain, postherpetic neuralgia, inflammatory pain, joint pain, migraine headache and the like, anxiety and depression), anxiety and depression, the compound of the present invention is administered to patient, alone or in combinations with pharmaceutically available carriers. An exact dose of the administered compound may be determined according to the conditions of patients, the severity of patient status and the activity of the compound. Under the specific circumstances, the optimum dose of the administered compound should essentially be determined in a clinical manner, but be present within the scope of the present invention.

For the use of the compound according to the present invention, the compound is preferably administered orally since the compound is easily absorbed orally, but the present invention is not particularly limited thereto. For the oral administration, the compound represented by Formula 1 is preferably used in combinations with a pharmaceutical carrier. A dose ratio of the carrier to the inventive compound is limited to allow the compound to take an effect on patients, and may be widely varied, depending on whether the composition is filled into a capsule, or formulated into a tablet. In the case of the tablet, edible and pharmaceutical carriers or mixtures thereof may be used herein. Examples of the suitable carriers includes, but are not particularly limited to, lactose, dibasic calcium phosphate and/or corn starch, and mixtures thereof, etc. Other pharmaceutically available compounds may be further added, including a lubricant such as magnesium stearate.

The invention claimed is:

1. A compound of Formula 1:

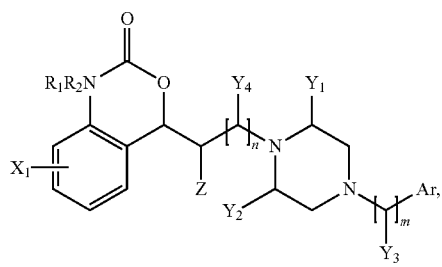

Formula 1 or a pharmaceutically acceptable salt thereof, wherein - - - denotes an optional bond forming a cyclic moiety;

R₁ and R₂ are H—, or R₁ and R₂ are taken together with the phenyl to form benzo[d][1,3]oxazin-2-one moiety;

X₁ is one or more substituents independently selected from the group consisting of H-, straight- or branched-chain $C_1$-$C_6$ alkyl, fluoro, chloro, bromo, straight- or branched-chain $C_1$-$C_6$ alkoxy, nitro, dimethylamino and trifluoromethyl, or X₁ is taken together with the phenyl to form naphthyl or methylenedioxyphenyl;

z is H— or fluoro;

Ar is selected from the group consisting of phenyl, pyridinyl, pyrimidinyl, naphthyl, dihydrobenzodioxinyl, methylenedioxyphenyl and quinoxalinyl, wherein each of phenyl, pyridinyl and pyrimidinyl is optionally substituted by one or more substituents independently selected from the group consisting of H-, straight- or branched-chain $C_1$-$C_6$ alkyl, hydroxy, halo, straight- or branched-chain $C_1$-$C_6$ alkoxy, nitro, acetyl, t-butylacetyl, trifluoromethyl, trifluoromethoxy, amino, benzyloxy, t-butylcarbonyloxy, benzyloxycarbonyloxy, ethanoyloxy, and cyclopentyloxy;

each of Y₁, Y₂ and Y₄ is independently H— or methyl;

Y₃ is H— or phenyl;

n is 1 or 2; and m is 0 or 1.

2. The compound of claim 1, wherein each of R₁, R₂ and X₁ is H—.

3. The compound of claim 1, wherein n is 1; and m is 0.

4. The compound of claim 1, wherein Ar is phenyl substituted with straight- or branched-chain $C_1$-$C_6$ alkoxy.

5. The compound of claim 4, which is selected from the group consisting of:

carbamic acid 3-[4-(2,4-dimethoxy-phenyl)-piperazin-1-yl]-1-phenyl-propyl ester;
carbamic acid 3-[4-(4-methoxy-phenyl)-piperazin-1-yl]-1-phenyl-propyl ester;
carbamic acid 3-[4-(3-methoxy-phenyl)-piperazin-1-yl]-1-phenyl-propyl ester;
carbamic acid 3-[4-(2-methoxy-phenyl)-piperazin-1-yl]-1-phenyl-propyl ester;
carbamic acid 3-[4-(3,5-dimethoxy-phenyl)-piperazin-1-yl]1-phenyl-propyl ester;
carbamic acid 3-[4-(5-chloro-2-methoxy-phenyl)-piperazin-1-yl]-1-phenyl-propyl ester;
carbamic acid 3-[4-(4-methoxy-phenyl)-piperazin-1-yl]-1-(4-nitro-phenyl)-propyl ester;
carbamic acid 1-(3-chloro-phenyl)-3-[4-(4-methoxy-phenyl)-piperazin-1-yl]-propyl ester;
carbamic acid 1-(2-fluoro-phenyl)-3-[4-(4-methoxy-phenyl)-piperazin-1-yl]-propyl ester;
carbamic acid 1-(4-methoxy-phenyl)-3-[4-(4-methoxy-phenyl)-piperazin-1-yl]-propyl ester;
carbamic acid 1-(4-tert-butyl-phenyl)-3-[4-(4-methoxy-phenyl)-piperazin-1-yl]-propyl ester;
carbamic acid 1-(2-chloro-phenyl)-3-[4-(4-methoxy-phenyl)-piperazin-1-yl]-propyl ester;
carbamic acid 3-[4-(4-methoxy-phenyl)-piperazin-1-yl]-1-(2-trifluoromethyl-phenyl)-propyl ester;
carbamic acid 1-(3,4-difluoro-phenyl)-3-[4-(4-methoxy-phenyl)-piperazin-1-yl]-propyl ester;
carbamic acid 1-(3-fluoro-phenyl)-3-[4-(4-methoxy-phenyl)-piperazin-1-yl]-propyl ester;
carbamic acid 1-(3-methoxy-phenyl)-3-[4-(4-methoxy-phenyl)-piperazin-1-yl]-propyl ester;
carbamic acid 3-[4-(4-methoxy-phenyl)-piperazin-1-yl]-1-p-tolyl-propyl ester;
carbamic acid 3-[4-(4-methoxy-phenyl)-piperazin-1-yl]-1-m-tolyl-propyl ester;
carbamic acid 1-(2,4-dichloro-phenyl)-3-[4-(4-methoxy-phenyl)-piperazin-1-yl]-propyl ester;
carbamic acid 3-[4-(4-methoxy-phenyl)-piperazin-1-yl]-1-o-tolyl-propyl ester;
carbamic acid 1-(2,4-dimethyl-phenyl)-3-[4-(4-methoxy-phenyl)-piperazin-1-yl]-propyl ester;
carbamic acid 1-(3,4-dimethyl-phenyl)-3-[4-(4-methoxy-phenyl)-piperazin-1-yl]-propyl ester;
carbamic acid 1-(2,5-dimethyl-phenyl)-3-[4-(4-methoxy-phenyl)-piperazin-1-yl]-propyl ester;
carbamic acid 1-(4-chloro-3-trifluoromethyl-phenyl)-3-[4-(4-methoxy-phenyl)-piperazin-1-yl]-propyl ester;
carbamic acid 3-[4-(4-methoxy-phenyl)-piperazin-1-yl]-1-(2-nitro-phenyl)-propyl ester;
carbamic acid 3-[4-(4-methoxy-phenyl)-piperazin-1-yl]1-(3-nitro-phenyl)-propyl ester;
carbamic acid 3-[4-(4-methoxy-phenyl)-piperazin-1-yl]1-(4-trifluoromethyl-phenyl)-propyl ester;
carbamic acid 1-benzol[1,3]dioxol-5-yl-3-[4-(4-methoxy-phenyl)-piperazin-1-yl]-propyl ester;
carbamic acid 3-[4-(4-methoxy-phenyl)-piperazin-1-yl]-1-(3-trifluoromethyl-phenyl)-propyl ester;
carbamic acid 1-(2-fluoro-phenyl)-3-[4-(4-methoxy-phenyl)-piperazin-1-yl]-propyl ester;
carbamic acid 1-(3,4-dichloro-phenyl)-3-[4-(4-methoxy-phenyl)-piperazin-1-yl]-propyl ester;
carbamic acid 1-(4-chloro-phenyl)-3-[4-(4-methoxy-phenyl)-piperazin-1-yl]-propyl ester;
carbamic acid 3-[4-(5-chloro-2-methoxy-phenyl)-piperazin-1-yl]-1-(4-fluoro-phenyl)-propyl ester;
carbamic acid 1-(4-fluoro-phenyl)-3-[4-(4-methoxy-phenyl)-piperazin-1-yl]-propyl ester;
carbamic acid 1-(4-fluoro-phenyl)-3-[4-(2-methoxy-phenyl)-piperazin-1-yl]-propyl ester;
carbamic acid 1-(4-chloro-phenyl)-3-[4-(2-methoxy-phenyl)-piperazin-1-yl]-propyl ester;
carbamic acid 4-[4-(2-methoxy-phenyl)-piperazin-1-yl]-1-phenyl-butyl ester;
carbamic acid (R)-3-[4-(4-methoxy-phenyl)-2,6-dimethyl-piperazin-1-yl]-1-phenyl-propyl ester;
(R)-carbamic acid 3-[4-(4-methoxy-phenyl)-piperazin-1-yl]-1-phenyl-propyl ester;
(S)-carbamic acid 3-[4-(4-methoxy-phenyl)-piperazin-1-yl]-1-phenyl-propyl ester;
4-{2-[4-(4-methoxy-phenyl)-piperazin-1-yl]-ethyl}-1,4-dihydro-benzo[d][1,3]oxazin-2-one;
carbamic acid 3-[4-(4-methoxy-phenyl)-piperazin-1-yl]-1-phenyl-butyl ester; and
carbamic acid 3-[4-(3,4-dimethoxy-phenyl)-piperazin-1-yl]-1-phenyl-butyl ester.

6. The compound of claim 1, which is selected from the group consisting of:

carbamic acid 1-phenyl-3-(4-phenyl-piperazin-1-yl)-propyl ester;
carbamic acid 1-(4-chloro-phenyl)-3-(4-phenyl-piperazin-1-yl)-propyl ester;
carbamic acid 1-(4-dimethylamino-phenyl)-3-(4-phenyl-piperazin-1-yl)-propyl ester;
carbamic acid 1-(3-nitro-phenyl)-3-(4-phenyl-piperazin-1-yl)-propyl ester;
carbamic acid 1-(4-tert-butyl-phenyl)-3-(4-phenyl-piperazin-1-yl)-propyl ester;
carbamic acid 1-(4-fluoro-phenyl)-3-(4-phenyl-piperazin-1-yl)-propyl ester;

carbamic acid 1-(3-chloro-phenyl)-3-(4-phenyl-piperazin-1-yl)-propyl ester;
carbamic acid 1-(4-methoxy-phenyl)-3-(4-phenyl-piperazin-1-yl)-propyl ester;
carbamic acid 1-(4-nitro-phenyl)-3-(4-phenyl-piperazin-1-yl)-propyl ester;
carbamic acid 3-(4-phenyl-piperazin-1-yl)-1-p-tolyl-propyl ester;
carbamic acid 3-[4-(2,3-dihydro-benzo[1,4]dioxin-6-yl)-piperazin-1-yl]-1-phenyl-propyl ester;
carbamic acid 1-phenyl-3-[4-(4-trifluoromethoxy-phenyl)-piperazin-1-yl]-propyl ester;
carbamic acid 3-[4-(2,4-dimethyl-phenyl)-piperazin-1-yl]-1-phenyl-propyl ester;
carbamic acid 1-phenyl-3-[4-(2-trifluoromethyl-phenyl)-piperazin-1-yl]-propyl ester;
carbamic acid 1-phenyl-3-[4-(2-chloro-phenyl)-piperazin-1-yl]-propyl ester;
carbamic acid 1-phenyl-3-[4-(4-nitro-phenyl)-piperazin-1-yl]-propyl ester;
carbamic acid 3-[4-(4-chloro-3-trifluoromethyl-phenyl)-piperazin-1-yl]-1-phenyl-propyl ester;
carbamic acid 3-[4-(2,6-dimethyl-phenyl)-piperazin-1-yl]-1-phenyl-propyl ester;
carbamic acid 3-[4-(4-fluoro-phenyl)-piperazin-1-yl]-1-phenyl-propyl ester;
carbamic acid 3-[4-(4-chloro-phenyl)-piperazin-1-yl]-1-phenyl-propyl ester;
carbamic acid 3-[4-(2-hydroxy-phenyl)-piperazin-1-yl]-1-phenyl-propyl ester;
carbamic acid 1-phenyl-3-(4-m-tolyl-piperazin-1-yl)-propyl ester;
carbamic acid 3-[4-(3,4-dimethyl-phenyl)-piperazin-1-yl]-1-phenyl-propyl ester;
carbamic acid 3-(4-benzo[1,3]dioxol-5-yl-piperazin-1-yl)-1-phenyl-propyl ester;
carbamic acid 3-[4-(3,4-dichloro-phenyl)-piperazin-1-yl]-1-phenyl-propyl ester;
carbamic acid 3-[4-(2-nitro-4-trifluoromethyl-phenyl)-piperazin-1-yl]-1-phenyl-propyl ester;
carbamic acid 3-[4-(3-chloro-phenyl)-piperazin-1-yl]-1-phenyl-propyl ester;
carbamic acid 1-phenyl-3-(4-o-tolyl-piperazin-1-yl)-propyl ester;
carbamic acid 1-phenyl-3-(4-p-tolyl-piperazin-1-yl)-propyl ester;
carbamic acid 1-phenyl-3-[4-(3-trifluoromethyl-phenyl)-piperazin-1-yl]-propyl ester;
carbamic acid 1-phenyl-3-[4-(4-trifluoromethyl-phenyl)-piperazin-1-yl]-propyl ester;
carbamic acid 3-[4-(2-fluoro-phenyl)-piperazin-1-yl]-1-phenyl-propyl ester;
carbamic acid 3-[4-(3-fluoro-phenyl)-piperazin-1-yl]-1-phenyl-propyl ester;
carbamic acid 3-[4-(2-nitro-phenyl)-piperazin-1-yl]-1-phenyl-propyl ester;
carbamic acid 1-(4-chloro-3-trifluoromethyl-phenyl)-3-[4-(4-hydroxy-phenyl)-piperazin-1-yl]-propyl ester;
carbamic acid 1-(3,4-dichloro-phenyl)-3-[4-(4-hydroxy-phenyl)-piperazin-1-yl]-propyl ester;
carbamic acid 3-[4-(2-ethoxy-phenyl)-piperazin-1-yl]-1-(4-fluoro-phenyl)-propyl ester;
carbamic acid 3-[4-(3,4-dichloro-phenyl)-piperazin-1-yl]-1-(4-fluoro-phenyl)-propyl ester;
carbamic acid 1-(4-fluoro-phenyl)-3-[4-(4-nitro-phenyl)-piperazin-1-yl]-propyl ester;
carbamic acid 1-(4-fluoro-phenyl)-3-(4-o-tolyl-piperazin-1-yl)-propyl ester;
carbamic acid 1-(4-fluoro-phenyl)-3-[4-(4-fluoro-phenyl)-piperazin-1-yl]-propyl ester;
carbamic acid 3-[4-(4-hydroxy-phenyl)-piperazin-1-yl]-1-phenyl-propyl ester;
carbamic acid 3-[4-(4-benzyloxyphenyl)-piperazin-1-yl]-1-phenyl-propyl ester;
acetic acid 4-[4-(3-carbamoyloxy-3-phenyl-propyl)-piperazin-1-yl]-phenyl ester;
carbamic acid 3-[4-(4-cyclopentyloxy-phenyl)-piperazin-1-yl]-1-phenyl-propyl ester;
carbamic acid 1-(4-fluoro-phenyl)-3-[4-(4-hydroxy-phenyl)-piperazin-1-yl]-propyl ester;
1-(4-fluorophenyl)-3-(4-(4-(pivaloyloxy)phenyl)piperazin-1-yl)-propyl carbamate;
carbonic acid 4-{4-[3-carbamoyloxy-3-(4-fluoro-phenyl)-propyl]-piperazin-1-yl}-phenyl ethyl ester;
carbonic acid benzyl ester 4-{4-[3-carbamoyloxy-3-(4-fluoro-phenyl)-propyl]-piperazin-1-yl}-phenyl ester;
acetic acid 4-{4-[3-carbamoyloxy-3-(4-fluoro-phenyl)-propyl]-piperazin-1-yl}-phenyl ester;
carbamic acid 1-phenyl-4-(4-phenyl-piperazin-1-yl)-butyl ester;
carbamic acid 3-(4-benzo[1,3]dioxol-5-ylmethyl-piperazin-1-yl)-1-phenyl-propyl ester;
carbamic acid 3-(4-benzyl-piperazin-1-yl)-1-phenyl-propyl ester
(R)-carbamic acid 3-[4-(4-chloro-phenyl)-piperazin-1-yl]-1-phenyl-propyl ester;
(R)-carbamic acid 3-[4-(4-fluoro-phenyl)-piperazin-1-yl]-1-phenyl-propyl ester;
(R)-carbamic acid 3-[4-(4-hydroxy-phenyl)-piperazin-1-yl]-1-phenyl-propyl ester;
carbamic acid 3-[4-(4-chloro-phenyl)-piperazin-1-yl]-1-phenyl-butyl ester;
carbamic acid 3-[4-(4-nitro-phenyl)-piperazin-1-yl]-1-phenyl-butyl ester;
carbamic acid 3-[4-(3,4-dimethyl-phenyl)-piperazin-1-yl] 1-phenyl-butyl ester;
carbamic acid 3-[4-(4-quinoxalinyl)-piperazin-1-yl]-1-phenyl-butyl ester;
carbamic acid 3-[4-(3,4-dichloro-phenyl)-piperazin-1-yl]-1-phenyl-butyl ester;
carbamic acid 3-[4-(2,4-difluoro-phenyl)-piperazin-1-yl]-1-phenyl-butyl ester; and
carbamic acid 2-fluoro-1-phenyl-3-(4-phenyl-piperazin-1-yl)-propyl ester.

7. The compound of claim 1, which is selected from the group consisting of:
carbamic acid 1-phenyl-3-(4-pyridin-2-yl-piperazin-1-yl)-propyl ester;
carbamic acid 3-[4-(3-chloro-pyridin-2-yl)-piperazin-1-yl]-1-phenyl-propyl ester;
carbamic acid 3-[4-(3,5-dichloro-pyridin-2-yl-piperazin-1-yl]-1-phenyl-butyl ester;
carbamic acid 1-phenyl-4-(4-pyridin-2-yl-piperazin-1-yl)-butyl ester;
carbamic acid 4-[4-(3-chloro-pyridin-2-yl)-piperazin-1-yl]-1-phenyl-butyl ester; and
carbamic acid 1-phenyl-3-(4-pyrimidin-2-yl-piperazin-1-yl)-propyl ester.

8. The compound of claim 1, which is selected from the group consisting of:
carbamic acid 3-[4-(4-methoxy-phenyl)-piperazin-1-yl]1-naphthalen-2-yl-propyl ester; and carbamic acid 3-[4-(4-methoxy-phenyl)-piperazin-1-yl]-1-naphthalen-1-yl-propyl ester.

9. The compound of claim 1, which is selected from the group consisting of:
   carbamic acid (R)-3-[4-(4-methoxy-phenyl)-2,6-dimethyl-piperazin-1-yl]-1-phenyl-propyl ester;
   (R)-carbamic acid 3-[4-(4-methoxy-phenyl)-piperazin-1-yl]-1-phenyl-propyl ester;
   (R)-carbamic acid 3-[4-(4-chloro-phenyl)-piperazin-1-yl]-1-phenyl-propyl ester;
   (R)-carbamic acid 3-[4-(4-fluoro-phenyl)-piperazin-1-yl]-1-phenyl-propyl ester;
   (R)-carbamic acid 3-[4-(4-hydroxy-phenyl)-piperazin-1-yl]-1-phenyl-propyl ester; and
   (S)-carbamic acid 3-[4-(4-methoxy-phenyl)-piperazin-1-yl]-1-phenyl-propyl ester.

10. The compound of claim 1, wherein the compound is selected from the group consisting of:
    carbamic acid 1-(4-chloro-phenyl)-3-(4-phenyl-piperazin-1-yl)-propyl ester;
    carbamic acid 1-(4-fluoro-phenyl)-3-(4-phenyl-piperazin-1-yl)-propyl ester;
    carbamic acid 1-(4-nitro-phenyl)-3-(4-phenyl-piperazin-1-yl)-propyl ester;
    carbamic acid 1-phenyl-3-[4-(4-nitro-phenyl)-piperazin-1-yl]-propyl ester;
    carbamic acid 3-[4-(4-methoxy-phenyl)-piperazin-1-yl]-1-phenyl-propyl ester;
    carbamic acid 3-[4-(4-fluoro-phenyl)-piperazin-1-yl]-1-phenyl-propyl ester; and
    (R)-carbamic acid 3-[4-(4-methoxy-phenyl)-piperazin-1-yl]-1-phenyl-propyl ester.

11. The compound of claim 1, wherein the compound is (R)-carbamic acid 3-[4-(4-methoxy-phenyl)-piperazin-1-yl]-1-phenyl-propyl ester.

12. A compound which is selected from the group consisting of:
    carbamic acid 2-[4-(4-methoxy-phenyl)-piperazin-1-ylmethyl]-1,2,3,4-tetrahydro-naphthalen-1-yl ester;
    carbamic acid 3-{4-[bis-(4-fluoro-phenyl)-methyl]-piperazin-1-yl}-1-phenyl-propyl ester; and
    carbamic acid 3-(4-benzoyl-piperazin-1-yl)-1-phenyl-propyl ester.

13. A pharmaceutical composition comprising a therapeutically effective amount of the compound of claim 1 and a pharmaceutically acceptable carrier.

14. The pharmaceutical composition of claim 13, wherein the compound is selected from the group consisting of:
    carbamic acid 1-(4-chloro-phenyl)-3-(4-phenyl-piperazin-1-yl)-propyl ester;
    carbamic acid 1-(4-fluoro-phenyl)-3-(4-phenyl-piperazin-1-yl)-propyl ester;
    carbamic acid 1-(4-nitro-phenyl)-3-(4-phenyl-piperazin-1-yl)-propyl ester;
    carbamic acid 1-phenyl-3-[4-(4-nitro-phenyl)-piperazin-1-yl]-propyl ester;
    carbamic acid 3-[4-(4-methoxy-phenyl)-piperazin-1-yl]-1-phenyl-propyl ester;
    carbamic acid 3-[4-(4-fluoro-phenyl)-piperazin-1-yl]-1-phenyl-propyl ester; and
    (R)-carbamic acid 3-[4-(4-methoxy-phenyl)-piperazin-1-yl]-1-phenyl-propyl ester.

15. The pharmaceutical composition of claim 13, wherein the compound is (R)-carbamic acid 3-[4-(4-methoxy-phenyl)-piperazin-1-yl]-1-phenyl-propyl ester.

16. The pharmaceutical composition of claim 13, wherein the therapeutically effect amount is in the range of 10 to 500 mg.

17. A method for treating pain, anxiety or depression, comprising administering to a patient in need of treatment an effective amount of the compound of claim 1.

18. The method of claim 17, wherein the compound is (R)-carbamic acid 3-[4-(4-methoxy-phenyl)-piperazin-1-yl]-1-phenyl-propyl ester.

19. The method of claim 17, wherein the pain is selected from the group consisting of acute pain, chronic pain, neuropathic pain, post-surgery neuropathic pain, diabetic pain, postherpetic neuralgia, inflammatory pain, joint pain and migraine headache.

20. The method of claim 17, wherein the therapeutically effect amount is in the range of 10 to 500 mg.

* * * * *

UNITED STATES PATENT AND TRADEMARK OFFICE
CERTIFICATE OF CORRECTION

PATENT NO. : 8,815,852 B2
APPLICATION NO. : 12/600283
DATED : August 26, 2014
INVENTOR(S) : Ki Ho Lee et al.

It is certified that error appears in the above-identified patent and that said Letters Patent is hereby corrected as shown below:

In the Specification

Column 73, in Table 2 at Example 95, replace "$IC_{50}$ = 1.5 μM" with "$IC_{50}$ = 1.15 μM".

Signed and Sealed this
Tenth Day of February, 2015

Michelle K. Lee
*Deputy Director of the United States Patent and Trademark Office*